(12) United States Patent
Morrison et al.

(10) Patent No.: US 12,351,588 B2
(45) Date of Patent: Jul. 8, 2025

(54) SALT FORMS AND SOLVATES OF MCL-1 ANTAGONISTS

(71) Applicant: AMGEN INC., Thousand Oaks, CA (US)

(72) Inventors: Henry Morrison, Thousand Oaks, CA (US); Jason S. Tedrow, Salem, MA (US); Stephan D. Parent, West Lafayette, IN (US); Courtney Johnson, West Lafayette, IN (US); Travis Houston, West Lafayette, IN (US); Melanie Bevill, West Lafayette, IN (US)

(73) Assignee: AMGEN INC., Thousand Oaks, CA (US)

( * ) Notice: Subject to any disclaimer, the term of this patent is extended or adjusted under 35 U.S.C. 154(b) by 278 days.

(21) Appl. No.: 18/296,215

(22) Filed: Apr. 5, 2023

(65) Prior Publication Data

US 2023/0312602 A1 Oct. 5, 2023

Related U.S. Application Data

(60) Provisional application No. 63/327,659, filed on Apr. 5, 2022.

(51) Int. Cl.
*C07D 513/08* (2006.01)
(52) U.S. Cl.
CPC ........ *C07D 513/08* (2013.01); *C07B 2200/13* (2013.01)

(58) Field of Classification Search
CPC .................. C07D 513/08; C07B 2200/13
See application file for complete search history.

(56) References Cited

U.S. PATENT DOCUMENTS 9,562,061 B2 2/2017 Brown et al.

*Primary Examiner* — John S Kenyon
*Assistant Examiner* — John D McAnany
(74) *Attorney, Agent, or Firm* — MARSHALL, GERSTEIN & BORUN LLP

(57) ABSTRACT

Disclosed herein are salt and solvate forms of. (1S,3'R,6'R,7'S,8'E,11'S,12'R)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (AMG 176):

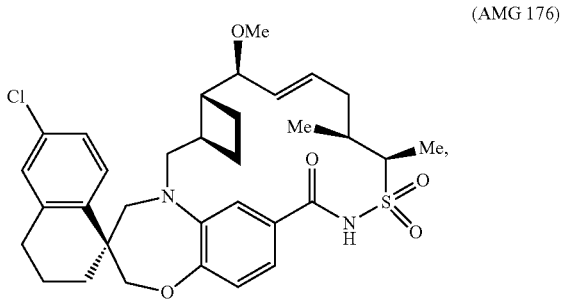

such as crystalline salt and solvate forms thereof. Also disclosed are methods of making the salt and solvate forms, and methods of treating diseases and disorders with the salt and solvate forms.

17 Claims, 23 Drawing Sheets

SALT FORMS AND SOLVATES OF MCL-1 ANTAGONISTS

BACKGROUND

Technical Field

The present disclosure relates to salt and solvate forms of (1S,3'R,6'R,7'S,8'E,11'S,12'R)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (AMG 176), such as crystalline salt and solvate forms, which function as an inhibitor of myeloid cell leukemia 1 protein (Mcl-1).

Description of Related Technology

The compound, (1S,3'R,6'R,7'S,8'E,11'S,12'R)-6-chloro-7'-methoxy-11',12'-dimethyl-3,4-dihydro-2H,15'H-spiro[naphthalene-1,22'-[20]oxa[13]thia[1,14]diazatetracyclo[14.7.2.0$^{3,6}$.0$^{19,24}$]pentacosa[8,16,18,24]tetraen]-15'-one 13',13'-dioxide (AMG 176), is useful as an inhibitor of myeloid cell leukemia 1 ("Mcl-1"):

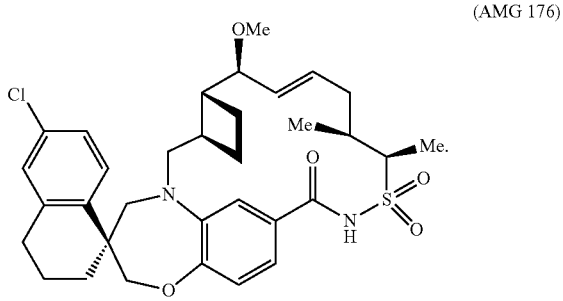

(AMG 176)

One common characteristic of human cancer is overexpression of Mcl-1. Mcl-1 overexpression prevents cancer cells from undergoing programmed cell death (apoptosis), allowing the cells to survive despite widespread genetic damage.

Mcl-1 is a member of the Bcl-2 family of proteins. The Bcl-2 family includes pro-apoptotic members (such as BAX and BAK) which, upon activation, form a homo-oligomer in the outer mitochondrial membrane that leads to pore formation and the escape of mitochondrial contents, a step in triggering apoptosis. Antiapoptotic members of the Bcl-2 family (such as Bcl-2, Bcl-XL, and Mcl-1) block the activity of BAX and BAK. Other proteins (such as BID, BIM, BIK, and BAD) exhibit additional regulatory functions. Research has shown that Mcl-1 inhibitors can be useful for the treatment of cancers. MCl-1 is overexpressed in numerous cancers.

U.S. Pat. No. 9,562,061, which is incorporated herein by reference in its entirety, discloses AMG 176 as an Mcl-1 inhibitor and provides a method for preparing it. However, alternative forms of AMG 176 with improved properties are desirable, particularly for clinical use of AMG 176.

SUMMARY

Provided herein are crystalline salt and solvate forms of AMG 176, wherein AMG 176 has the structure

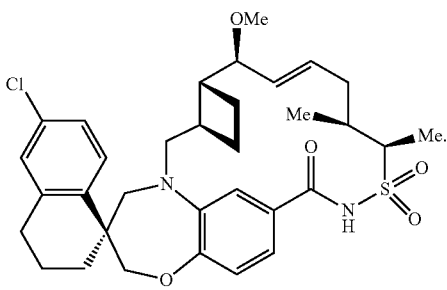

Also provided are crystalline forms of AMG 176 as an ammonium salt, characterized by XRPD pattern peaks at 16.6, 17.6, and 18.4±0.2° 2θ using Cu Kα radiation.

Also provided are crystalline forms of AMG 176 as a diethylamine salt characterized by an XRPD pattern substantially as shown in FIG. 5 ("Diethylamine Form A").

Also provided are crystalline forms of AMG 176 as a diethylamine salt characterized by an XRPD pattern substantially as shown in FIG. 7 ("Diethylamine Form B").

Also provided are crystalline forms of AMG 176 as a diethanolamine salt characterized by an XRPD pattern substantially as shown in FIG. 9 ("Diethanolamine Salt Toluene Solvate").

Also provided are crystalline forms of AMG 176 as a diethanolamine salt characterized by an XRPD pattern substantially as shown in FIG. 11 ("Diethanolamine Salt Anhydrous").

Also provided are crystalline forms of AMG 176 as a 1,4-dioxane solvate characterized by XRPD pattern peaks at 12.4, 12.8, 15.8, and 17.7±0.2° 2θ using Cu Kα radiation.

Also provided are crystalline forms of AMG 176 as an imidazole salt acetone solvate characterized by XRPD pattern peaks at 4.2, 8.1, and 20.7±0.2° 2θ using Cu Kα radiation.

Also provided are crystalline forms of AMG 176 as a hemi magnesium salt dihydrate characterized by XRPD pattern peaks at 3.8, 5.8, and 7.5±0.2° 2θ using Cu Kα radiation.

Also provided are crystalline forms of AMG 176 as a methyl tert-butyl ether solvate characterized by XRPD pattern peaks at 12.4, 15.6, and 20.1±0.2° 2θ using Cu Kα radiation.

Also provided are crystalline forms of AMG 176 as a 2-methyltetrahydrofuran solvate characterized by XRPD pattern peaks at 12.4, 15.6, and 20.1±0.2° 2θ using Cu Kα radiation.

Also provided are crystalline forms of AMG 176 as a potassium salt hydrate characterized by XRPD pattern peaks at 5.9, 7.6, and 23.5±0.2° 2θ using Cu Kα radiation.

Also provided are crystalline forms of AMG 176 as a potassium salt isopropanol solvate characterized by XRPD pattern peaks at 5.8, 18.7, 22.5, and 23.5±0.2° 2θ using Cu Kα radiation.

Also provided are crystalline forms of AMG 176 as a tetrahydrofuran solvate characterized by XRPD pattern peaks at 12.5, 15.8, and 17.8±0.2° 2θ using Cu Kα radiation.

Also provided are crystalline forms of AMG 176 as a sodium salt acetonitrile solvate characterized by XRPD pattern peaks at 3.4, 3.7, and 16.7±0.2° 2θ using Cu Kα radiation.

Also provided are pharmaceutical formulations comprising the crystalline or amorphous forms of AMG 176 as described herein and a pharmaceutically acceptable excipient.

Also provided are methods of treating a subject suffering from cancer, comprising administering to the subject a therapeutically effective amount of the crystalline or amorphous forms of AMG 176 as described herein, or the pharmaceutical formulations comprising the crystalline or amorphous forms of AMG 176 as described herein and a pharmaceutically acceptable excipient.

DETAILED DESCRIPTION

Figure 1:
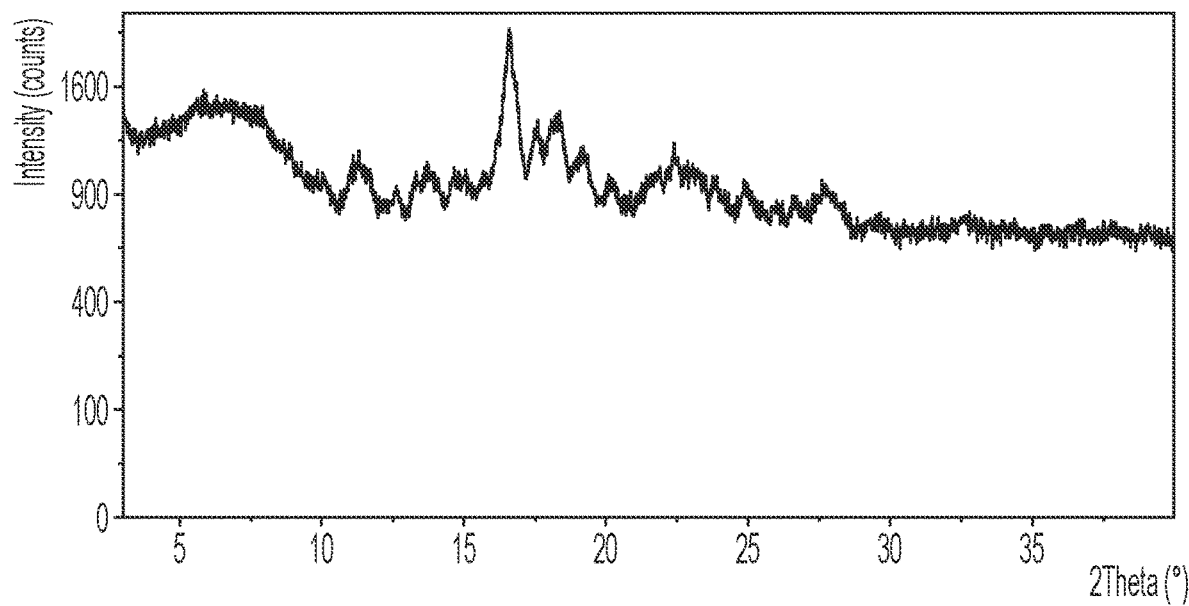
FIG. 1 depicts an X-ray powder diffraction ("XRPD") pattern of the crystalline ammonium salt form of AMG 176.

Disclosed herein are salt and solvate forms of (1S,3'R, 6'R,7'S,8'E,11'S,12'R)-6-chloro-7'-methoxy-11',12'-dimethyl-3,4-dihydro-2H,15'H-spiro[naphthalene-1,22'-[20]oxa [13]thia[1,14]diazatetracyclo[14.7.2.0$^{3,6}$.0$^{19,24}$]pentacosa [8,16,18,24]tetraen]-15'-one 13',13'-dioxide (AMG 176), such as crystalline salt and solvate forms thereof:

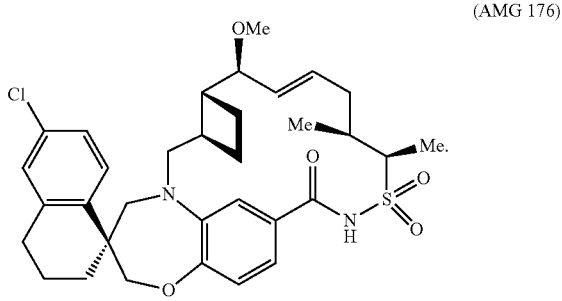

(AMG 176)

AMG 176 Form 1 is a stable crystalline form suitable for development, however solubility is low under neutral conditions (<0.1 [ g/mL in water). The amorphous form and salt and solvate forms of AMG 176 may provide solubility advantages for dosage form development. The crystal forms described here have unique physical properties which can be advantageous for new formulations of AMG 176.

Also provided herein pharmaceutical formulations of salt and solvate forms of AMG 176, and methods of treating a subject suffering from cancer, comprising administering to the subject a therapeutically effective amount of a pharmaceutical formulation of a salt or solvate form as disclosed herein.

U.S. Pat. No. 9,562,061, which is incorporated by reference herein in its entirety, discloses synthetic procedures for synthesizing Mcl-1 inhibitors, such as AMG 176.

Further provided herein are crystalline salt and solvate forms of AMG 176, pharmaceutical formulations thereof, and methods of treating a subject suffering from cancer, comprising administering to the subject a therapeutically effective amount of a pharmaceutical formulation of a crystalline salt or solvate form as disclosed herein.

The compounds disclosed herein may be identified either by their chemical structure and/or chemical name herein. When the chemical structure and chemical name conflict, the chemical structure is determinative of the identity of the compound.

When ranges are used herein for physical properties, such as molecular weight, or chemical properties, such as chemical formulae, all combinations and subcombinations of ranges and specific embodiments therein are intended to be included.

As used herein, chemical structures which contain one or more stereocenters depicted with dashed and bold bonds (i.e., ⋰ and ⋰) are meant to indicate absolute stereochemistry of the stereocenter(s) present in the chemical structure. As used herein, bonds symbolized by a simple line do not indicate a stereo-preference. Unless otherwise indicated to the contrary, chemical structures that include one or more stereocenters which are illustrated herein without indicating absolute or relative stereochemistry encompass all possible stereoisomeric forms of the compound (e.g., diastereomers, enantiomers) and mixtures thereof. Structures with a single bold or dashed line, and at least one additional simple line, encompass a single enantiomeric series of all possible diastereomers.

The term "about" is meant to account for variations due to experimental error. All measurements reported herein are understood to be modified by the term "about," whether or not the term is explicitly used, unless explicitly stated otherwise. As used herein, the singular forms "a," "an," and "the" include plural referents unless the context clearly dictates otherwise.

"Treatment" or "treating" means any treatment of a disease in a patient, including: a) preventing the disease, that is, causing the clinical symptoms of the disease not to develop; b) inhibiting the disease; c) slowing or arresting the development of clinical symptoms; and/or d) relieving the disease, that is, causing the regression of clinical symptoms. Treatment of diseases and disorders herein is intended to also include the prophylactic administration of a pharmaceutical formulation described herein to a subject (i.e., an animal, preferably a mammal, most preferably a human) believed to be in need of treatment, such as, for example, cancer.

"Salts" are ionic compounds formed by the treatment of AMG 176 with an acid or base. Any salt that is consistent with the overall stability and utility of the compounds of AMG 176 may be provided using conventional methods. Suitable salts include, without limitation, salts of acidic or basic groups that can be present in the compounds provided herein. Under certain acidic conditions, the compound can form a wide variety of salts with various inorganic and organic acids. Acids that can be used to prepare pharmaceutically acceptable salts of such basic compounds are those that form salts comprising pharmacologically acceptable anions including, but not limited to, acetate, benzenesulfonate, benzoate, bicarbonate, bitartrate, bromide, calcium edetate, camsylate, carbonate, chloride, bromide, iodide, citrate, dihydrochloride, edetate, edisylate, estolate, esylate, fumarate, gluceptate, gluconate, glutamate, glycollylarsanilate, hexylresorcinate, hydrabamine, hydroxynaphthoate, isethionate, lactate, lactobionate, malate, maleate, mandelate, mesylate (methylenesulfonate), methylsulfate, muscate, napsylate, nitrate, panthothenate, phosphate/diphosphate, polygalacturonate, salicylate, stearate, succinate, sulfate, tannate, tartrate, teoclate, triethiodide, and pamoate. Under certain basic conditions, the compound can form base salts with various pharmacologically acceptable cations. Non-limiting examples of such salts include alkali metal or alkaline earth metal salts and, particularly, calcium, magnesium, sodium, lithium, zinc, potassium and iron salts, as well as tetraalkylammonium salts. General information regarding pharmaceutically acceptable salts may be found in Stahl PH, and Wermuth CG, eds., *Handbook of Pharmaceutical Salts: Properties, Selection and Use,* 2002, Wiley-VCH/VHCA Weinheim/Zürich.

The term "therapeutically effective amount" means an amount effective, when administered to a human or non-human patient, to treat a disease, e.g., a therapeutically effective amount may be an amount sufficient to treat a disease or disorder responsive to myosin activation. The therapeutically effective amount may be ascertained experimentally, for example by assaying blood concentration of the chemical entity, or theoretically, by calculating bioavailability.

The term "solvate" refers to the chemical entity formed by the interaction of a solvent and a compound. Crystalline solvates of AMG 176 used in formulations herein are specifically contemplated. Solvents that can form crystalline solvate forms of AMG 176 include without limitation, toluene, 1,4-dioxane, acetone, methyl tert-butyl ether, 2-methyltetrahydrofuran, isopropanol, tetrahydrofuran, and acetonitrile. In some cases, a solvate has 0.5 to 2 solvent molecules per AMG 176 molecule.

Salt and Solvate Forms

Ammonium Salt Form: The crystalline ammonium salt form of AMG 176 can be characterized by an X-ray powder diffraction pattern, obtained as set forth in the Examples, having peaks at 16.6, 17.6, and 18.4±0.2° 2θ using Cu Kα radiation, optionally further characterized by additional peaks at 19.2, 21.6, 22.4, and 23.8±0.2° 2θ using Cu Kα radiation, and/or additional peaks at 7.9, 10.1, 11.0, 12.7, 13.9, 20.2, 24.9, 27.7, and 29.8±0.2° 2θ using Cu Kα radiation. In some embodiments, the crystalline ammonium salt form of AMG 176 has an X-ray powder diffraction pattern substantially as shown in FIG. 1, wherein by "substantially" is meant that the reported peaks can vary by ±0.2°. It is well known in the field of XRPD that while relative peak heights in spectra are dependent on a number of factors, such as sample preparation and instrument geometry, peak positions are relatively insensitive to experimental details.

Figure 2:
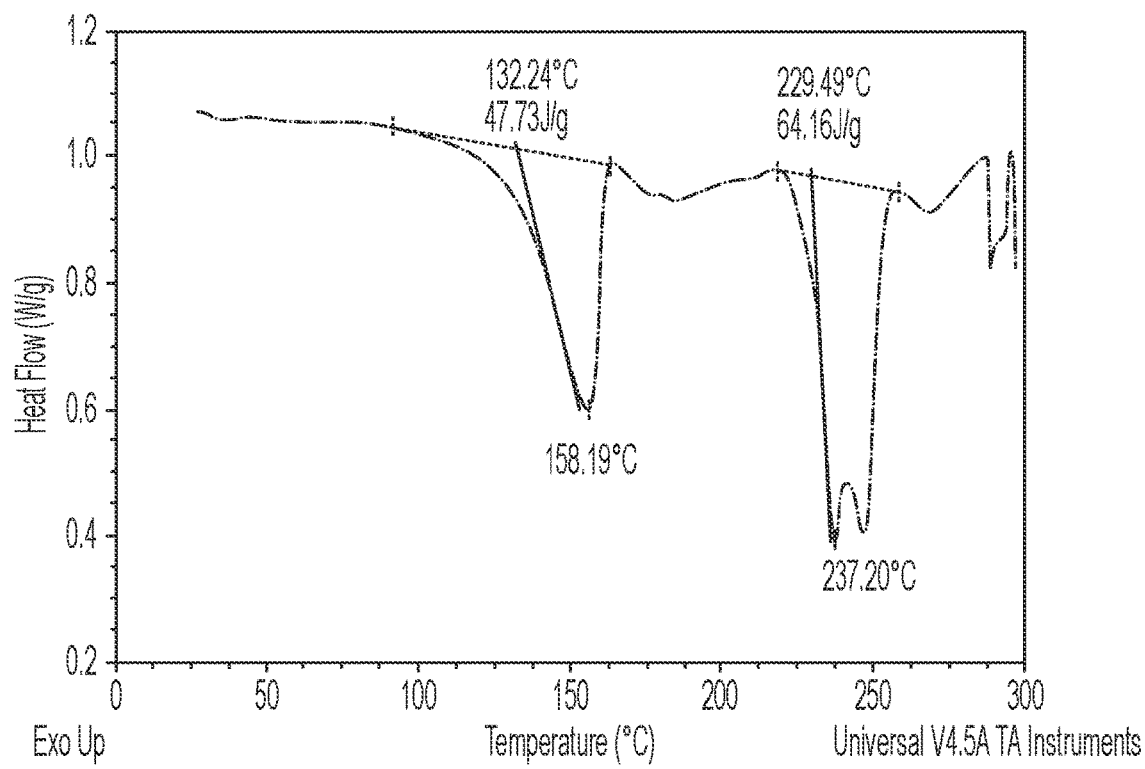
FIG. 2 depicts a differential scanning calorimetry ("DSC") thermograph of the crystalline ammonium salt form of AMG 176 indicating a Tm of 156° C.

Differential scanning calorimetry (DSC) thermographs were obtained, as set forth in the Examples, for the crystalline ammonium salt form of AMG 176. The DSC curve indicates an endothermic transition at 156° C.±3° C. For example, in some embodiments the crystalline ammonium salt form of AMG 176 is characterized by DSC, as shown in FIG. 2.

Figure 3:
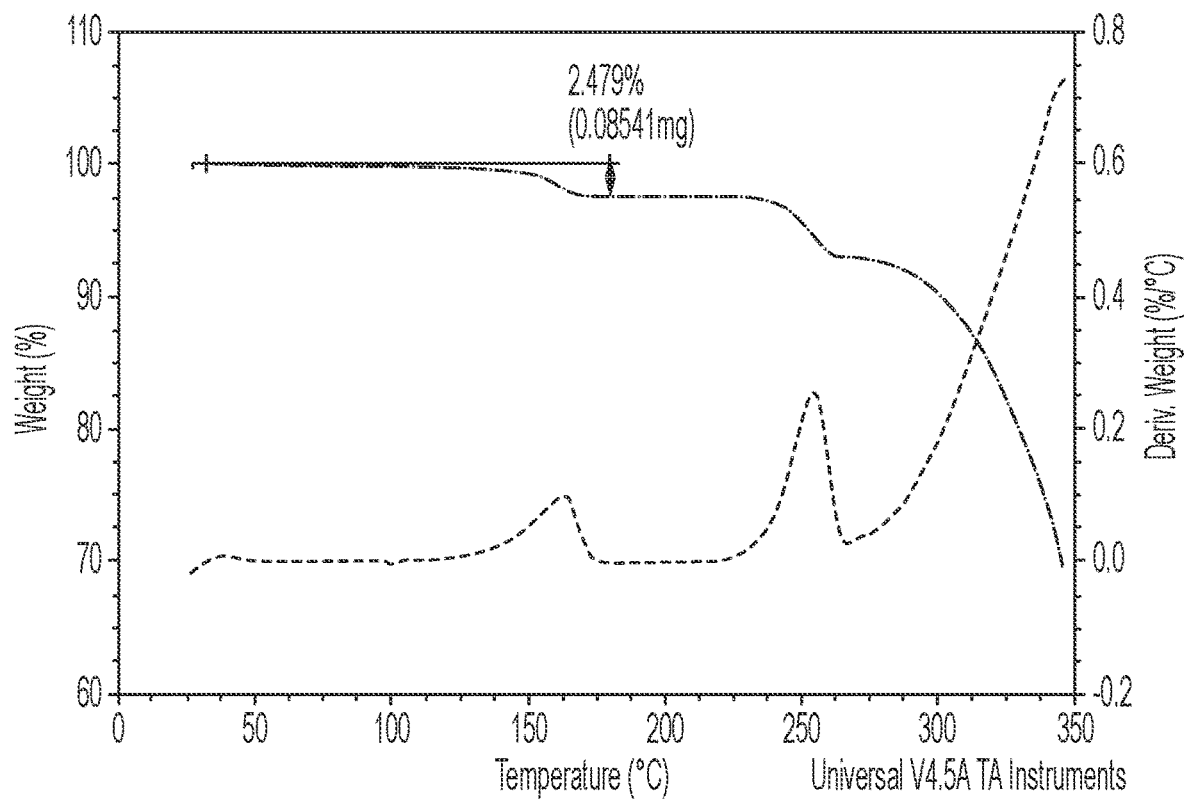
FIG. 3 depicts a thermogravimetric analysis ("TGA") trace of the crystalline ammonium salt form of AMG 176 showing 2.5% weight loss.

The crystalline ammonium salt form of AMG 176 can be characterized by thermogravimetric analysis (TGA). Thus, the crystalline ammonium salt form of AMG 176 can be characterized by a weight loss in a range of about 2.5%. In some embodiments, the crystalline ammonium salt form of AMG 176 has a thermogravimetric analysis substantially as depicted in FIG. 3, wherein by "substantially" is meant that the reported TGA features can vary by ±5° C.

Figure 4:
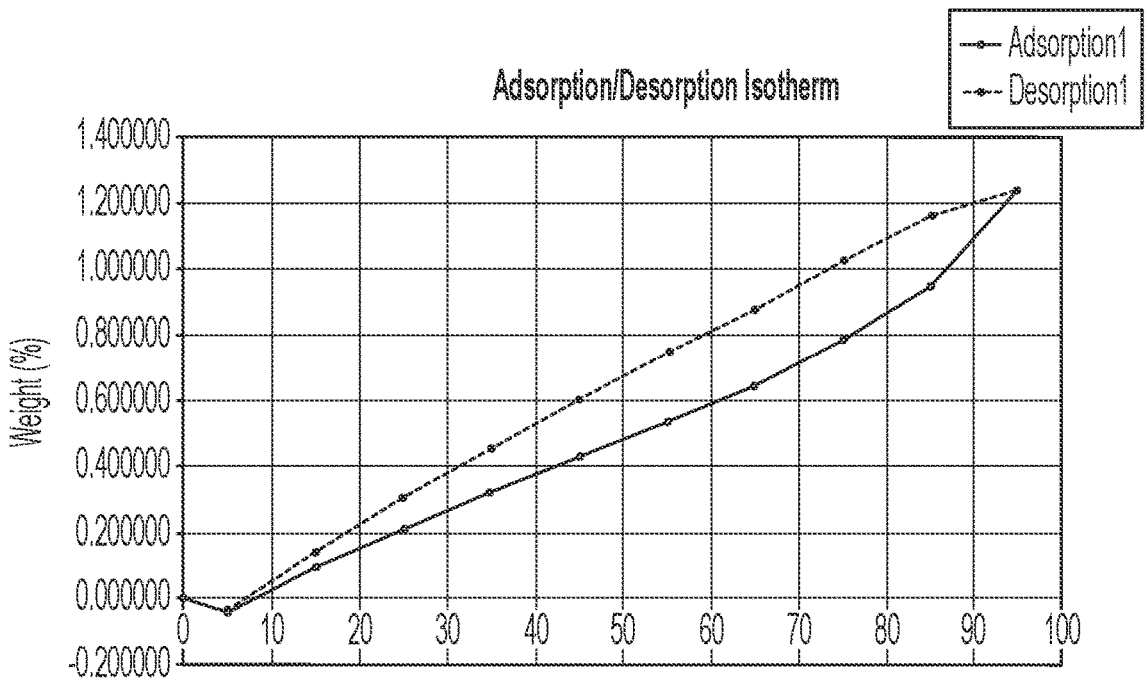
FIG. 4 depicts a moisture sorption profile (DVS) of the crystalline ammonium salt form of AMG 176 showing weight gain of about 1.2% by 95% relative humidity.

The crystalline ammonium salt form of AMG 176 can be characterized by a moisture sorption profile. For example, in some embodiments, the crystalline ammonium salt form of AMG 176 is characterized by the moisture sorption profile as shown in FIG. 4, showing a weight gain of about 1.2% by 95% relative humidity.

Figure 5:
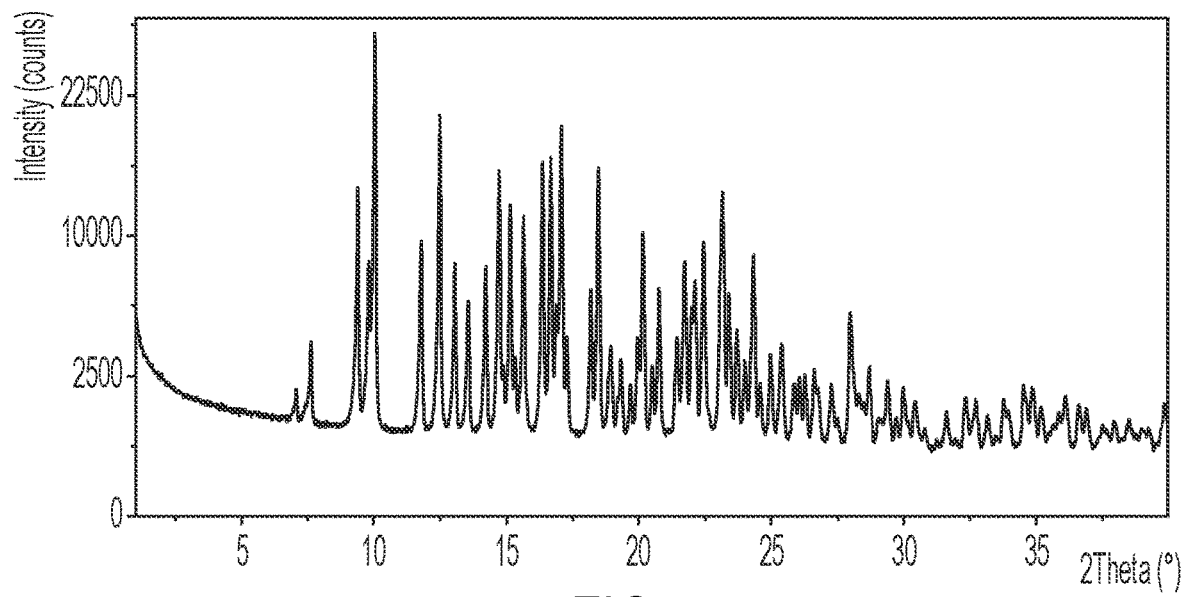
FIG. 5 depicts an X-ray powder diffraction ("XRPD") pattern of the crystalline diethylamine salt form A of AMG 176.

Diethylamine Salt Form A (Diethylamine Salt Toluene Solvate): The crystalline diethylamine salt form A of AMG 176 can be characterized by an X-ray powder diffraction pattern, obtained as set forth in the Examples, for example, an X-ray powder diffraction pattern substantially as shown in FIG. 5, wherein by "substantially" is meant that the reported peaks can vary by ±0.2°. It is well known in the field of XRPD that while relative peak heights in spectra are dependent on a number of factors, such as sample preparation and instrument geometry, peak positions are relatively insensitive to experimental details.

Figure 6:
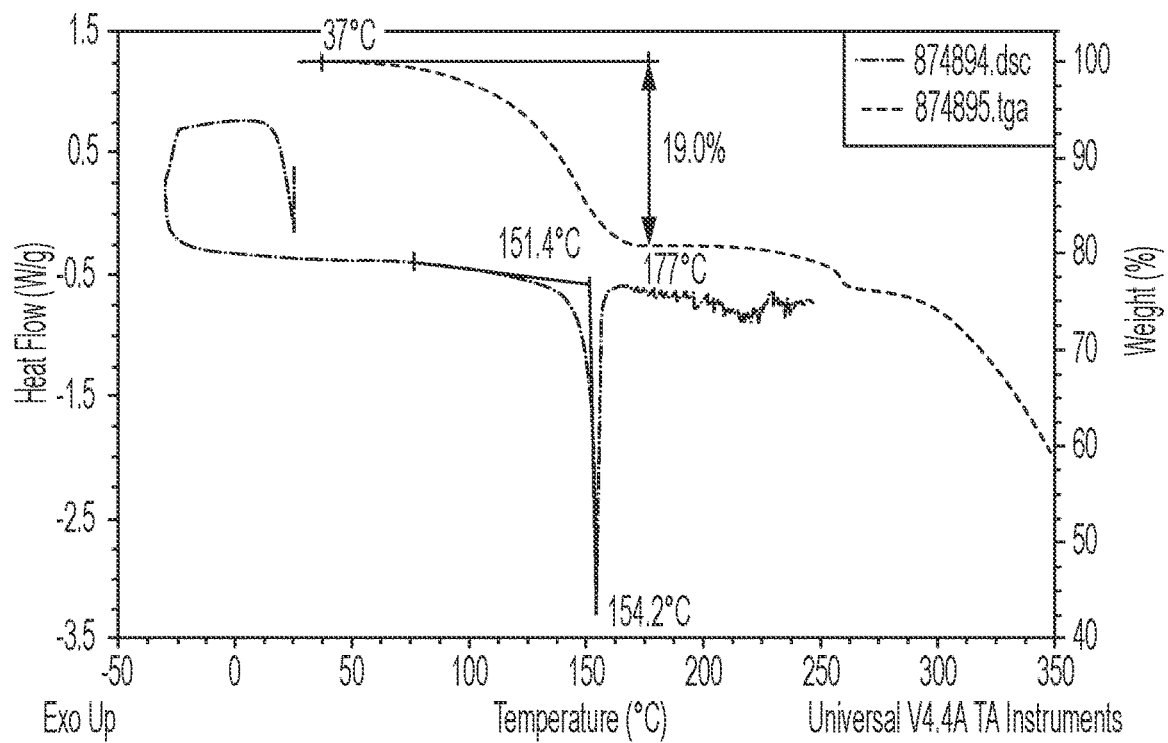
FIG. 6 depicts an overlay of a differential scanning calorimetry ("DSC") thermograph and a thermogravimetric analysis ("TGA") trace of the crystalline diethylamine salt form A of AMG 176 indicating a Tm of 151° C. and showing 19.0% weight loss from 37-177° C.

Differential scanning calorimetry (DSC) thermographs were obtained, as set forth in the Examples, for the crystalline diethylamine salt form A of AMG 176. The DSC curve indicates an endothermic transition at 151° C.±3° C. Thus, in some embodiments, the crystalline diethylamine salt form A of AMG 176 can be characterized by a DSC thermograph having a transition endotherm with an onset of 148° C. to 154° C. For example, in some embodiments the crystalline diethylamine salt form A of AMG 176 is characterized by DSC, as shown in FIG. 6.

The crystalline diethylamine salt form A of AMG 176 can be characterized by thermogravimetric analysis (TGA). Thus, the crystalline diethylamine salt form A of AMG 176 can be characterized by a weight loss in a range of about 19.0% weight loss from 37-111° C. In some embodiments, the crystalline diethylamine salt form A of AMG 176 has a thermogravimetric analysis substantially as depicted in FIG. 6, wherein by "substantially" is meant that the reported TGA features can vary by ±5° C.

Figure 7:
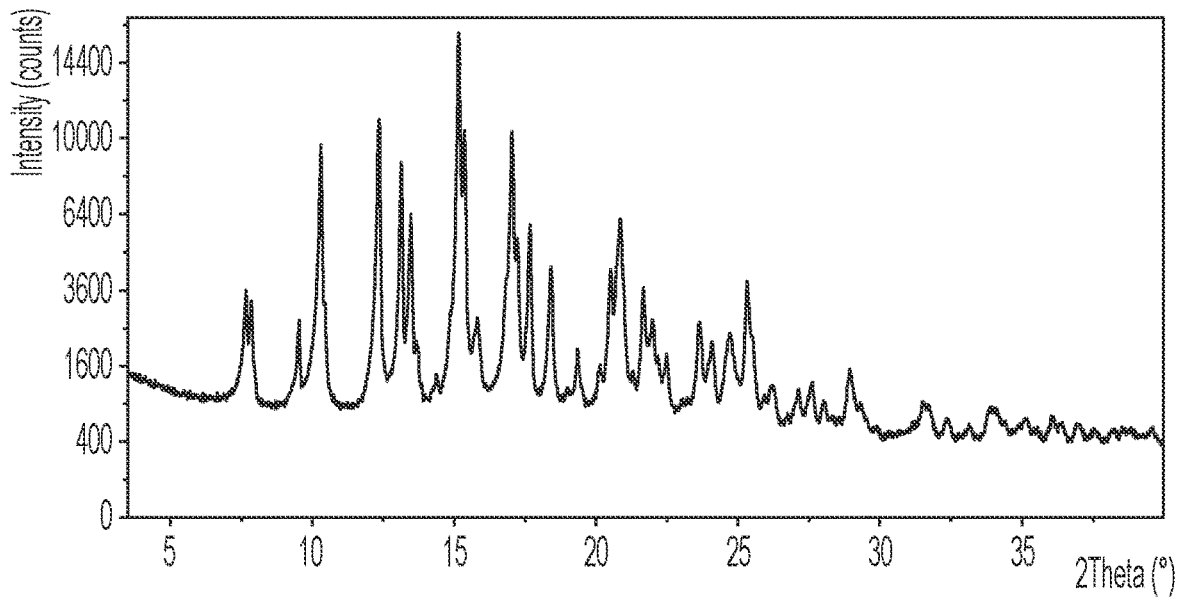
FIG. 7 depicts an X-ray powder diffraction ("XRPD") pattern of the crystalline diethylamine salt form B of AMG 176.

Diethylamine Salt Form B (Diethylamine Salt Anhydrous): The crystalline diethylamine salt form B of AMG 176 can be characterized by an X-ray powder diffraction pattern, obtained as set forth in the Examples, for example, an X-ray powder diffraction pattern substantially as shown in FIG. 7, wherein by "substantially" is meant that the reported peaks can vary by ±0.2°. It is well known in the field of XRPD that while relative peak heights in spectra are dependent on a number of factors, such as sample preparation and instrument geometry, peak positions are relatively insensitive to experimental details.

Figure 8:
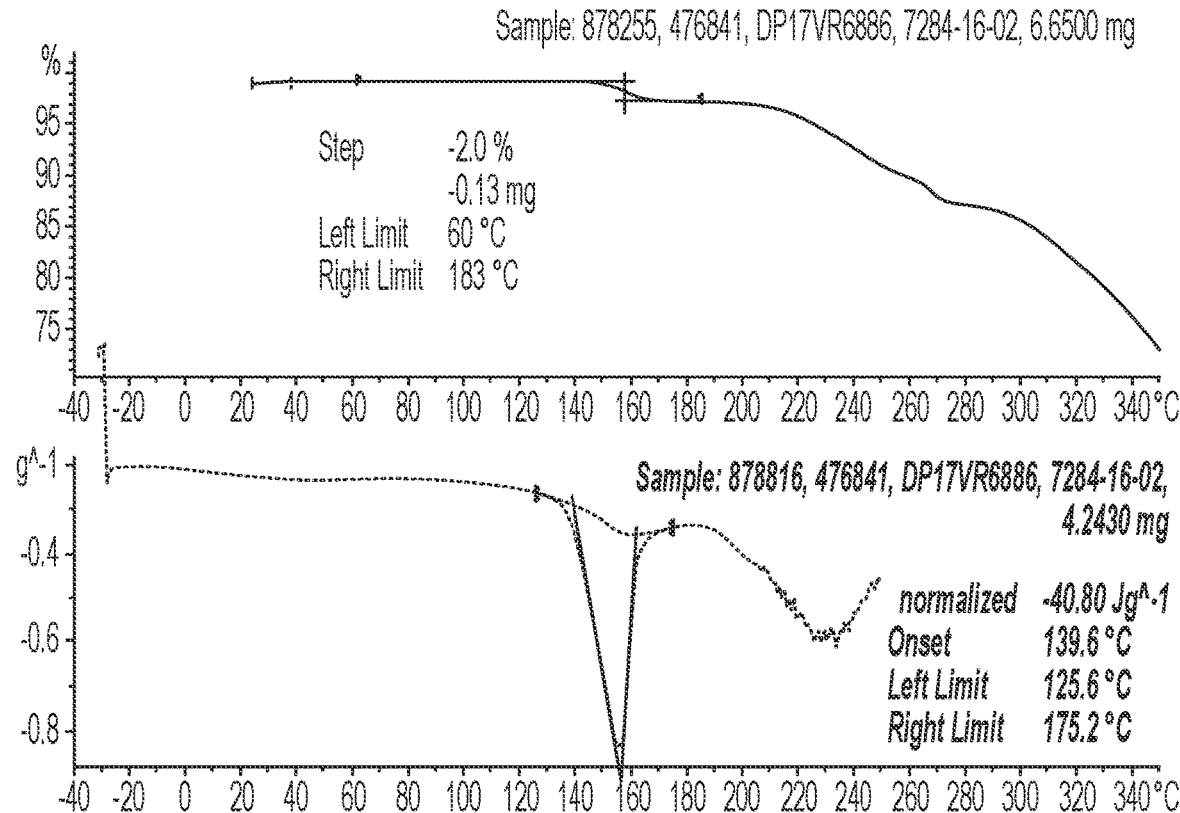
FIG. 8 depicts an overlay of a a differential scanning calorimetry ("DSC") thermograph and a thermogravimetric analysis ("TGA") trace of the crystalline diethylamine salt form B of AMG 176 indicating a Tm of 140° C. and showing 2% weight loss from 60-183° C.

Differential scanning calorimetry (DSC) thermographs were obtained, as set forth in the Examples, for the crystalline diethylamine salt form B of AMG 176. The DSC curve indicates an endothermic transition at 140° C.±3° C. Thus, in some embodiments, the crystalline diethylamine salt form B of AMG 176 can be characterized by a DSC thermograph having a transition endotherm with an onset of 140° C. to 260° C. For example, in some embodiments the crystalline diethylamine salt form B of AMG 176 is characterized by DSC, as shown in FIG. 8.

The crystalline diethylamine salt form B of AMG 176 can be characterized by thermogravimetric analysis (TGA). Thus, the crystalline diethylamine salt form B of AMG 176 can be characterized by a weight loss in a range of about 2% weight loss from 60-183° C. In some embodiments, the crystalline diethylamine salt form B of AMG 176 has a thermogravimetric analysis substantially as depicted in FIG. 8, wherein by "substantially" is meant that the reported TGA features can vary by ±5° C.

Figure 9:
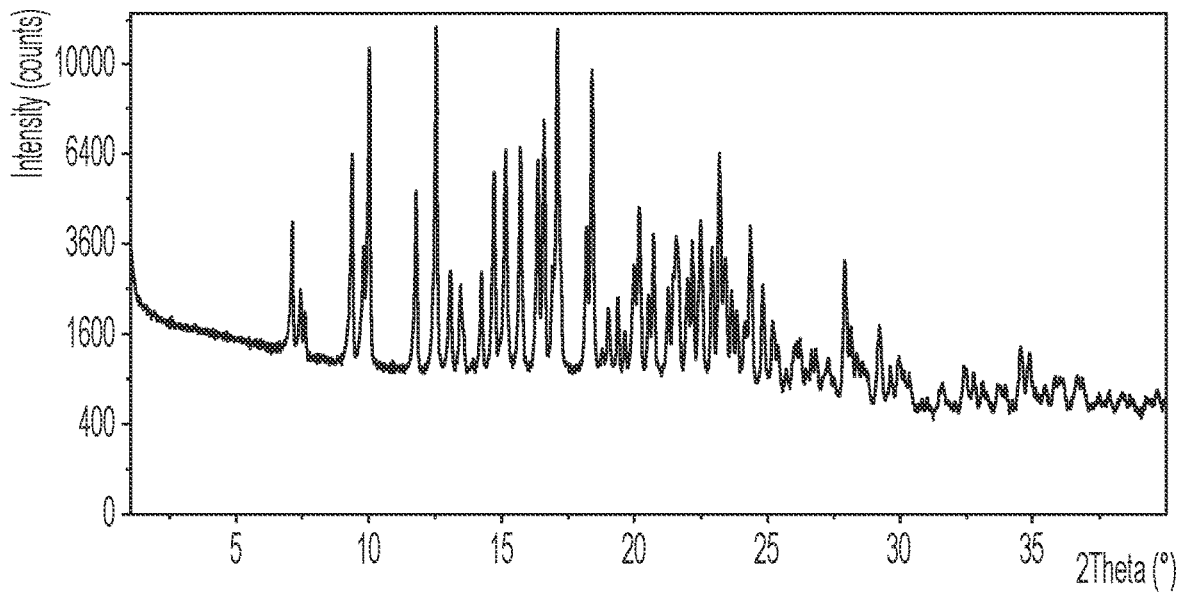
FIG. 9 depicts an X-ray powder diffraction ("XRPD") pattern of the crystalline diethanolamine salt toluene solvate of AMG 176.

Diethanolamine Salt Toluene Solvate: The crystalline diethanolamine salt toluene solvate of AMG 176 can be characterized by an X-ray powder diffraction pattern, obtained as set forth in the Examples, for example, an X-ray powder diffraction pattern substantially as shown in FIG. 9, wherein by "substantially" is meant that the reported peaks can vary by ±0.2°. It is well known in the field of XRPD that while relative peak heights in spectra are dependent on a number of factors, such as sample preparation and instrument geometry, peak positions are relatively insensitive to experimental details.

Figure 10:
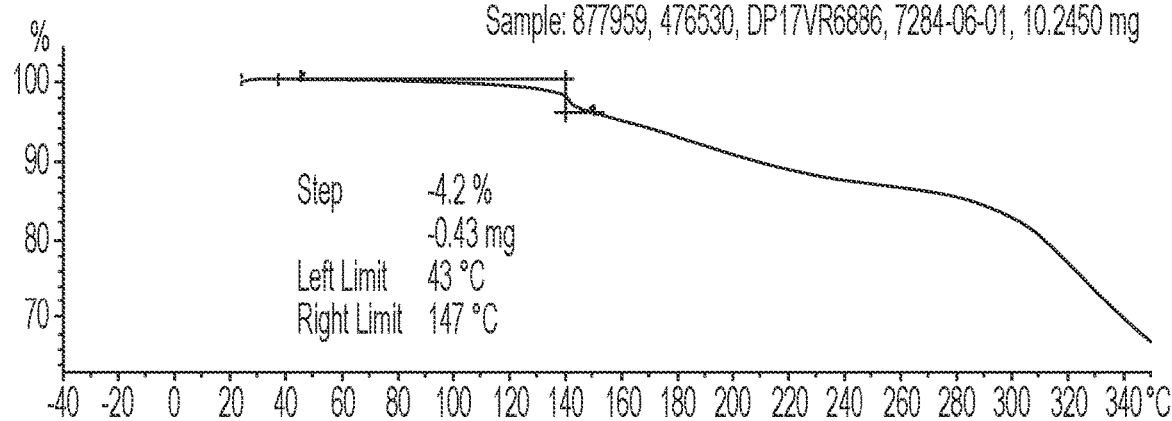
FIG. 10 depicts an overlay of a differential scanning calorimetry ("DSC") thermograph and athermogravimetric analysis ("TGA") trace of the crystalline diethanolamine salt toluene solvate of AMG 176 indicating a Tm of 134° C. and showing 4.2% weight loss from 43-147° C.
Figure 10:
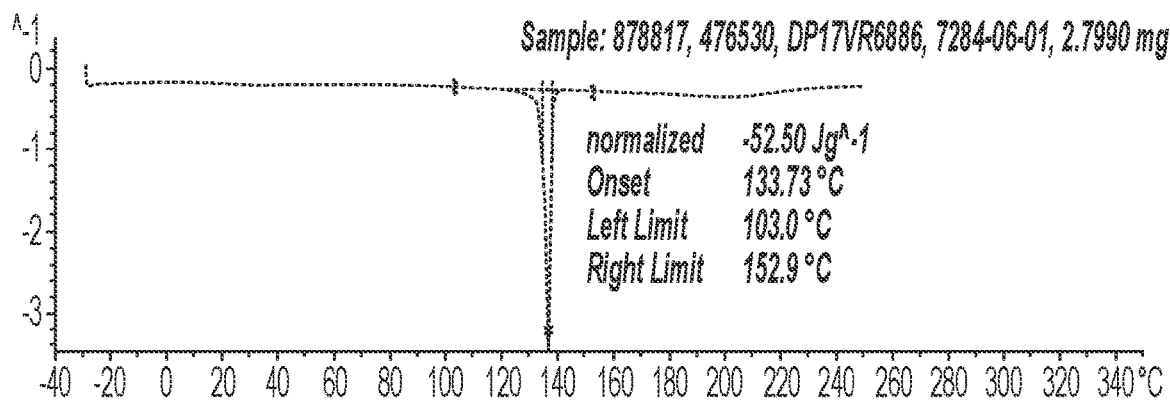

Differential scanning calorimetry (DSC) thermographs were obtained, as set forth in the Examples, for the crystalline diethanolamine salt toluene solvate of AMG 176. The DSC curve indicates an endothermic transition at 134° C.±3° C. Thus, in some embodiments, the crystalline diethanolamine salt toluene solvate of AMG 176 can be characterized by a DSC thermograph having a transition endotherm with an onset of 134° C. to 230° C. For example, in some embodiments the crystalline diethanolamine salt tolene solvate of AMG 176 is characterized by DSC, as shown in FIG. 10.

The crystalline diethanolamine salt toluene solvate of AMG 176 can be characterized by thermogravimetric analysis (TGA). Thus, the crystalline diethanolamine salt toluene solvate of AMG 176 can be characterized by a weight loss in a range of about 4.2% weight loss from 43-147° C. In some embodiments, the crystalline diethanolamine salt toluene solvate of AMG 176 has a thermogravimetric analysis substantially as depicted in FIG. 10, wherein by "substantially" is meant that the reported TGA features can vary by ±5° C.

Figure 11:
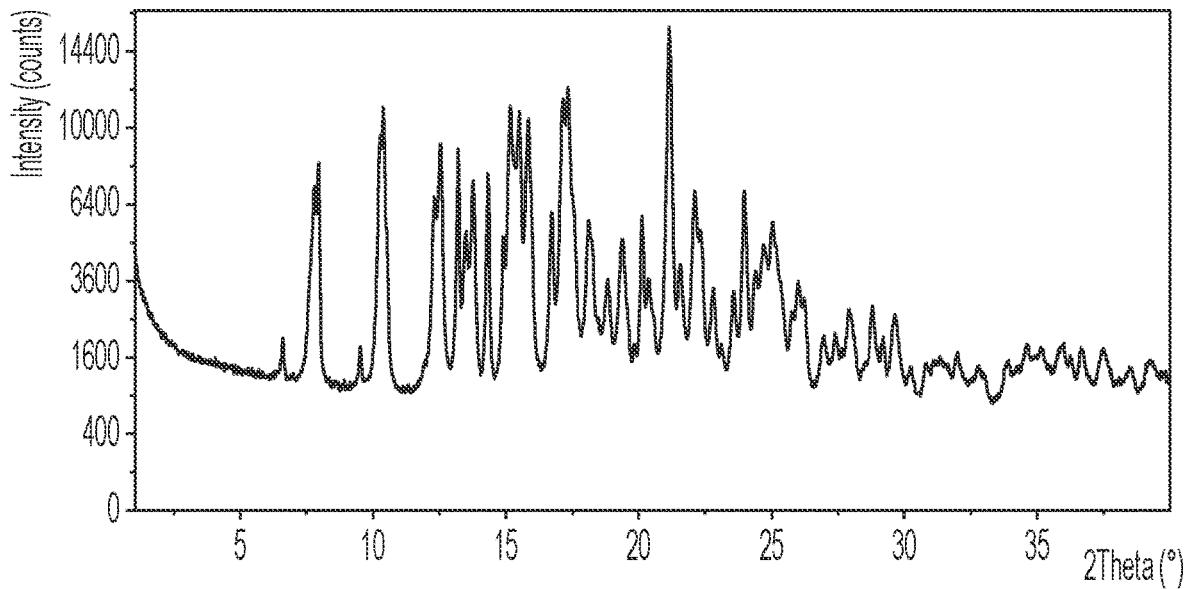
FIG. 11 depicts an X-ray powder diffraction ("XRPD") pattern of the crystalline diethanolamine salt anhydrous form of AMG 176.

Diethanolamine Salt Anhydrous Form: The crystalline diethanolamine salt anhydrous form of AMG 176 can be characterized by an X-ray powder diffraction pattern, obtained as set forth in the Examples, for example, an X-ray powder diffraction pattern substantially as shown in FIG. 11, wherein by "substantially" is meant that the reported peaks can vary by ±0.2°. It is well known in the field of XRPD that while relative peak heights in spectra are dependent on a number of factors, such as sample preparation and instrument geometry, peak positions are relatively insensitive to experimental details.

Figure 12:
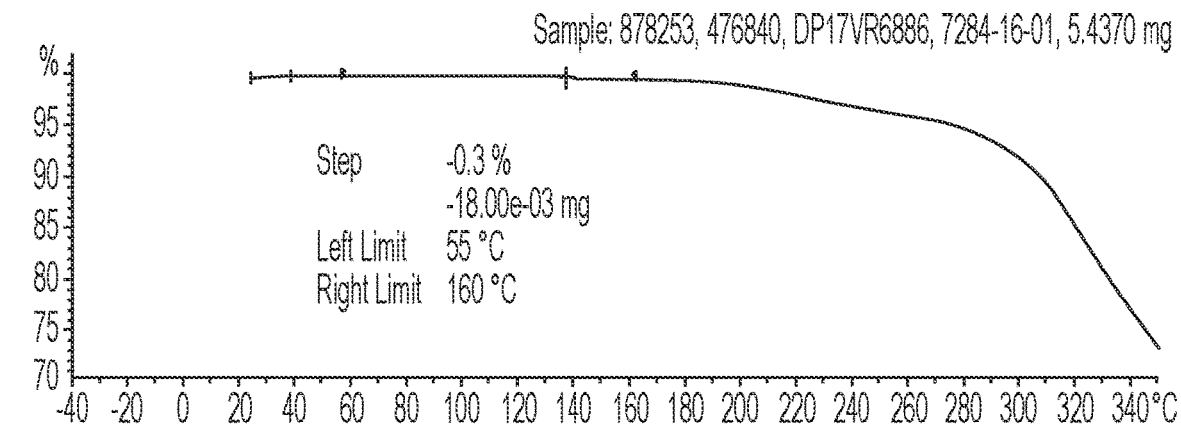
FIG. 12 depicts an overlay of a a differential scanning calorimetry ("DSC") thermograph and a thermogravimetric analysis ("TGA") trace of the crystalline diethanolamine salt anhydrous form of AMG 176 indicating a Tm of 126° C. and showing 0.3% weight loss from 55-160° C.
Figure 12:
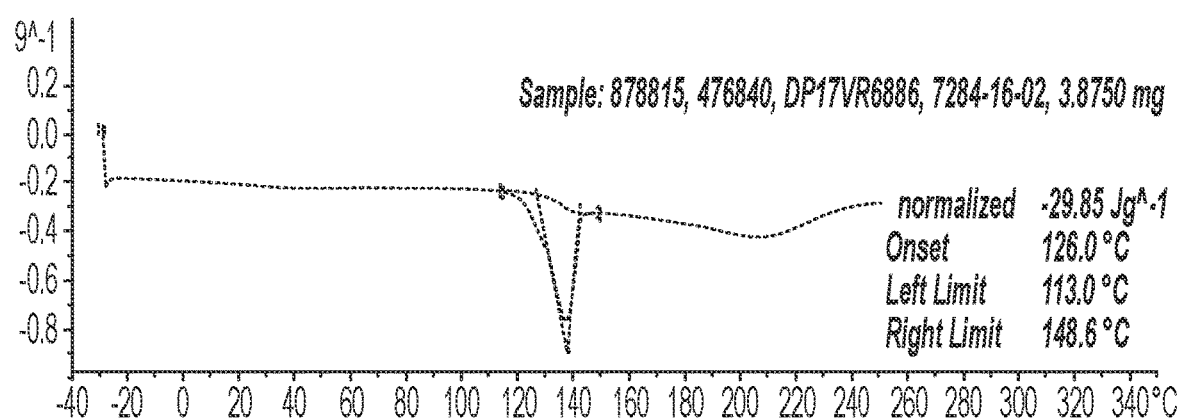

Differential scanning calorimetry (DSC) thermographs were obtained, as set forth in the Examples, for the crystalline diethanolamine salt anhydrous form of AMG 176. The DSC curve indicates an endothermic transition at 126° C.±3° C. Thus, in some embodiments, the crystalline diethanolamine salt anhydrous form of AMG 176 can be characterized by a DSC thermograph having a transition endotherm with an onset of 126° C. to 240° C. For example, in some embodiments the crystalline diethanolamine salt anhydrous form of AMG 176 is characterized by DSC, as shown in FIG. 12.

The crystalline diethanolamine salt anhydrous form of AMG 176 can be characterized by thermogravimetric analysis (TGA). Thus, the crystalline diethanolamine salt anhydrous form of AMG 176 can be characterized by a weight loss in a range of about 0.3% weight loss from 55-160° C. In some embodiments, the crystalline diethanolamine salt anhydrous form of AMG 176 has a thermogravimetric analysis substantially as depicted in FIG. 12, wherein by "substantially" is meant that the reported TGA features can vary by ±5° C.

Figure 13:
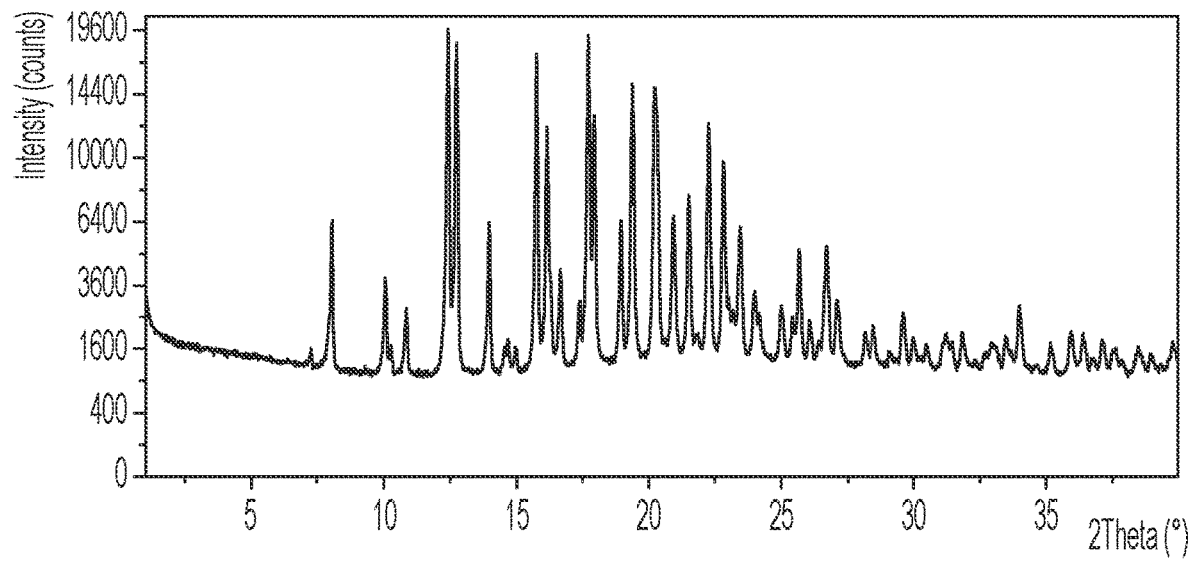
FIG. 13 depicts an X-ray powder diffraction ("XRPD") pattern of the crystalline 1,4-dioxane solvate AMG 176.

1,4-Dioxane Solvate Form: The crystalline 1,4-dioxane solvate form of AMG 176 can be characterized by an X-ray powder diffraction pattern, obtained as set forth in the Examples, having peaks at 12.4, 12.8, 15.8, and 17.7±0.2° 2θ using Cu Kα radiation, optionally further characterized by additional peaks at 18.0, 19.4, 20.2, and 22.3±0.2° 2θ using Cu Kα radiation, and/or additional peaks at 8.1, 10.1, 14.0, 16.2, 16.7, 17.4, 19.0, 20.3, 20.9, 21.5, 22.8, 23.5, 24.0, 25.0, 25.7, 26.7, and 27.1±0.2° 2θ using Cu Kα radiation. In some embodiments, the crystalline 1,4-dioxane solvate form of AMG 176 has an X-ray powder diffraction pattern substantially as shown in FIG. 13, wherein by "substantially" is meant that the reported peaks can vary by ±0.2°. It is well known in the field of XRPD that while relative peak heights in spectra are dependent on a number of factors, such as sample preparation and instrument geometry, peak positions are relatively insensitive to experimental details.

Figure 14:
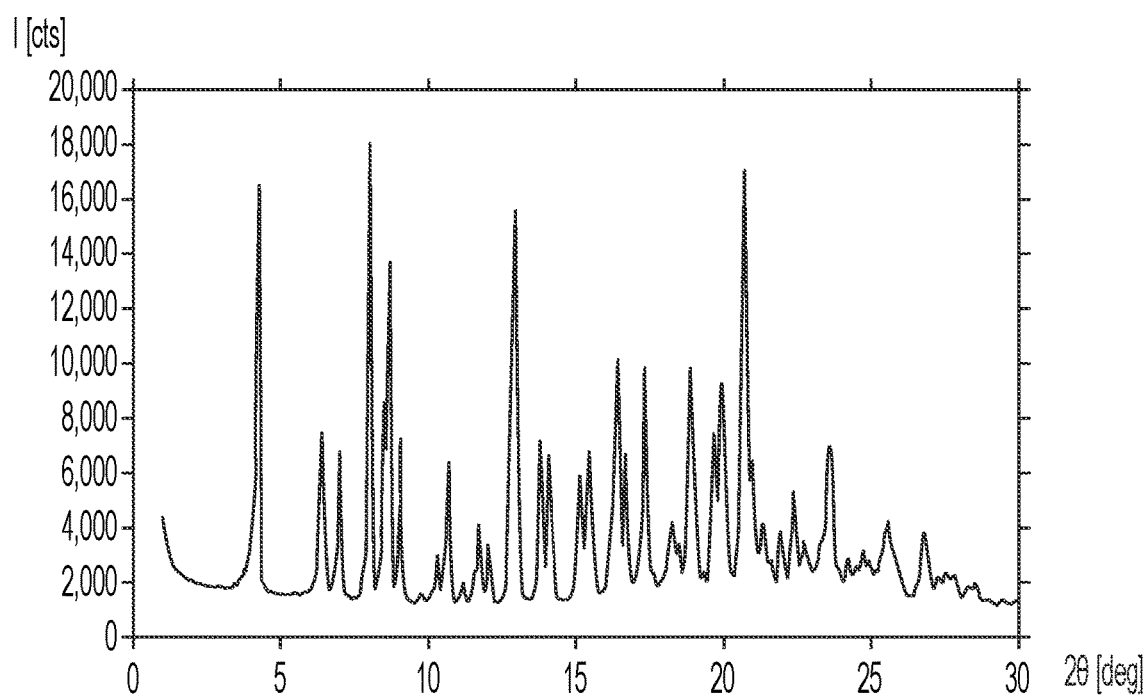
FIG. 14 depicts an X-ray powder diffraction ("XRPD") pattern of the crystalline imidazole salt form A of AMG 176.

Imidazole Salt Acetone Solvate Form: The crystalline imidazole salt acetone solvate form of AMG 176 can be characterized by an X-ray powder diffraction pattern, obtained as set forth in the Examples, having peaks at 4.2, 8.1, and 20.7±0.2° 2θ using Cu Kα radiation, optionally further characterized by additional peaks at 8.7, 12.9, 16.4, and 17.4±0.2° 2θ using Cu Kα radiation, and/or additional peaks at 6.4, 7.0, 8.5, 9.1, 10.7, 13.8, 14.1, 15.1, 15.5, 16.7, 18.8, 19.7, 19.9, 21.0, 22.4, and 23.6±0.2° 2θ using Cu Kα radiation. In some embodiments, the crystalline imidazole salt acetone solvate form of AMG 176 has an X-ray powder diffraction pattern substantially as shown in FIG. 14, wherein by "substantially" is meant that the reported peaks can vary by ±0.2°. It is well known in the field of XRPD that while relative peak heights in spectra are dependent on a number of factors, such as sample preparation and instrument geometry, peak positions are relatively insensitive to experimental details.

Figure 15:
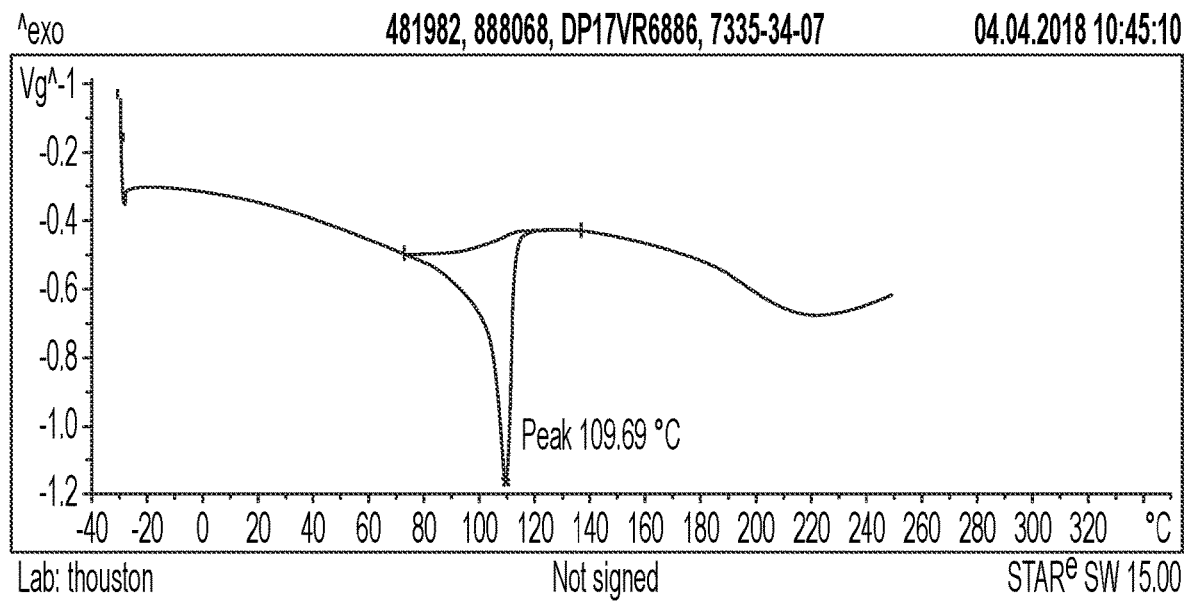
FIG. 15 depicts a differential scanning calorimetry ("DSC") thermograph of the crystalline imidazole salt form A of AMG 176 indicating a Tm of 110° C.

Differential scanning calorimetry (DSC) thermographs were obtained, as set forth in the Examples, for the crystalline imidazole salt acetone solvate form of AMG 176. The DSC curve indicates an endothermic transition at 110° C.±3° C. For example, in some embodiments the crystalline imidazole salt acetone solvate form of AMG 176 is characterized by DSC, as shown in FIG. 15.

Figure 16:
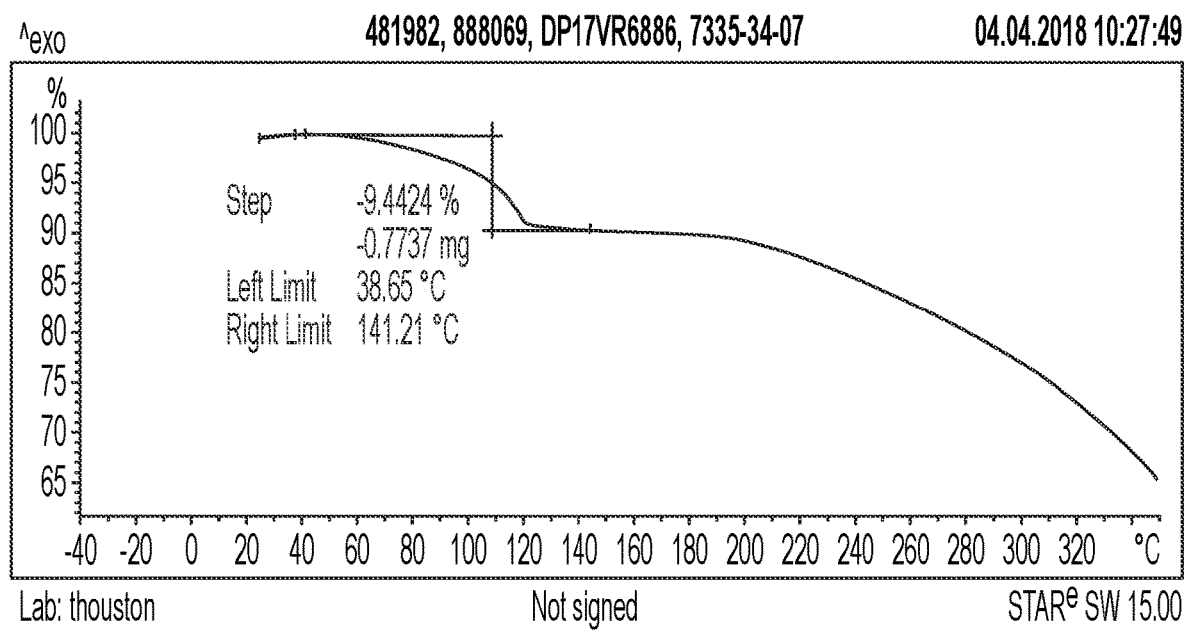
FIG. 16 depicts a thermogravimetric analysis ("TGA") trace of the crystalline imidazole salt form A of AMG 176 showing 9% weight loss.

The crystalline imidazole salt acetone solvate form of AMG 176 can be characterized by thermogravimetric analysis (TGA). Thus, the crystalline imidazole salt acetone solvate form of AMG 176 can be characterized by a weight loss in a range of about 9% weight loss. In some embodiments, the crystalline imidazole salt acetone solvate form of AMG 176 has a thermogravimetric analysis substantially as depicted in FIG. 16, wherein by "substantially" is meant that the reported TGA features can vary by ±5° C.

Figure 17:
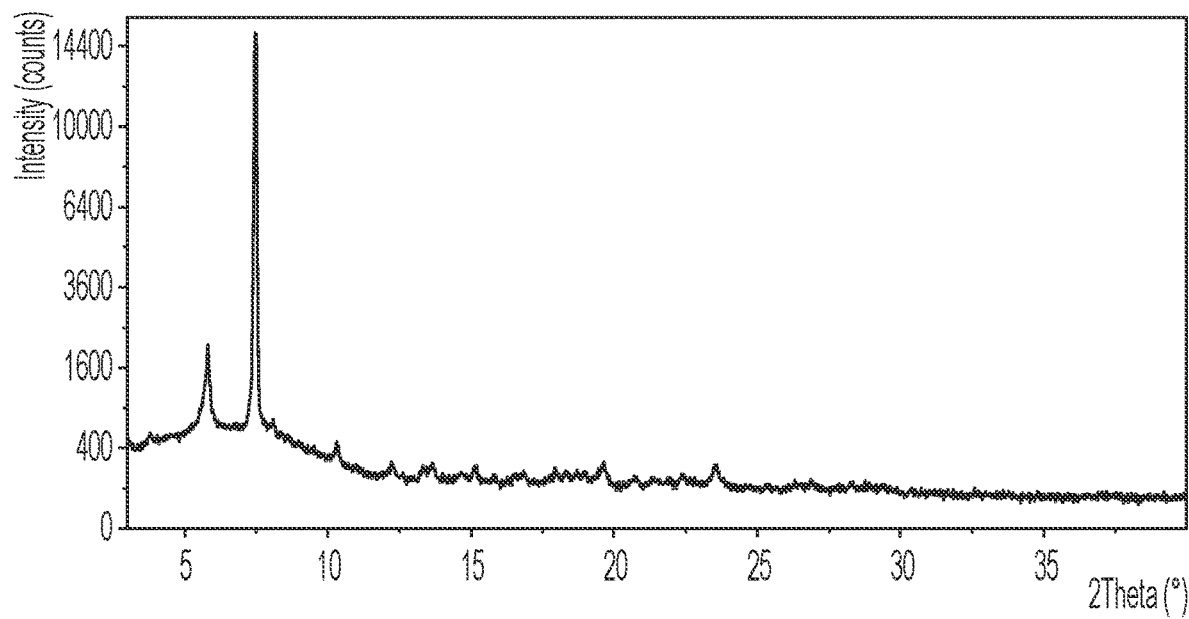
FIG. 17 depicts an X-ray powder diffraction ("XRPD") pattern of the crystalline hemi magnesium salt dihydrate form of AMG 176.

Hemi Magnesium Salt Dihydrate Form: The crystalline magnesium salt hydrate form of AMG 176 can be characterized by an X-ray powder diffraction pattern, obtained as set forth in the Examples, having peaks at 3.8, 5.8, and 7.5±0.2° 2θ using Cu Kα radiation, optionally further characterized by additional peaks at 10.3, 12.3, 13.7, 15.1, 16.7, 19.7, 20.7, and 23.5±0.2° 2θ using Cu Kα radiation. In some embodiments, the crystalline magnesium salt hydrate form of AMG 176 has an X-ray powder diffraction pattern substantially as shown in FIG. 17, wherein by "substantially" is meant that the reported peaks can vary by ±0.2°. It is well known in the field of XRPD that while relative peak heights in spectra are dependent on a number of factors, such as sample preparation and instrument geometry, peak positions are relatively insensitive to experimental details.

Figure 18:
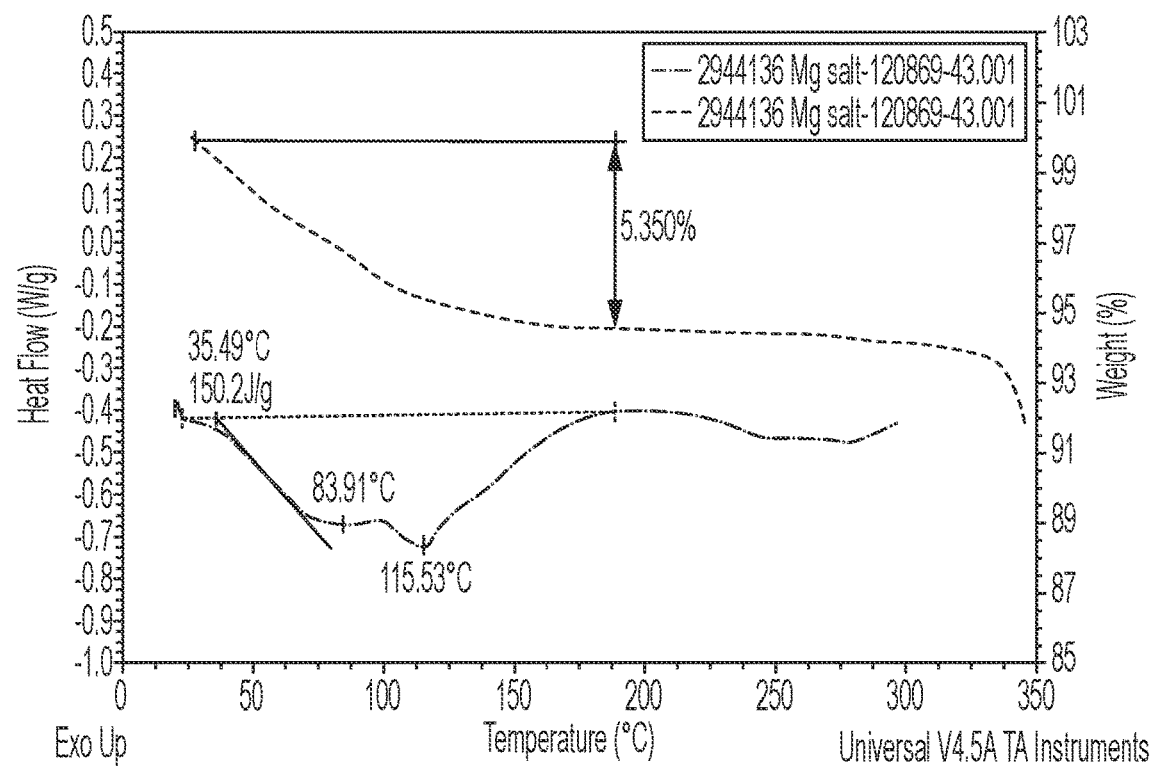
FIG. 18 depicts an overlay of a differential scanning calorimetry ("DSC") thermograph and a thermogravimetric analysis ("TGA") trace of the crystalline hemi magnesium salt dihydrate form of AMG 176 indicating endothermic transitions at 84 and 115° C. and showing 5.4% weight loss.

Differential scanning calorimetry (DSC) thermographs were obtained, as set forth in the Examples, for the crystalline hemi magnesium salt dihydrate form of AMG 176. The DSC curve indicates endothermic transitions at 84° C.±3° C. and 115° C.±3° C. For example, in some embodiments the crystalline hemi magnesium salt dihydrate form of AMG 176 is characterized by DSC, as shown in FIG. 18.

The crystalline hemi magnesium salt dihydrate form of AMG 176 can be characterized by thermogravimetric analysis (TGA). Thus, the crystalline hemi magnesium salt dihydrate form of AMG 176 can be characterized by a weight loss in a range of about 5.4% weight loss. In some embodiments, the crystalline hemi magnesium salt hydrate form of AMG 176 has a thermogravimetric analysis substantially as depicted in FIG. 18, wherein by "substantially" is meant that the reported TGA features can vary by ±5° C.

Figure 19:
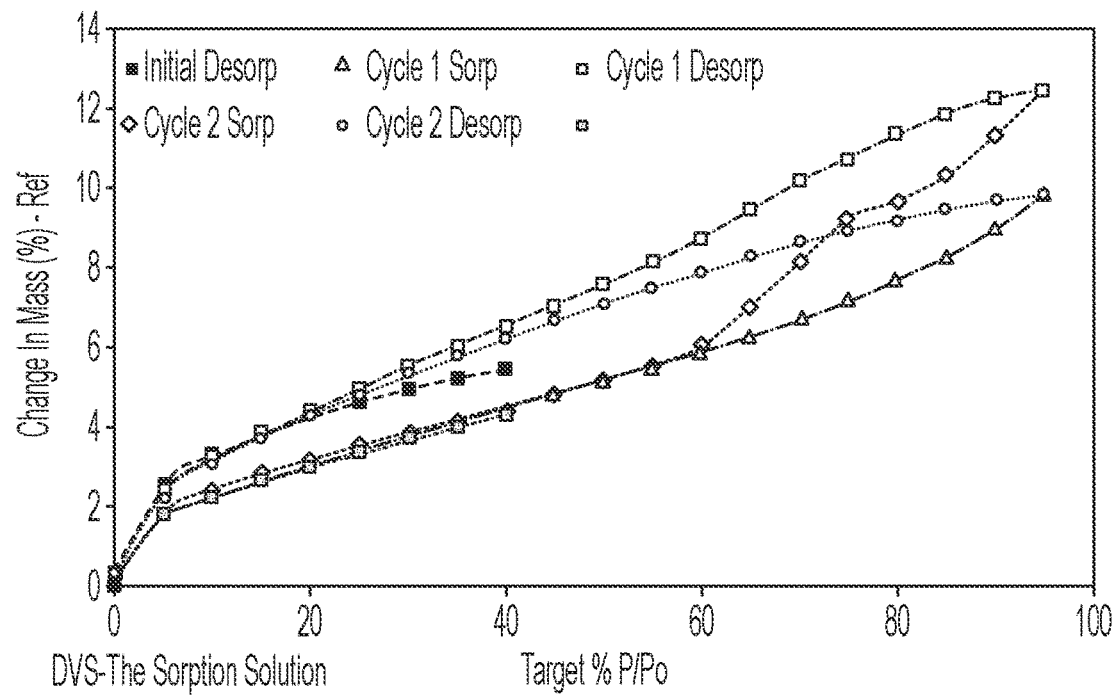
FIG. 19 depicts a moisture sorption profile (DVS) of the crystalline hemi magnesium salt dihydrate form of AMG 176 showing weight gain of about 12% by 95% relative humidity.

The crystalline hemi magnesium salt dihydrate form of AMG 176 can be characterized by a moisture sorption profile. For example, in some embodiments, the crystalline hemi magnesium salt dihydrate form of AMG 176 is characterized by the moisture sorption profile as shown in FIG. 19, showing a weight gain of about 12% by 95% relative humidity.

Figure 20:
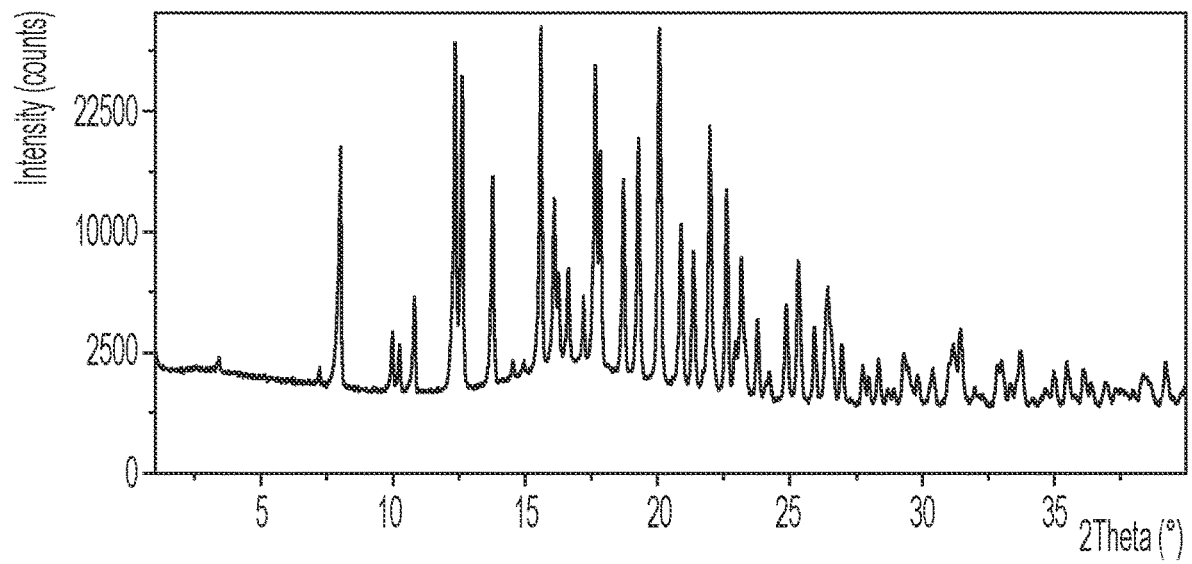
FIG. 20 depicts an X-ray powder diffraction ("XRPD") pattern of the crystalline methyl tert-butyl ether solvate of AMG 176.

Methyl tert-Butyl Ether Solvate Form: The crystalline methyl tert-butyl ether solvate form of AMG 176 can be characterized by an X-ray powder diffraction pattern, obtained as set forth in the Examples, having peaks at 12.4, 15.6, and 20.1±0.2° 2θ using Cu Kα radiation, optionally further characterized by additional peaks at 8.0, 12.6, 17.7, 17.9, 19.3, and 22.0±0.2° 2θ using Cu Kα radiation, and/or additional peaks at 10.8, 13.8, 16.1, 16.3, 16.6, 17.2, 18.7, 20.9, 21.4, 22.6, 23.2, 24.9, 25.3, 26.3, and 26.4±0.2° 2θ using Cu Kα radiation. In some embodiments, the crystalline methyl tert-butyl ether solvate form of AMG 176 has an X-ray powder diffraction pattern substantially as shown in FIG. 20, wherein by "substantially" is meant that the reported peaks can vary by ±0.2°. It is well known in the field of XRPD that while relative peak heights in spectra are dependent on a number of factors, such as sample preparation and instrument geometry, peak positions are relatively insensitive to experimental details.

Figure 21:
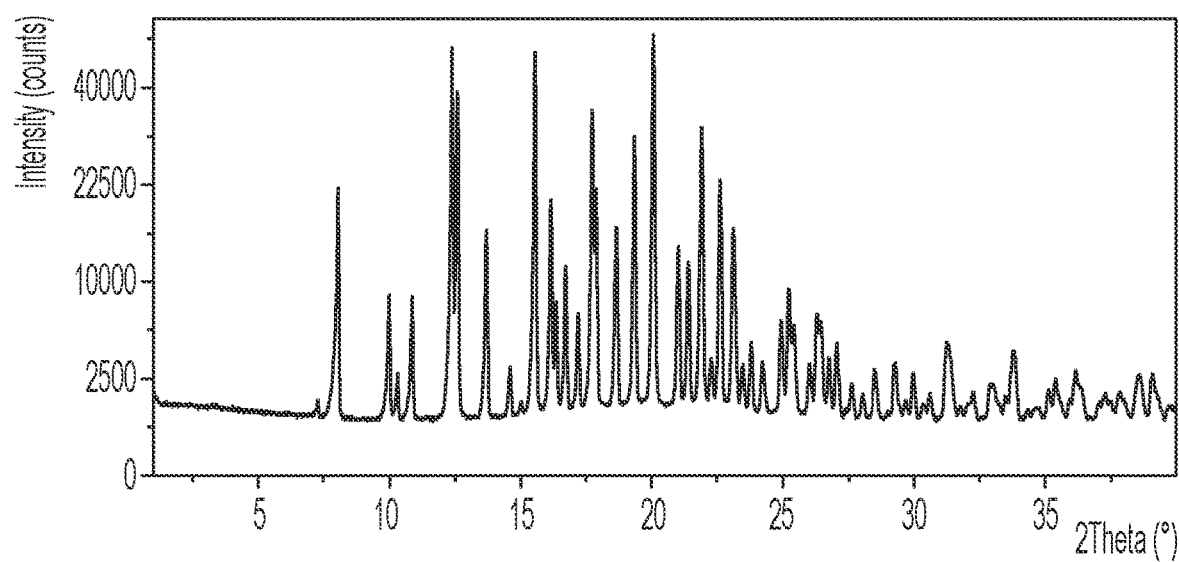
FIG. 21 depicts an X-ray powder diffraction ("XRPD") pattern of the crystalline 2-methyltetrahydrofuran solvate of AMG 176.

2-Methyltetrahydrofuran Solvate Form: The crystalline 2-methyltetrahydrofuran solvate form of AMG 176 can be characterized by an X-ray powder diffraction pattern, obtained as set forth in the Examples, having peaks at 12.4, 15.6, and 20.1±0.2° 2θ using Cu Kα radiation, optionally further characterized by additional peaks at 12.6, 17.8, 19.4, and 21.9±0.2° 2θ using Cu Kα radiation, and/or additional peaks at 8.1, 13.7, 16.2, 16.7, 17.9, 18.7, 21.0, 21.4, 22.6, and 23.1±0.2° 2θ using Cu Kα radiation. In some embodiments, the crystalline 2-methyltetrahydrofuran solvate form of AMG 176 has an X-ray powder diffraction pattern substantially as shown in FIG. 21, wherein by "substantially" is meant that the reported peaks can vary by ±0.2°. It is well known in the field of XRPD that while relative peak heights in spectra are dependent on a number of factors, such as sample preparation and instrument geometry, peak positions are relatively insensitive to experimental details.

Figure 22:
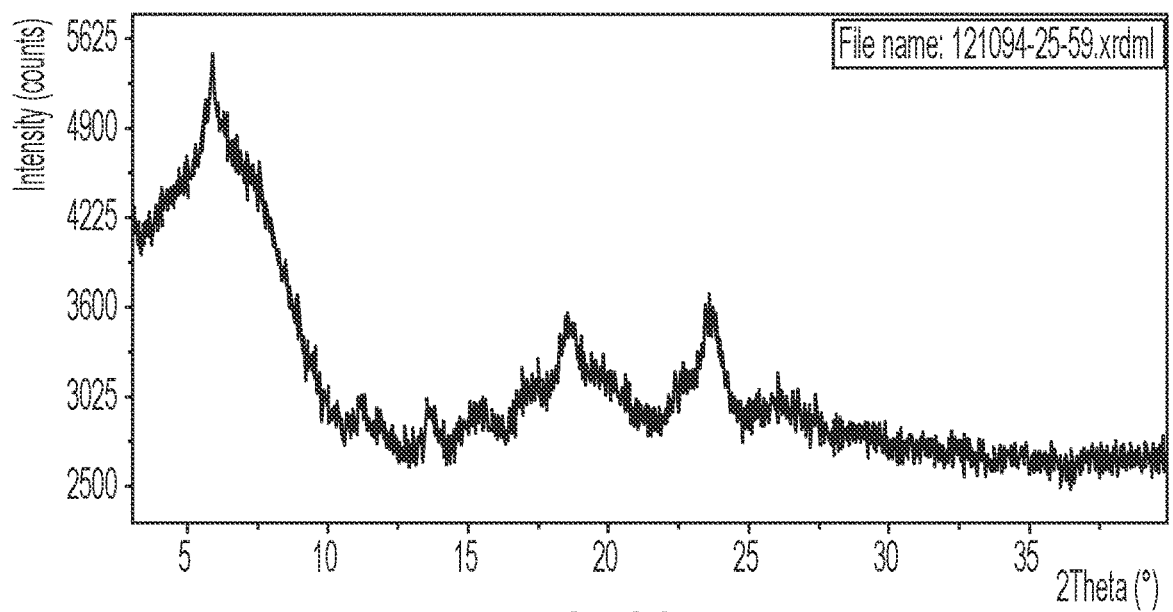
FIG. 22 depicts an X-ray powder diffraction ("XRPD") pattern of the crystalline potassium salt hydrate of AMG 176.

Potassium Salt Hydrate Form: The crystalline potassium salt hydrate form of AMG 176 can be characterized by an X-ray powder diffraction pattern, obtained as set forth in the Examples, having peaks at 5.9, 7.6, and 23.5±0.2° 2θ using Cu Kα radiation, optionally further characterized by additional peaks at 11.2, 13.6, 15.3, 16.9, 18.5, and 22.5±0.2° 2θ using Cu Kα radiation. In some embodiments, the crystalline potassium salt hydrate form of AMG 176 has an X-ray powder diffraction pattern substantially as shown in FIG. 22, wherein by "substantially" is meant that the reported peaks can vary by ±0.2°. It is well known in the field of XRPD that while relative peak heights in spectra are dependent on a number of factors, such as sample preparation and instrument geometry, peak positions are relatively insensitive to experimental details.

Figure 23:
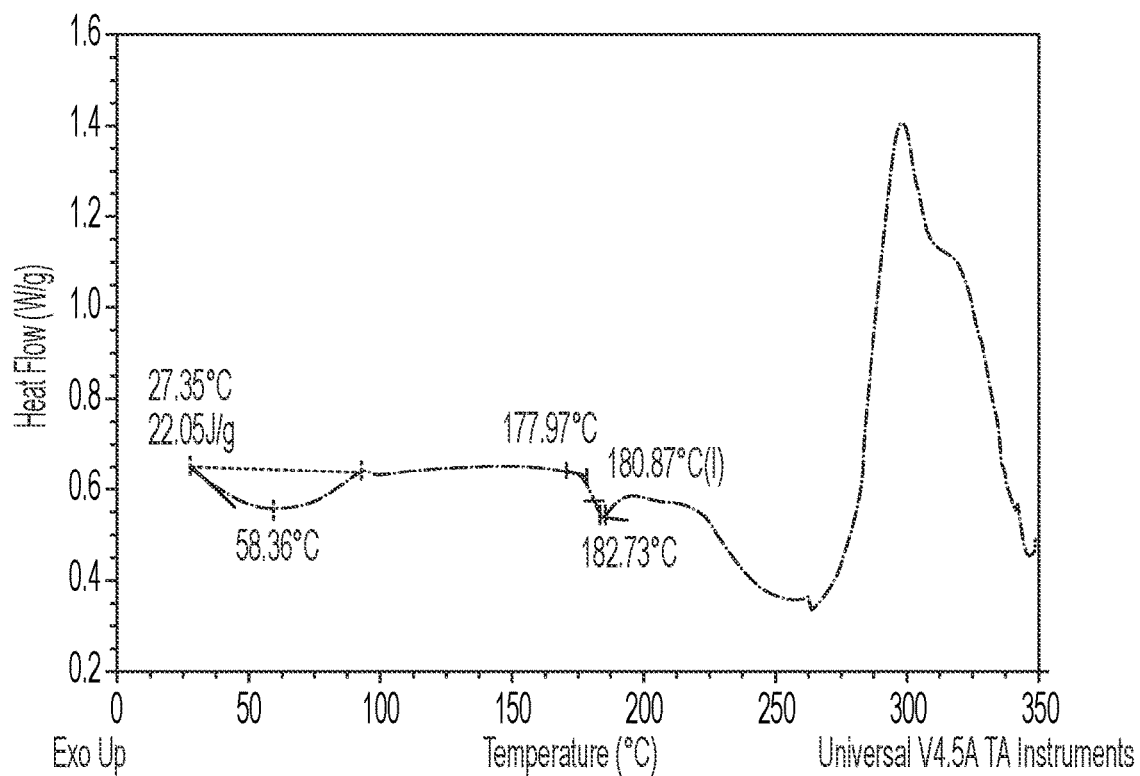
FIG. 23 depicts a differential scanning calorimetry ("DSC") thermograph of the crystalline potassium salt hydrate of AMG 176 indicating endothermic events at 58 and 182° C.

Differential scanning calorimetry (DSC) thermographs were obtained, as set forth in the Examples, for the crystalline potassium salt hydrate form of AMG 176. The DSC curve indicates endothermic events at 58° C.±3° C. and 182° C.±3° C. For example, in some embodiments the crystalline potassium hydrate salt form of AMG 176 is characterized by DSC, as shown in FIG. 23.

Figure 24:
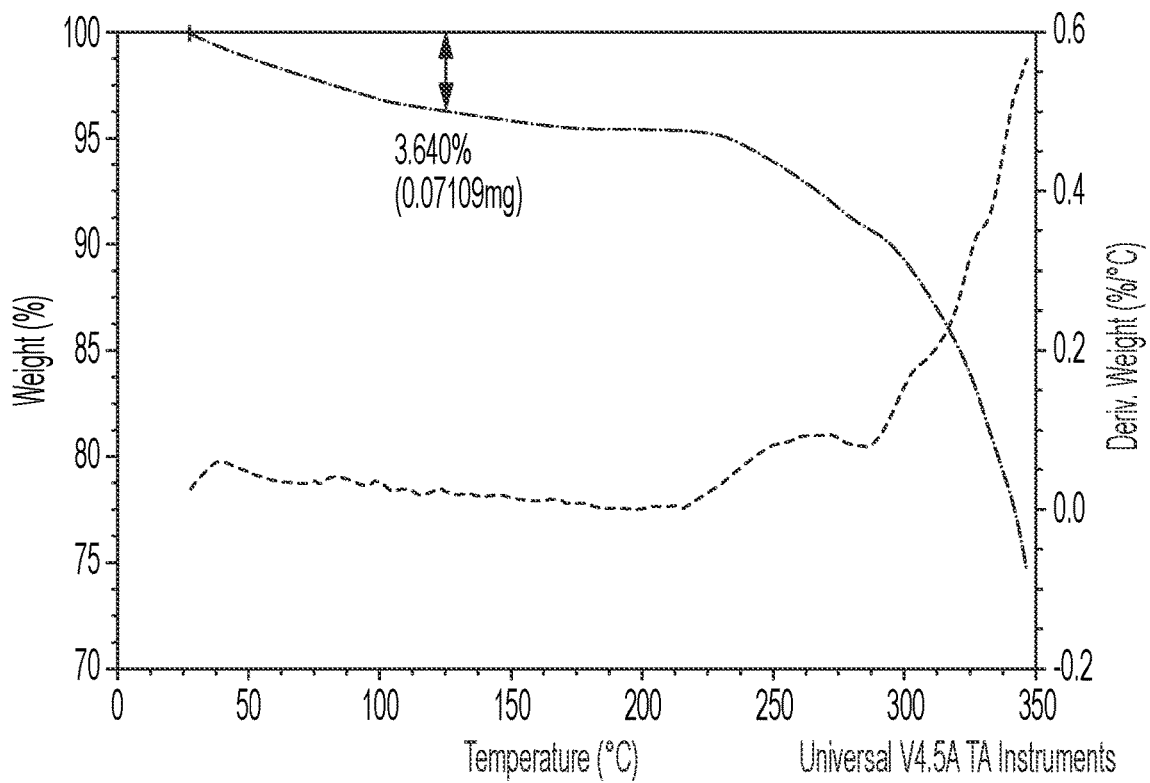
FIG. 24 depicts a thermogravimetric analysis ("TGA") trace of the crystalline potassium salt hydrate form of AMG 176 showing 3.6% weight loss.

The crystalline potassium salt hydrate form of AMG 176 can be characterized by thermogravimetric analysis (TGA). Thus, the crystalline potassium salt hydrate form of AMG 176 can be characterized by a weight loss in a range of about 3.6% weight loss. In some embodiments, the crystalline potassium salt hydrate of AMG 176 has a thermogravimetric analysis substantially as depicted in FIG. 24, wherein by "substantially" is meant that the reported TGA features can vary by ±5° C.

Figure 25:
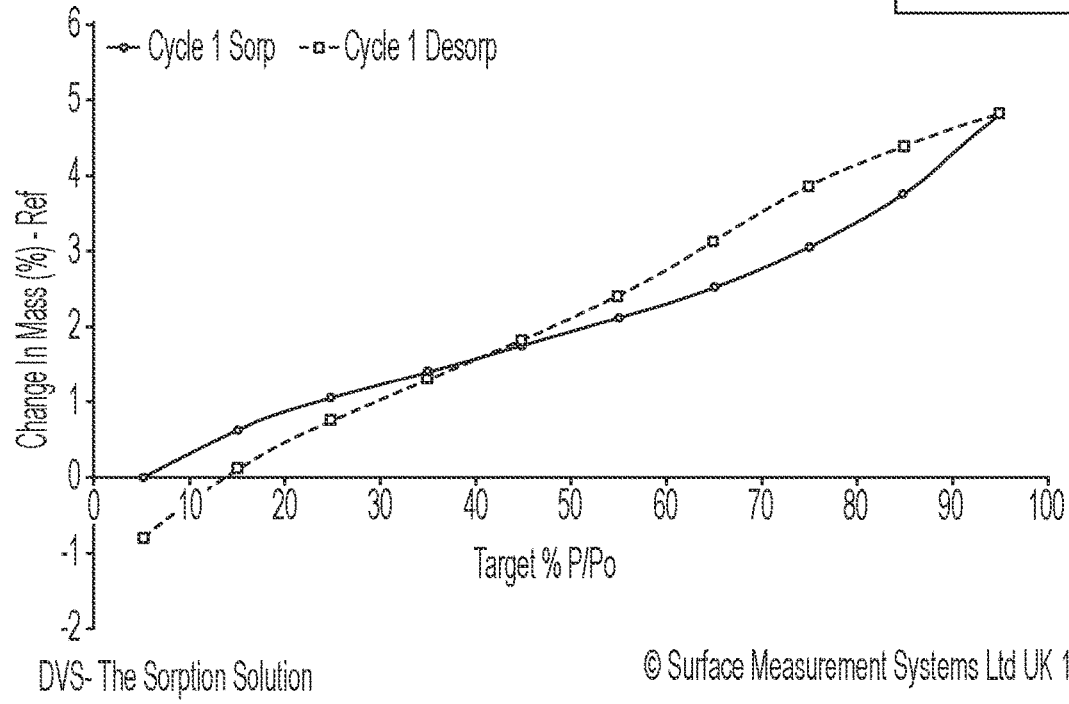
FIG. 25 depicts a moisture sorption profile (DVS) of the crystalline potassium salt hydrate form of AMG 176 showing weight gain of about 5% by 95% relative humidity, which is lost upon desorption.

The crystalline potassium salt hydrate form of AMG 176 can be characterized by a moisture sorption profile. For example, in some embodiments, the crystalline potassium salt hydrate form of AMG 176 is characterized by the moisture sorption profile as shown in FIG. 25, showing a weight gain of about 5% by 95% relative humidity, which is lost upon desorption.

Figure 26:
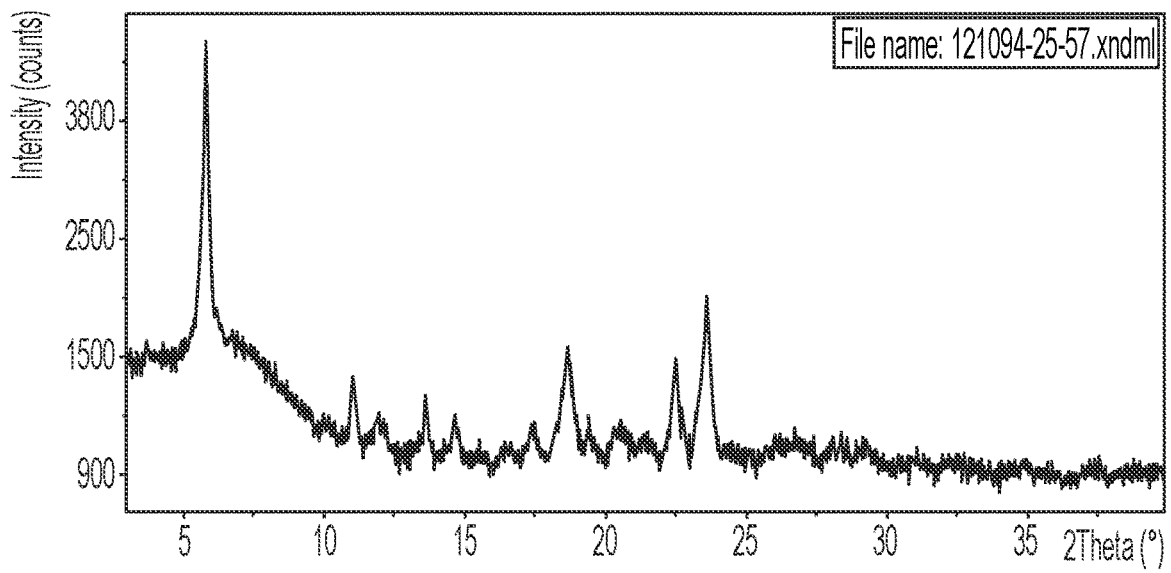
FIG. 26 depicts an X-ray powder diffraction ("XRPD") pattern of the crystalline potassium salt isopropanol solvate of AMG 176.

Potassium Salt Isopropanol Solvate Form: The crystalline potassium salt isopropanol solvate form of AMG 176 can be characterized by an X-ray powder diffraction pattern, obtained as set forth in the Examples, having peaks at 5.8, 18.7, 22.5, and 23.5±0.2° 2θ using Cu Kα radiation, optionally further characterized by additional peaks at 11.0, 12.0, 13.6, 14.7, 17.4, 19.4, 20.4, and 29.2±0.2° 2θ using Cu Kα radiation. In some embodiments, the crystalline potassium salt isopropanol solvate form of AMG 176 has an X-ray powder diffraction pattern substantially as shown in FIG. 26, wherein by "substantially" is meant that the reported peaks can vary by ±0.2°. It is well known in the field of XRPD that while relative peak heights in spectra are dependent on a number of factors, such as sample preparation and instrument geometry, peak positions are relatively insensitive to experimental details.

Figure 27:
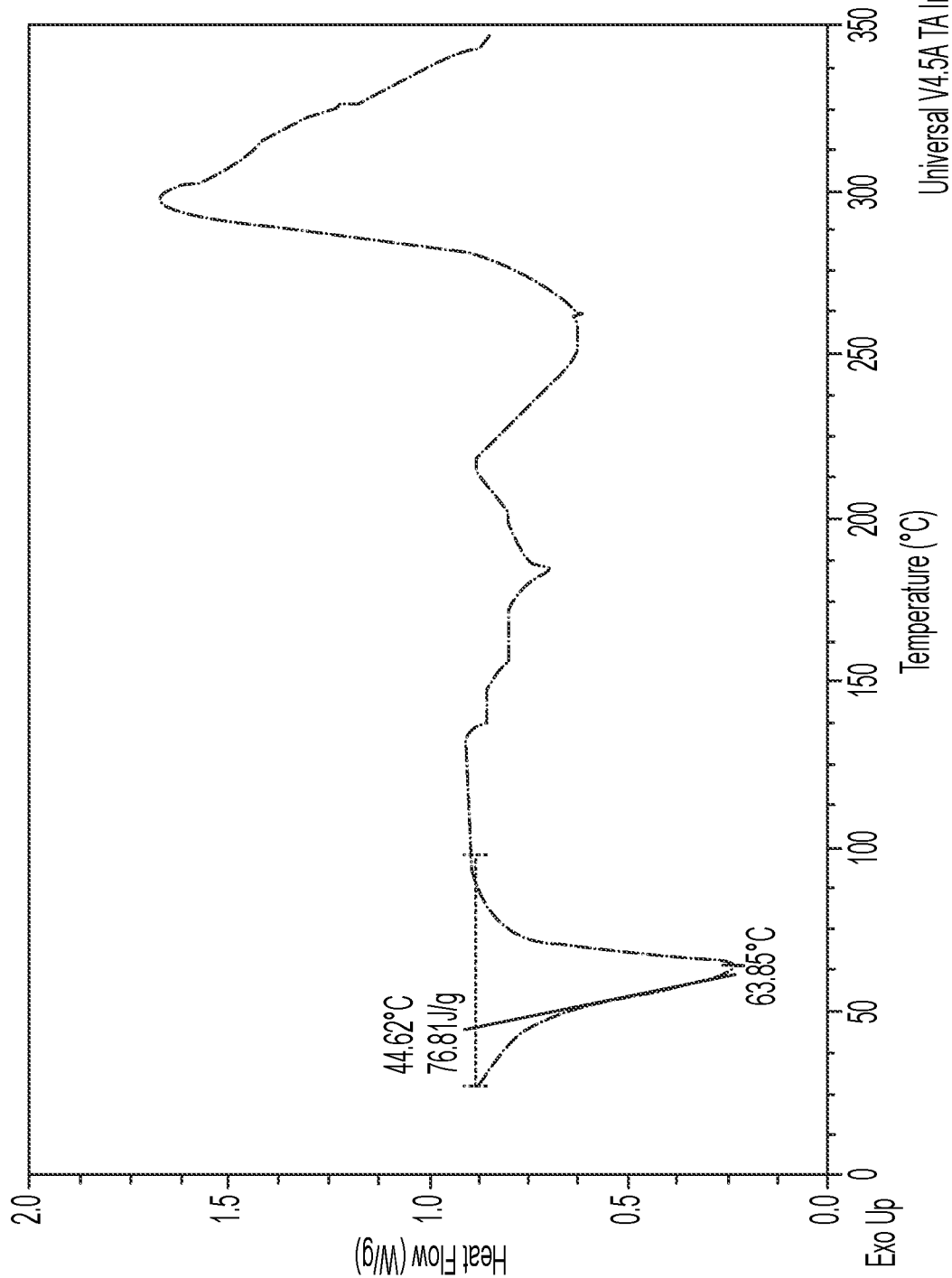
FIG. 27 depicts a differential scanning calorimetry ("DSC") thermograph of the crystalline potassium salt isopropanol solvate of AMG 176 indicating endothermic events at 64 and 180° C.

Differential scanning calorimetry (DSC) thermographs were obtained, as set forth in the Examples, for the crystalline potassium salt isopropanol solvate form of AMG 176. The DSC curve indicates endothermic events at 64° C.±3° C. and 180° C.±3° C. For example, in some embodiments the crystalline potassium salt isopropanol solvate form of AMG 176 is characterized by DSC, as shown in FIG. 27.

Figure 28:
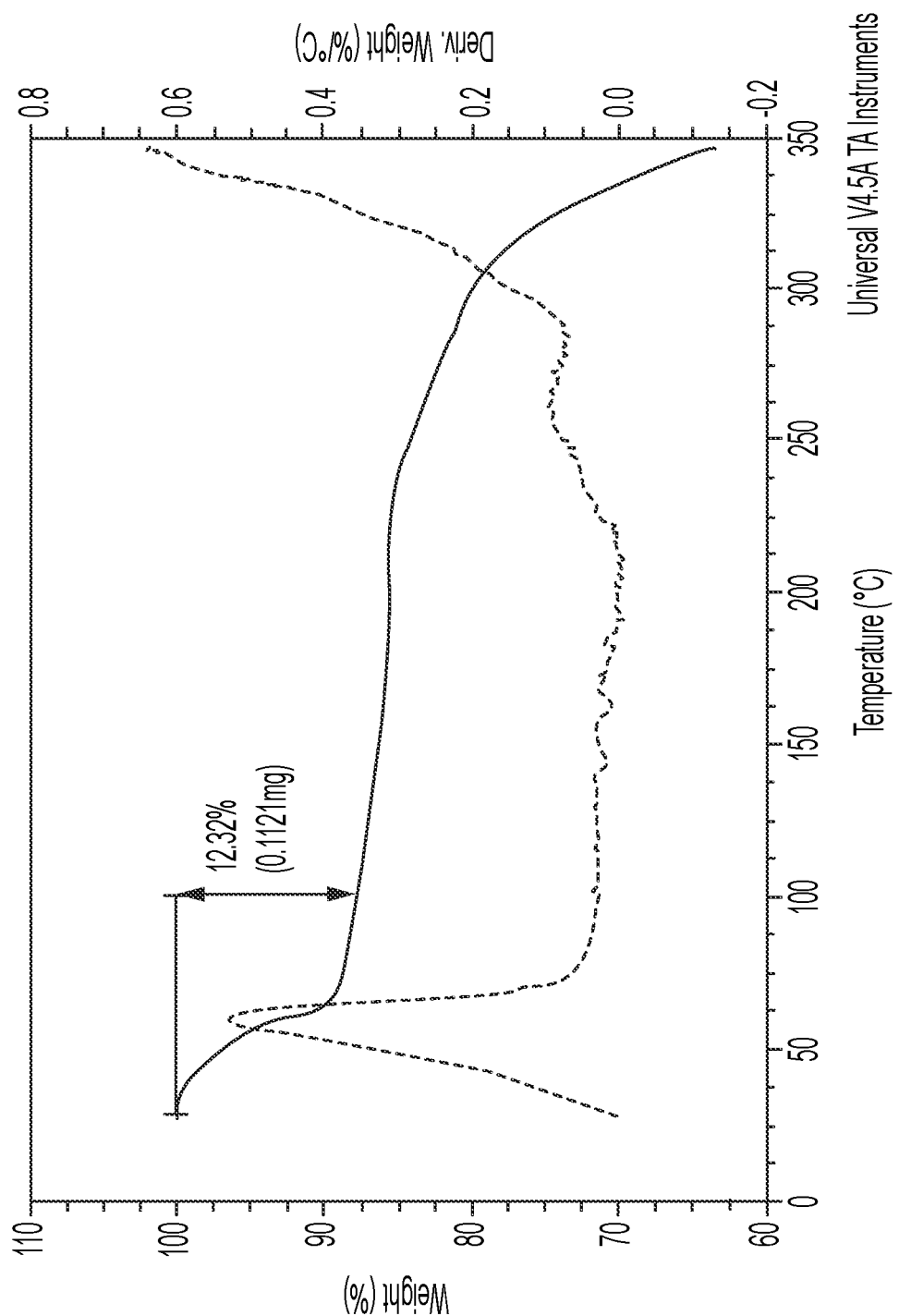
FIG. 28 depicts a thermogravimetric analysis ("TGA") trace of the crystalline potassium salt isopropanol solvate form of AMG 176 showing 12% weight loss.

The crystalline potassium salt isopropanol solvate form of AMG 176 can be characterized by thermogravimetric analysis (TGA). Thus, the crystalline potassium salt isopropanol solvate form of AMG 176 can be characterized by a weight loss in a range of about 12% weight loss. In some embodiments, the crystalline potassium salt isopropanol solvate of AMG 176 has a thermogravimetric analysis substantially as depicted in FIG. 28, wherein by "substantially" is meant that the reported TGA features can vary by ±5° C.

Figure 29:
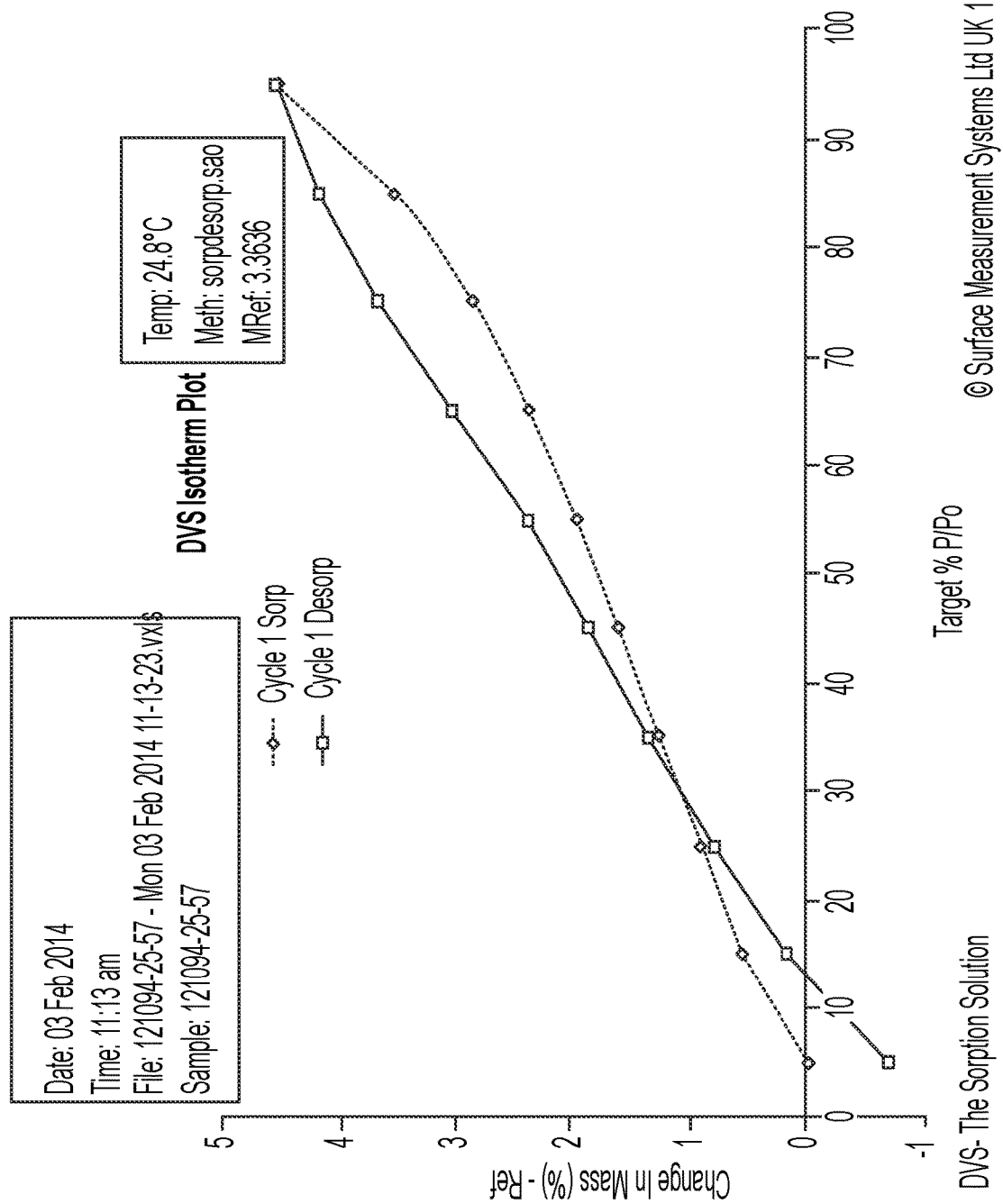
FIG. 29 depicts a moisture sorption profile (DVS) of the crystalline potassium salt isopropanol solvate form of AMG 176 showing weight gain of about 4.5% by 95% relative humidity, which is lost upon desorption.
Figure 30:
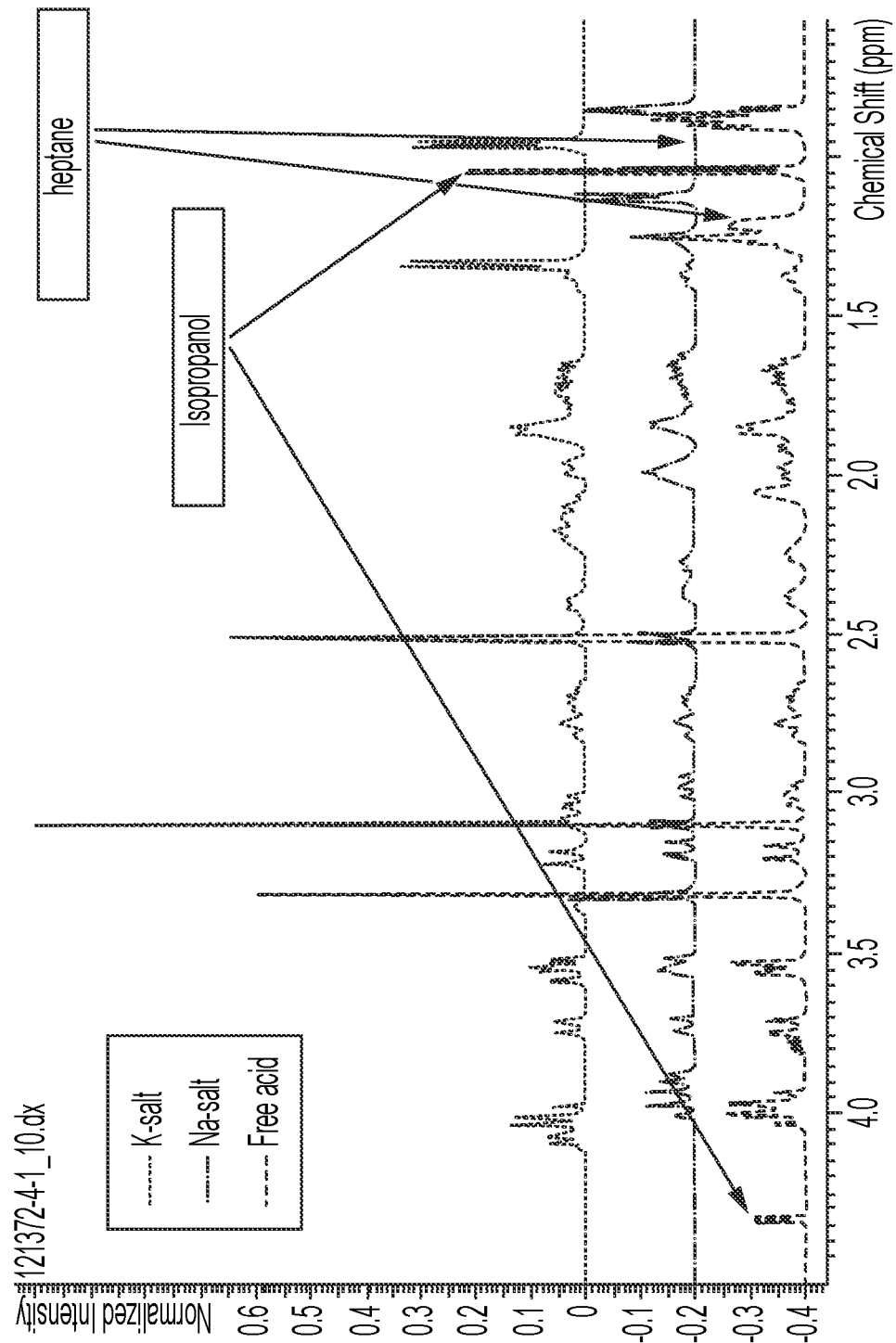
FIG. 30 depicts an overlay of proton nuclear magnetic resonance ($^1$HNMR) spectra of (top to bottom) the crystalline AMG 176 free acid, sodium salt, and potassium salt isopropanol solvate form of AMG 176 showing the presence of isopropanol in the solvate.

The crystalline potassium salt isopropanol solvate form of AMG 176 can be characterized by a moisture sorption profile. For example, in some embodiments, the crystalline potassium salt isopropanol solvate form of AMG 176 is characterized by the moisture sorption profile as shown in FIG. 29, showing a weight gain of about 4.5% by 95% relative humidity, which is lost upon desorption.

Figure 31:
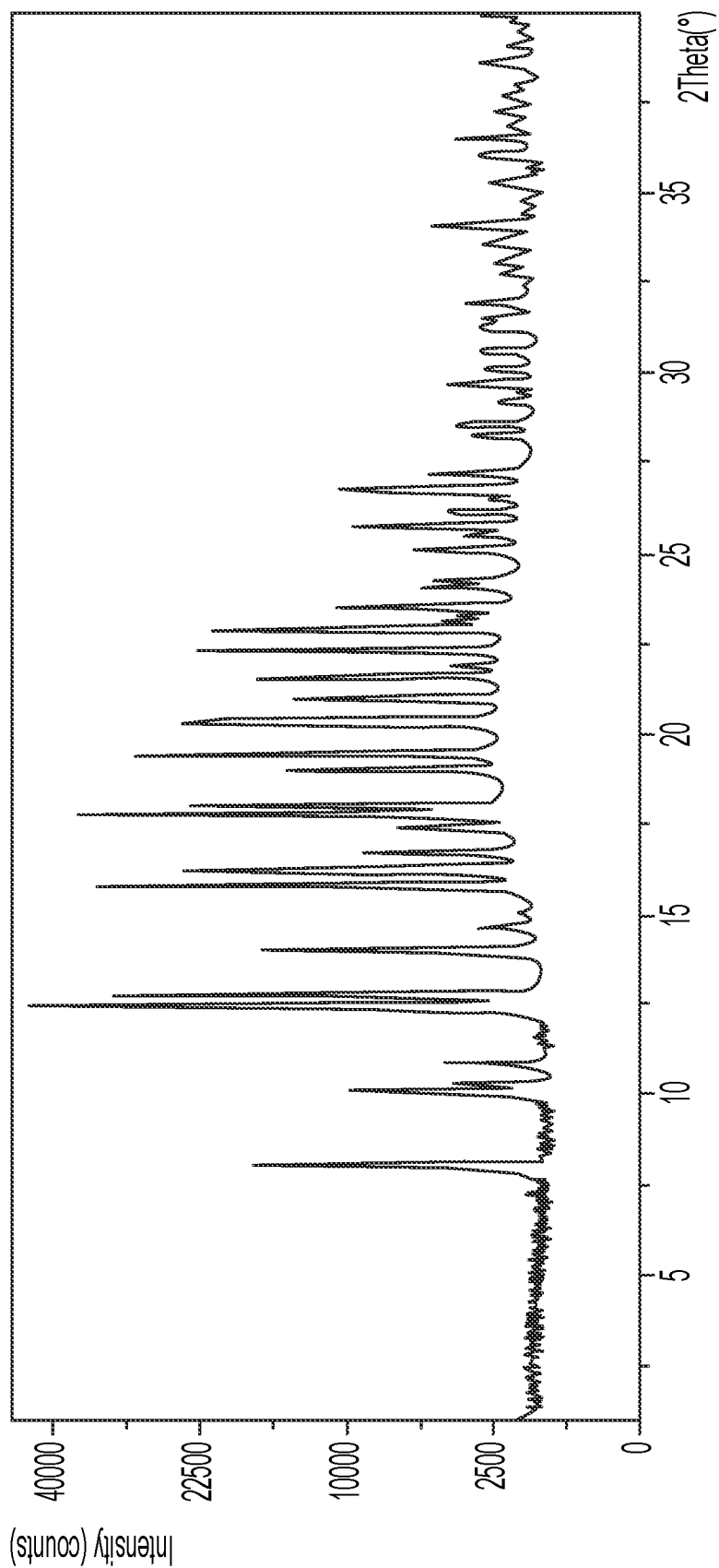
FIG. 31 depicts an X-ray powder diffraction ("XRPD") pattern of the crystalline tetrahydrofuran solvate of AMG 176.

Tetrahydrofuran Solvate Form: The crystalline tetrahydrofuran solvate form of AMG 176 can be characterized by an X-ray powder diffraction pattern, obtained as set forth in the Examples, having peaks at 12.5, 15.8, and 17.8±0.2° 2θ using Cu Kα radiation, optionally further characterized by additional peaks at 12.8, 16.2, 18.0, 19.4, 20.3, 20.4, and 22.3±0.2° 2θ using Cu Kα radiation, and/or additional peaks at 8.1, 10.1, 14.0, 19.0, 21.0, 21.6, 22.9, 23.5, 25.7, and 26.8±0.2° 2θ using Cu Kα radiation. In some embodiments, the crystalline tetrahydrofuran solvate form of AMG 176 has an X-ray powder diffraction pattern substantially as shown in FIG. 31, wherein by "substantially" is meant that the reported peaks can vary by ±0.2°. It is well known in the field of XRPD that while relative peak heights in spectra are dependent on a number of factors, such as sample preparation and instrument geometry, peak positions are relatively insensitive to experimental details.

Figure 32:
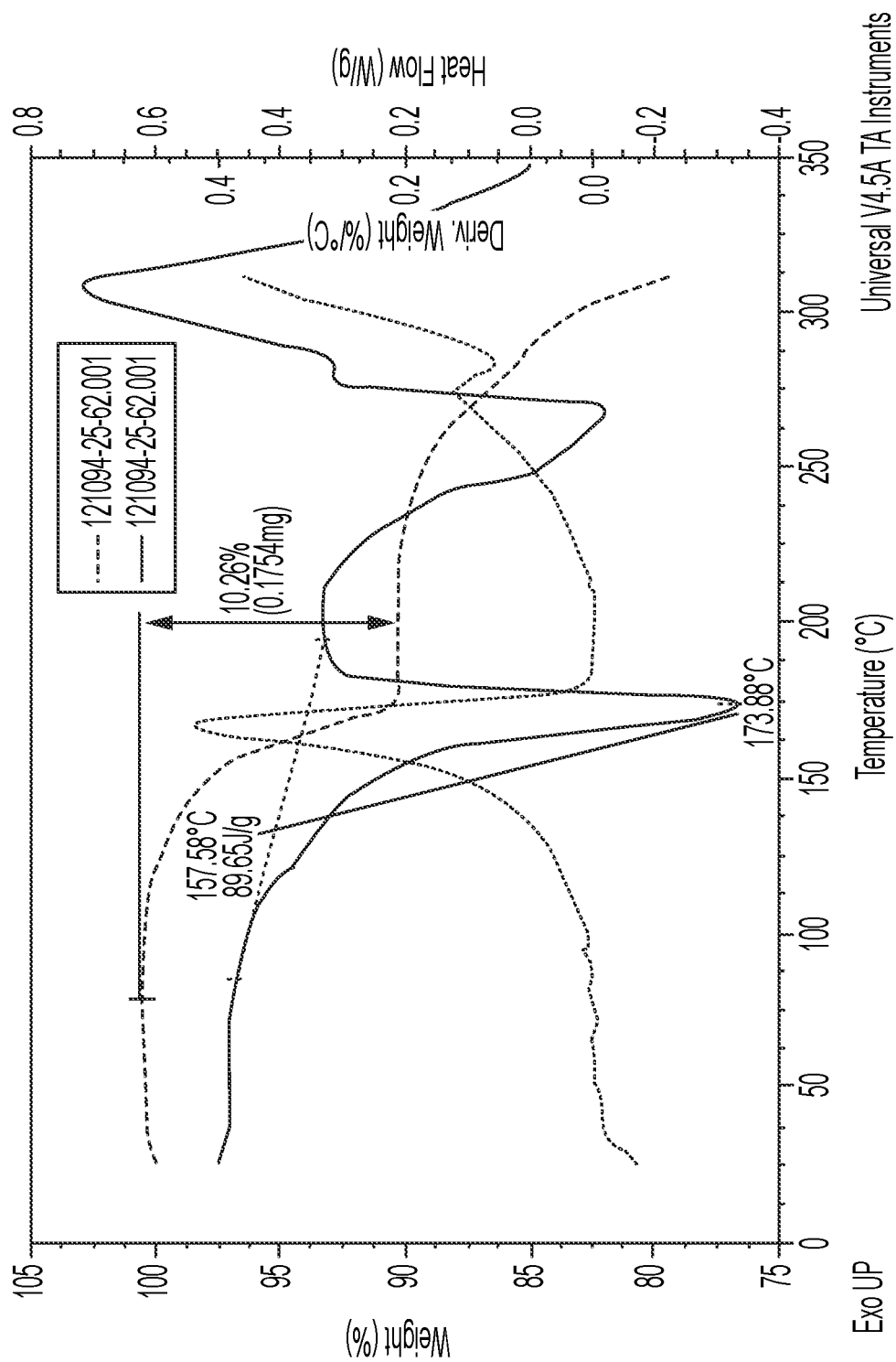
FIG. 32 depicts an overlay of a a differential scanning calorimetry ("DSC") thermograph and a thermogravimetric analysis ("TGA") trace of the crystalline tetrahydrofuran solvate form of AMG 176 indicating an endothermic transition at 174° C. and showing 10% weight loss.

Differential scanning calorimetry (DSC) thermographs were obtained, as set forth in the Examples, for the crystalline tetrahydrofuran solvate form of AMG 176. The DSC curve indicates an endothermic event at 174° C.±3° C. For example, in some embodiments the crystalline tetrahydrofuran solvate form of AMG 176 is characterized by DSC, as shown in FIG. 32.

The crystalline tetrahydrofuran solvate form of AMG 176 can be characterized by thermogravimetric analysis (TGA). Thus, the crystalline tetrahydrofuran solvate form of AMG 176 can be characterized by a weight loss in a range of about 10% weight loss. In some embodiments, the crystalline tetrahydrofuran solvate of AMG 176 has a thermogravimetric analysis substantially as depicted in FIG. 32, wherein by "substantially" is meant that the reported TGA features can vary by ±5° C.

Figure 33:
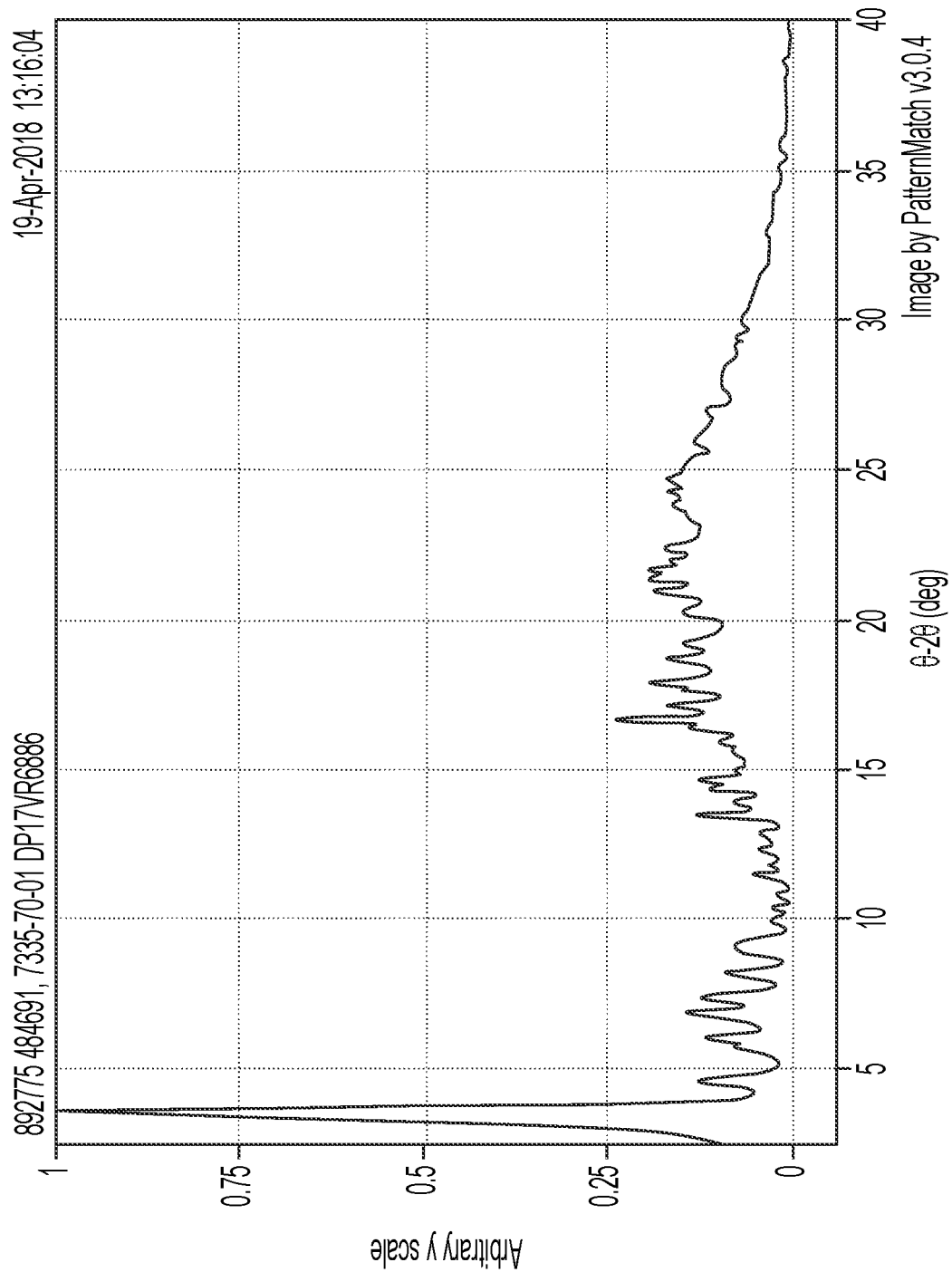
FIG. 33 depicts an X-ray powder diffraction ("XRPD") pattern of the crystalline sodium salt acetonitrile solvate form of AMG 176.

Sodium Salt Acetonitrile Solvate Form: The crystalline sodium salt acetonitrile solvate form of AMG 176 can be characterized by an X-ray powder diffraction pattern, obtained as set forth in the Examples, having peaks at 3.4, 3.7, and 16.7±0.2° 2θ using Cu Kα radiation, optionally further characterized by additional peaks at 17.1, 17.9, 21.0, 21.4, and 21.7±0.2° 2θ using Cu Kα radiation, and/or additional peaks at 6.9, 7.4, 13.5, 14.4, 14.7, 16.4, 17.6, 18.7, 19.1, 19.3, 20.2, 22.4, 23.9, 24.2, and 24.7±0.2° 2θ using Cu Kα radiation. In some embodiments, the crystalline sodium salt acetonitrile solvate form of AMG 176 has an X-ray powder diffraction pattern substantially as shown in FIG. 33, wherein by "substantially" is meant that the reported peaks can vary by ±0.2°. It is well known in the field of XRPD that while relative peak heights in spectra are dependent on a number of factors, such as sample preparation and instrument geometry, peak positions are relatively insensitive to experimental details.

Figure 34:
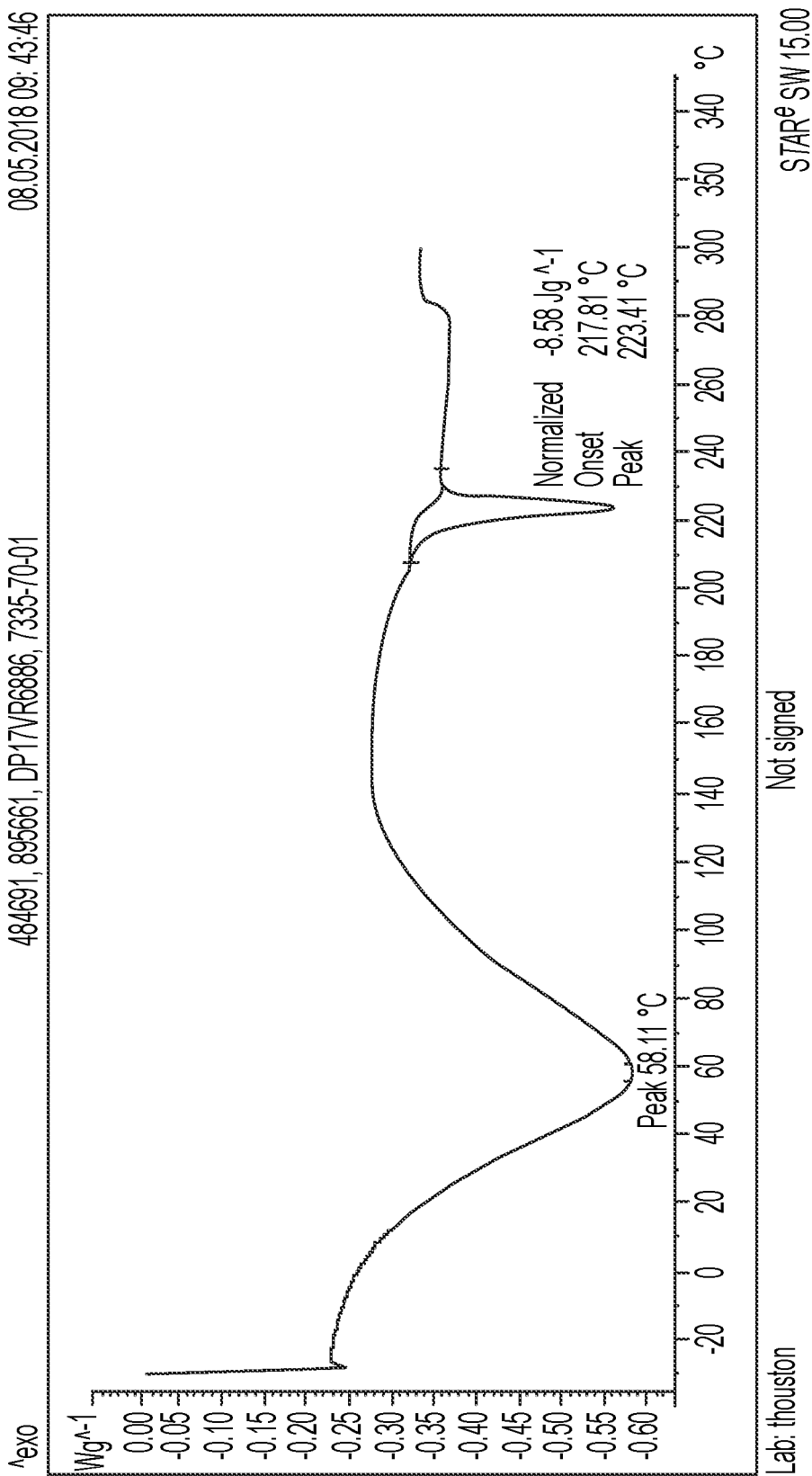
FIG. 34 depicts a differential scanning calorimetry ("DSC") thermograph of the crystalline sodium salt acetonitrile solvate form of AMG 176 indicating an endothermic event at 58° C.

Differential scanning calorimetry (DSC) thermographs were obtained, as set forth in the Examples, for the crystalline sodium salt acetonitrile solvate form of AMG 176. The DSC curve indicates endothermic transitions at 58° C.±3° C. and 223° C.±3° C. For example, in some embodiments the crystalline sodium salt acetonitrile solvate form of AMG 176 is characterized by DSC, as shown in FIG. 34.

Figure 35:
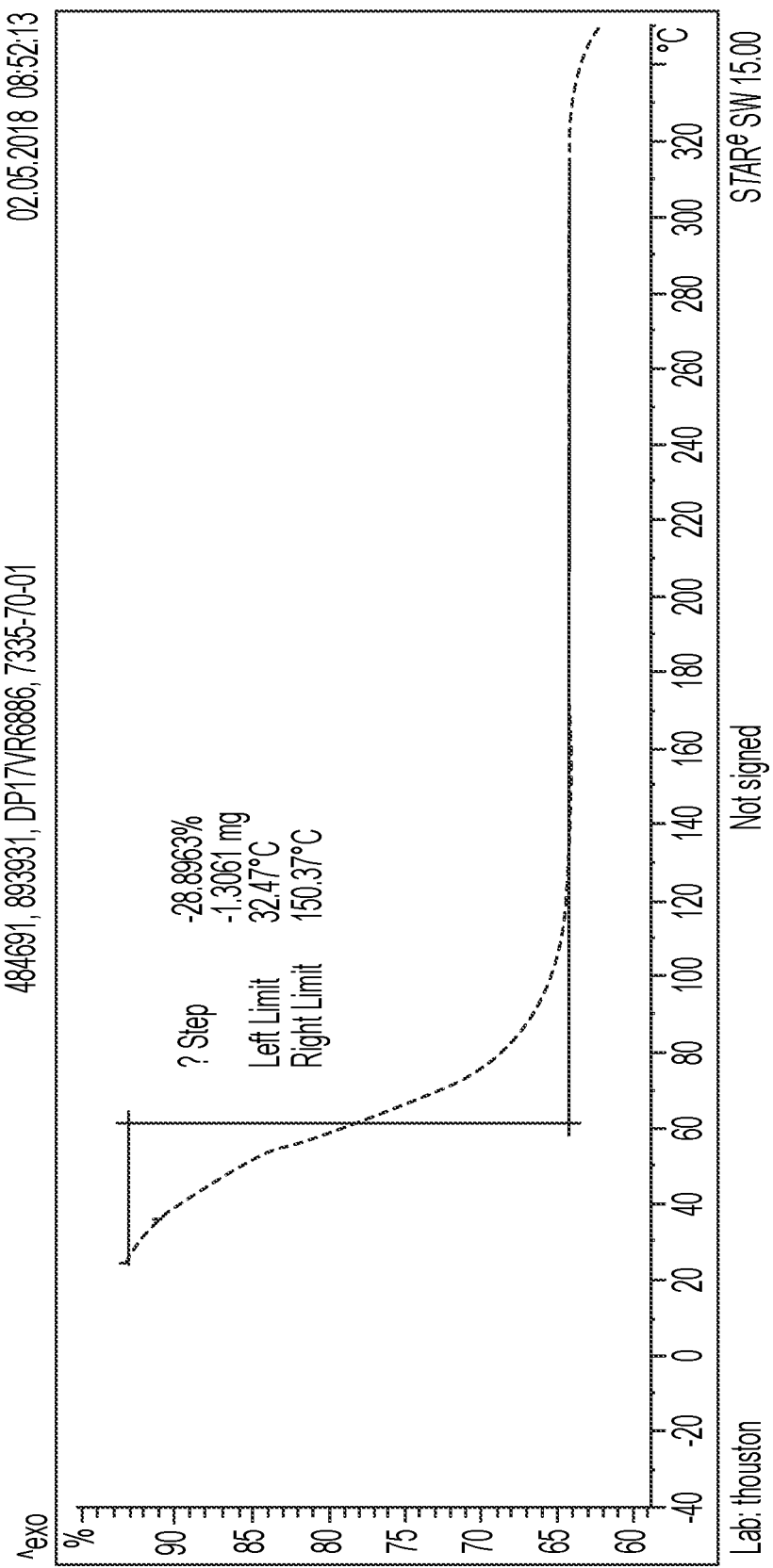
FIG. 35 depicts a thermogravimetric analysis ("TGA") trace of the crystalline sodium salt acetonitrile solvate form of AMG 176 showing 29% weight loss to 150° C.

The crystalline sodium salt acetonitrile solvate form of AMG 176 can be characterized by thermogravimetric analysis (TGA). Thus, the crystalline sodium salt acetonitrile solvate form of AMG 176 can be characterized by a weight loss in a range of about 29% weight loss to 150° C. In some embodiments, the crystalline sodium salt acetonitrile solvate of AMG 176 has a thermogravimetric analysis substantially as depicted in FIG. 35, wherein by "substantially" is meant that the reported TGA features can vary by ±5° C.

Figure 36:
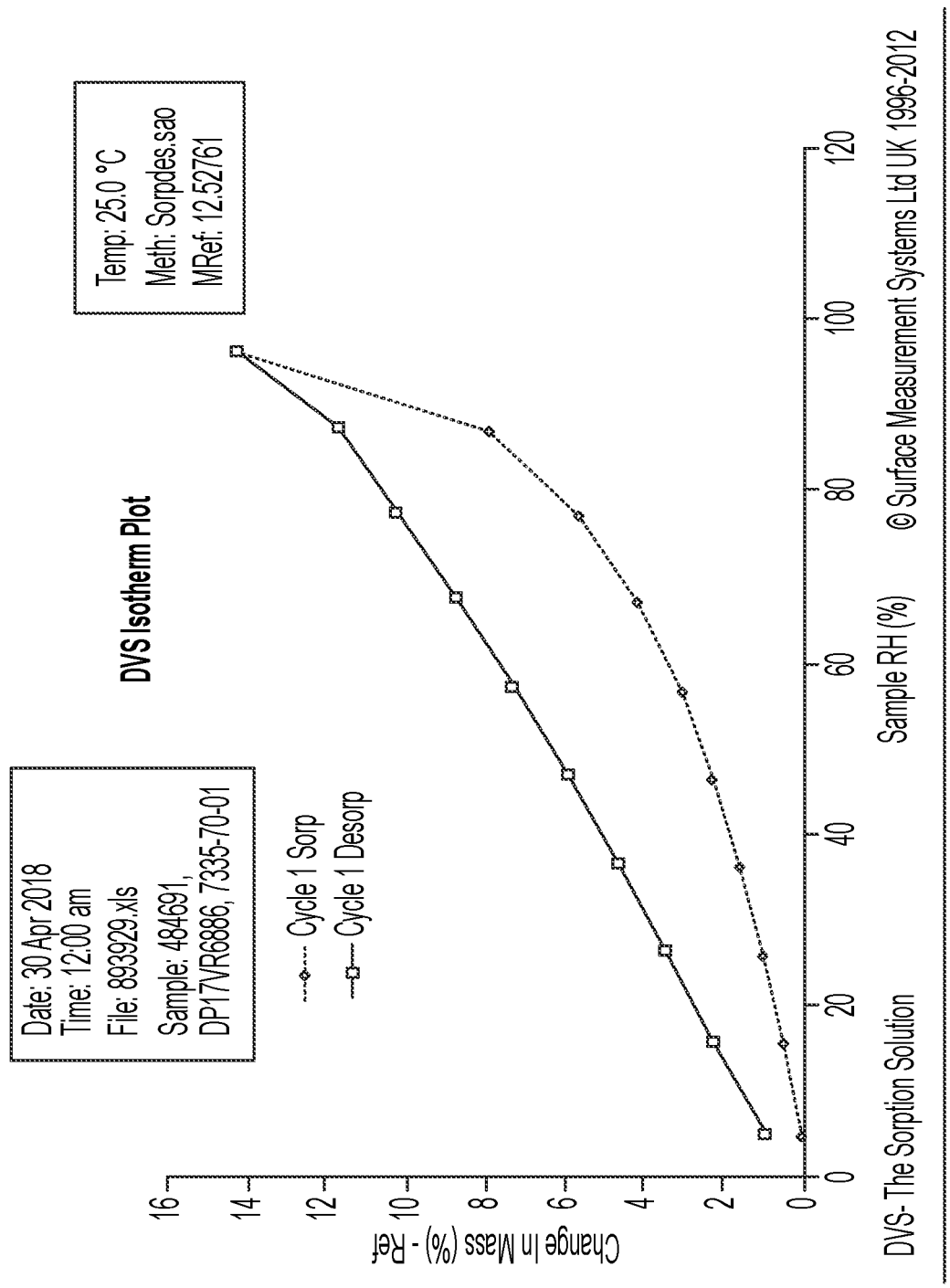
FIG. 36 depicts a moisture sorption profile (DVS) of the crystalline sodium salt acetonitrile solvate form of AMG 176 showing weight gain of about 14% by 95% relative humidity, followed by 13% loss upon desorption.

The crystalline sodium salt acetonitrile solvate form of AMG 176 can be characterized by a moisture sorption profile. For example, in some embodiments, the crystalline sodium salt acetonitrile solvate form of AMG 176 is characterized by the moisture sorption profile as shown in FIG. 36, showing a weight gain of about 14% by 95% relative humidity, followed by 13% loss upon desorption.

Pharmaceutical Formulations

Provided herein are pharmaceutical formulations comprising a salt or solvate of AMG 176 as disclosed herein and a pharmaceutically acceptable excipient.

In some embodiments, the pharmaceutical formulation is in the form of a tablet. In some embodiments, the pharmaceutical formulation is in the form of an immediate release tablet. Solid oral drug compositions (e.g., tablets) or preparations have various release profiles, such as an immediate release profile as referenced by FDA guidelines ("Dissolution Testing of Immediate Release Solid Oral Dosage Forms", issued August 1997, Section IV-A). In the dissolution testing guideline for immediate release profiles, materials which dissolve at least 80% in the first 30 to 60 minutes in solution qualify as immediate release profiles. Therefore, immediate release solid dosage forms permit the release of most or all of the active ingredient over a short period of time, such as 60 minutes or less, and make rapid absorption of the drug possible. In contrast, extended release solid oral dosage forms permit the release of the active ingredient over an extended period of time in an effort to maintain therapeutically effective plasma levels over similarly extended time intervals, improve dosing compliance, and/or to modify other pharmacokinetic properties of the active ingredient.

"Pharmaceutically acceptable excipient" refers to a broad range of ingredients that may be combined with a compound or salt of the present invention to prepare a pharmaceutical composition or formulation. Excipients are additives that are included in a formulation because they either impart or enhance the stability, delivery and manufacturability of a drug product, and are physiologically innocuous to the recipient thereof. Regardless of the reason for their inclusion, excipients are an integral component of a drug product and therefore need to be safe and well tolerated by patients. Given the teachings and guidance provided herein, those skilled in the art will readily be able to vary the amount or range of excipient without increasing viscosity to an undesirable level. Excipients may be chosen to achieve a desired bioavailability, desired stability, resistance to aggregation or degradation or precipitation, protection under conditions of freezing, lyophilization or high temperatures, or other properties. Typically, excipients include, but are not limited to, diluents, colorants, vehicles, anti-adherants, glidants, disintegrants, flavoring agents, coatings, binders, sweeteners, lubricants, sorbents, preservatives, and the like. Examples of suitable excipients are well known to the person skilled in the art of tablet formulation and may be found e.g. in *Handbook of Pharmaceutical Excipients* (eds. Rowe, Sheskey & Quinn), 6th edition 2009.

As used herein the term "excipients" is intended to refer to inter alia basifying agents, solubilizers, glidants, fillers, binders, lubricant, diluents, preservatives, surface active agents, dispersing agents and the like. The term also includes agents such as sweetening agents, flavoring agents, coloring agents and preserving agents. Such components will generally be present in admixture within the tablet.

Examples of solubilizers include, but are not limited to, ionic surfactants (including both ionic and non-ionic surfactants) such as sodium lauryl sulfate, cetyltrimethylammonium bromide, polysorbates (such as polysorbate 20 or 80), poloxamers (such as poloxamer 188 or 207), and macrogols.

Examples of lubricants, glidants and flow aids include, but are not limited to, magnesium stearate, calcium stearate, stearic acid, hydrogenated vegetable oil, glyceryl palmitostearate, glyceryl behenate, sodium stearyl fumarate, colloidal silicon dioxide, and talc. The amount of lubricant in a tablet can generally be between 0.1-5% by weight.

Examples of disintegrants include, but are not limited to, starches, celluloses, cross-linked PVP, sodium starch glycolate, croscarmellose sodium, etc.

Examples of fillers (also known as bulking agents or diluents) include, but are not limited to, starches, maltodextrins, polyols (such as lactose), and celluloses. Tablets provided herein may include lactose and/or microcrystalline cellulose. Lactose can be used in anhydrous or hydrated form (e.g. monohydrate), and is typically prepared by spray drying, fluid bed granulation, or roller drying.

Examples of binders include, but are not limited to, cross-linked PVP, HPMC, microcrystalline cellulose, sucrose, starches, etc.

In some embodiments, the pharmaceutically acceptable excipients can comprise one or more diluent, binder, or disintegrant. In embodiments, the pharmaceutically acceptable excipients can comprise a diluent comprising one or more of microcrystalline cellulose, starch, dicalcium phosphate, lactose, sorbitol, mannitol, sucrose, and methyl dextrins, a binder comprising one or more of povidone, hydroxypropyl methylcellulose, hydroxypropyl cellulose, and sodium carboxymethylcellulose, and a disintegrant comprising one or more of crospovidine, sodium starch glycolate, and croscarmellose sodium.

Tablets provided herein may be uncoated or coated (in which case they include a coating). Although uncoated tablets may be used, it is more usual to provide a coated tablet, in which case a conventional non-enteric coating may be used. Film coatings are known in the art and can be composed of hydrophilic polymer materials, but are not limited to, polysaccharide materials, such as hydroxypropylmethyl cellulose (HPMC), methylcellulose, hydroxyethyl cellulose (HEC), hydroxypropyl cellulose (HPC), poly(vinylalcohol-co-ethylene glycol) and other water soluble polymers. Though the water soluble material included in the film coating of the present invention may include a single polymer material, it may also be formed using a mixture of more than one polymer. The coating may be white or colored e.g. gray. Suitable coatings include, but are not limited to, polymeric film coatings such as those comprising polyvinyl alcohol e.g. 'Opadry® II' (which includes part-hydrolysed PVA, titanium dioxide, macrogol 3350 and talc, with optional coloring such as iron oxide or indigo carmine or iron oxide yellow or FD&C yellow #6). The amount of coating will generally be between 2-4% of the core's weight, and in certain specific embodiments, 3%. Unless specifically stated otherwise, where the dosage form is coated, it is to be understood that a reference to % weight of the tablet means that of the total tablet, i.e. including the coating.

The pharmaceutical formulations disclosed herein can further comprise a surfactant. As used herein, the surfactant can be cationic, anionic, or non-ionic. In some embodiments, the pharmaceutical formulation can comprise a non-ionic surfactant. In some embodiments, the surfactant can comprise a polysorbate, a poloxamer, or a combination thereof. In some embodiments, the surfactant can comprise polysorbate 20, polysorbate 60, polysorbate 80, or a combination thereof.

Methods of Treating a Subject

Further provided herein are methods of treating a subject suffering from cancer, comprising administering to the subject a therapeutically effective amount of a salt or solvate form of AMG 176 as disclosed herein, optionally as a pharmaceutical formulation as disclosed herein. In some embodiments, the cancer is multiple myeloma, non-Hodgkin's lymphoma, or acute myeloid leukemia.

Preparation of Salt and Solvate Forms

The salt and solvate forms disclosed herein can be prepared by a variety of methods known to those of skill in the art. For example, the salt and solvate forms can be prepared from amorphous, crude, or crystalline forms of AMG 176. In some embodiments, AMG 176 is combined with a solvent and/or a salt forming agent to form a desired salt or solvate form, for example as discussed in the examples below. In some embodiments, AMG 176 is dissolved in a solvent, or is combined with a solvent to form a slurry. In some embodiments, AMG 176 is dissolved in a solvent, or is combined with a solvent to form a slurry, and then a salt forming agent is added to the slurry. In some embodiments, a salt forming agent is added before the slurry is formed. In some embodiments, AMG 176 is combined with a solvent and/or a salt forming agent and the solution or slurry thus formed is aged to form the salt or solvate forms. In some embodiments, the solution or slurry is heated prior to aging or crystal formation.

Other Embodiments

It is to be understood that while the disclosure is read in conjunction with the detailed description thereof, the foregoing description is intended to illustrate and not limit the scope of the disclosure, which is defined by the scope of the appended claims. Other aspects, advantages, and modifications are within the scope of the following claims.

EXAMPLES

The following examples are provided for illustration and are not intended to limit the scope of the invention.

Materials and Methods

Commercially available reagents are used as is without further purification unless specified.

The synthesis of the starting material (AMG 176) for the following methods is disclosed in U.S. Pat. No. 9,562,061. The crystalline forms disclosed herein may be characterized using conventional means, including physical constants and spectral data.

X-Ray Powder Diffraction: X-ray powder diffraction data were obtained using a PANalytical X-Pert Pro diffractometer. The radiation used was CuKα (1.542 Å) with voltage and current of 45 kV and 40 mA. Data was collected at ambient temperature from 5.00 to 40.00° 2θ using a step size of 0.0167°. A low background sample holder was used and the stage was rotated at a revolution time of 2.0 seconds. The incident beam path was equipped with a 0.02 rad soller slit, 15 mm mask, 4° fixed antiscatter slit and a programmable divergence slit. The diffracted beam was equipped with a 0.02 rad soller slit, programmable anti-scatter slit and a 0.02 mm nickel filter.

Alternatively, XRPD patterns were collected in transmission mode with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640e) was analyzed to verify the observed position of the Si 111 peak is consistent with the NIST-certified position. A specimen of the sample was sandwiched between 3-μm-thick films and analyzed in transmission geometry. A beam-stop, short anti-scatter extension and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data acquisition parameters for each pattern are displayed above the image in the Data section of this report including the divergence slit (DS) before the mirror.

XRPD patterns were collected in reflection mode with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640e) was analyzed to verify the observed position of the Si 111 peak is consistent with the NIST-certified position. A specimen of the sample was packed in a well. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v. 2.2b. The data acquisition parameters for each pattern are displayed above the image in the Data section of this report including the divergence slit (DS) and the incident-beam SS.

Within the figure referenced for a given indexed XRPD pattern, agreement between the allowed peak positions, marked with red bars, and the observed peaks indicates a consistent unit cell determination. Successful indexing of a pattern indicates that the sample is composed primarily of a single crystalline phase unless otherwise stated. Space groups consistent with the assigned extinction symbol, unit cell parameters, and derived quantities are tabulated below the figure. To confirm the tentative indexing solution, the molecular packing motifs within the crystallographic unit cells must be determined. No attempts at molecular packing were performed.

Single Crystal Structure: A colorless needle crystal (monohydrate) with dimensions 0.18×0.11×0.05 mm was mounted on a Nylon loop using very small amount of paratone oil. The crystal was mounted, cell determined to be the monohydrate, and then the temperature was raised to 400 K to dehydrate. The crystal remained at 400K for 4 hours, and then lowered temperature to 173K and data collected. Data were collected using a Bruker CCD (charge coupled device) based diffractometer equipped with an Oxford Cryostream low-temperature apparatus operating at 173 K. Data were measured using omega and phi scans of 0.5° per frame for 30 s. The total number of images was based on results from the program COSMO where redundancy was expected to be 4.0 and completeness to 100% out to 0.83 Å. Cell parameters were retrieved using APEX II software and refined using SAINT on all observed reflections. Data reduction was performed using the SAINT software. Scaling and absorption corrections were applied using SADABS multi-scan technique. The structures are solved by the direct method using the SHELXS-97 program and refined by least squares method on F2, SHELXL-97, which are incorporated in SHELXTL-PC V 6.10.

Differential Scanning Calorimetry: Differential scanning calorimetry (DSC) analysis was conducted on a TA Instruments Q100 instrument. A sample size of approximately 1 mg was weighed out into a standard aluminum DSC pan; the pan was uncrimped. The sample was heated at 10° C./min from ambient temperature to 300° C. under dry nitrogen at 50 mL/min. Modulated DSC analysis was conducted using a TA Instruments Q100 instrument. Sample sizes of approximately 1 mg were used in aluminum, uncrimped pan. The samples were equilibrated at 20° C. and held for 5 minutes before heating to 300° C. at a heating rate of 3° C./min under dry nitrogen at 50 mL/min. Modulation was ±0.75° C. every 45 seconds.

Alternatively, DSC was performed using a TA Instruments Q2000 differential scanning calorimeter. Temperature calibration was performed using NIST-traceable indium metal. The sample was placed into an aluminum Tzero pan, covered with a lid, crimped, and the weight was accurately recorded. A weighed aluminum pan configured as the sample pan was placed on the reference side of the cell. The data acquisition parameters and pan configuration for each thermogram are displayed in the image in the Data section of this report. The method code on the thermogram is an abbreviation for the start and end temperature as well as the heating rate; e.g., −30-250-10 means "from −30° C. to 250° C., at 10° C./min".

Alternatively, MDSC data were obtained on a TA Instruments Q2000 differential scanning calorimeter equipped with a refrigerated cooling system (RCS). Temperature calibration was performed using NIST-traceable indium metal. The sample was placed into an aluminum DSC pan, and the weight was accurately recorded. The pan was covered with a lid and the lid was crimped. A weighed, crimped aluminum pan was placed on the reference side of the cell. Data were obtained using a modulation amplitude of ±0.8° C. and a 60 second period with an underlying heating rate of 2° C./minute from −30° C. to 250° C. The reported glass transition temperature is obtained from the inflection point of the step change in the reversing heat flow versus temperature curve.

Alternatively, DSC was performed using a Mettler-Toledo DSC3+ differential scanning calorimeter. Temperature calibration was performed using adamantane, phenyl salicylate, indium, tin, and zinc. The sample was placed into a hermetically sealed or an open aluminum DSC pan, and the weight was accurately recorded. A weighed aluminum pan configured as the sample pan was placed on the reference side of the cell. The samples were analyzed from −30 to 250° C. at a ramp rate of 10° C./min. Although thermograms are plotted by reference temperature (x-axis), results are reported according to sample temperatures.

Thermal Analysis: Thermogravimetric analysis was conducted on a TA Instruments Q500 instrument. A sample size of approximately 1-5 mg was used in an aluminum pan. The sample was heated at 10° C./min from ambient temperature to 400° C. under dry nitrogen at 25 mL/min.

Alternatively, TG analyses were performed using a TA Instruments Q5000 IR thermogravimetric analyzer. Temperature calibration was performed using nickel and Alumel™. Each sample was placed in an aluminum pan. The sample was hermetically sealed, the lid pierced, then inserted into the TG furnace. The furnace was heated under nitrogen. The data acquisition parameters for each thermogram are displayed in the image in the Data section of this report. The method code on the thermogram is an abbreviation for the start and end temperature as well as the heating rate; e.g., 25-350-10 means "from 25° C. to 350° C., at 10° C./min".

Alternatively, Thermogravimetric analyses were performed using a Mettler Toledo TGA/DSC3+ analyzer. Temperature calibration was performed using phenyl salicylate, indium, tin, and zinc. The sample was placed in an aluminum pan. The open pan was inserted into the TG furnace. The furnace was heated under nitrogen. Each sample was heated from ambient temperature to 350° C. at ramp rates of 2, 5, or 10° C./min. Although thermograms are plotted by reference temperature (x-axis), results are reported according to sample temperatures.

Moisture Sorption: Moisture sorption data was collected at 25° C. using a VTI vapor sorption analyzer. A sample size of approximately 4-10 mg was used in a standard platinum pan. Hygroscopicity was evaluated from 5 to 95% RH in increments of 5% RH. Data for adsorption and desorption cycles were collected. Equilibrium criteria were set at 0.001% weight change in 10 minute with a maximum equilibration time of 180 minutes.

NMR: Solution proton NMR spectra were acquired by Spectral Data Services of Champaign, IL at 25° C. with a Varian UNITYINOVA-400 spectrometer. Samples were dissolved in DMSO-d6. In some cases, the solution NMR spectra were acquired at SSCI with an Agilent DD2-400 spectrometer using deuterated DMSO or methanol.

$^{13}$C SSNMR data was collected on a Bruker DSX spectrometer operating at 600 MHz ($^1$H). A 4 mm H/F/X spinning probe operating at a spinning frequency of 14 kHz was used for all experiments. CPMAS with TOSS program was used with a recycle delay of 10 s. A $^1$H 90° pulse of 2.5 μs and $^{13}$C 180° pulse of 8 μs were used. Decoupling was carried out using a spinal64 sequence. 4096 transients were acquired for signal averaging. The data was processed with Topspin 3.0 software.

Example 1: AMG 176 Ammonium Salt

AMG 176 free acid was dissolved at a concentration of 25 mg/mL at 50° C. in acetonitrile followed by the addition of 2M ammonia in methanol. The solution was dispersed in a sonic bath for two hours resulting in a precipitate. Solids were identified as crystalline by XRPD.

TABLE 1

XRPD Data Table

| Pos. [°2Th.] | FWHM [°2Th.] | d-spacing [Å] | Height [cts] | Rel. Int. [%] |
|---|---|---|---|---|
| 7.91 | 0.40 | 11.18 | 148.64 | 12.68 |
| 10.05 | 0.40 | 8.80 | 53.36 | 4.55 |
| 11.04 | 0.33 | 8.01 | 154.49 | 13.18 |
| 12.65 | 0.20 | 7.00 | 67.39 | 5.75 |
| 13.86 | 0.67 | 6.39 | 166.51 | 14.20 |
| 16.59 | 0.27 | 5.34 | 1172.23 | 100.00 |
| 17.57 | 0.23 | 5.05 | 496.69 | 42.37 |
| 18.38 | 0.27 | 4.83 | 552.23 | 47.11 |
| 19.23 | 0.47 | 4.62 | 350.87 | 29.93 |
| 20.16 | 0.33 | 4.41 | 165.98 | 14.16 |
| 21.61 | 0.40 | 4.11 | 212.58 | 18.13 |
| 22.44 | 0.27 | 3.96 | 350.26 | 29.88 |
| 23.83 | 0.20 | 3.73 | 218.41 | 18.63 |
| 24.89 | 0.27 | 3.58 | 206.00 | 17.57 |
| 27.67 | 0.54 | 3.22 | 205.38 | 17.52 |
| 29.75 | 0.80 | 3.00 | 35.28 | 3.01 |

Example 2: AMG 176 Diethylamine Salt Form A
(Diethylamine Salt Toluene Solvate)

AMG 176 was suspended in toluene. Diethylamine (1.0 eq) was charged to the solution and the mixture was stirred for 3 days at room temperature. Solids were identified as crystalline by XRPD.

TABLE 2

XRPD Data Table

| Pos. [°2Th.] | FWHM [°2Th.] | d-spacing [Å] | Height [cts] | Rel. Int. [%] |
|---|---|---|---|---|
| 7.08 | 0.05 | 12.48 | 874.93 | 3.14 |
| 7.64 | 0.07 | 11.57 | 2655.78 | 9.52 |
| 9.40 | 0.07 | 9.41 | 12126.59 | 43.49 |
| 9.81 | 0.05 | 9.02 | 7309.46 | 26.21 |
| 10.05 | 0.07 | 8.80 | 27884.27 | 100.00 |
| 11.79 | 0.07 | 7.51 | 8593.14 | 30.82 |
| 12.18 | 0.54 | 7.27 | 708.15 | 2.54 |
| 12.49 | 0.08 | 7.09 | 18781.52 | 67.36 |
| 13.06 | 0.08 | 6.78 | 7032.55 | 25.22 |
| 13.56 | 0.08 | 6.53 | 5035.56 | 18.06 |
| 14.22 | 0.08 | 6.23 | 6903.52 | 24.76 |
| 14.72 | 0.08 | 6.02 | 14333.81 | 51.40 |
| 14.88 | 0.05 | 5.95 | 1945.77 | 6.98 |

TABLE 2-continued

XRPD Data Table

| Pos. [°2Th.] | FWHM [°2Th.] | d-spacing [Å] | Height [cts] | Rel. Int. [%] |
|---|---|---|---|---|
| 15.15 | 0.08 | 5.85 | 11142.01 | 39.96 |
| 15.32 | 0.05 | 5.78 | 2304.31 | 8.26 |
| 15.65 | 0.08 | 5.66 | 10385.77 | 37.25 |
| 16.36 | 0.08 | 5.42 | 14959.41 | 53.65 |
| 16.67 | 0.08 | 5.32 | 15320.61 | 54.94 |
| 16.87 | 0.07 | 5.26 | 4904.42 | 17.59 |
| 17.07 | 0.08 | 5.20 | 18082.19 | 64.85 |
| 17.28 | 0.08 | 5.13 | 3117.03 | 11.18 |
| 18.20 | 0.08 | 4.87 | 5518.34 | 19.79 |
| 18.48 | 0.08 | 4.80 | 14509.65 | 52.04 |
| 18.96 | 0.08 | 4.68 | 2773.14 | 9.95 |
| 19.34 | 0.07 | 4.59 | 2262.53 | 8.11 |
| 19.69 | 0.08 | 4.51 | 1382.68 | 4.96 |
| 19.96 | 0.07 | 4.45 | 3208.30 | 11.51 |
| 20.16 | 0.10 | 4.41 | 9292.29 | 33.32 |
| 20.51 | 0.08 | 4.33 | 2055.56 | 7.37 |
| 20.76 | 0.10 | 4.28 | 5789.55 | 20.76 |
| 21.44 | 0.13 | 4.14 | 3243.28 | 11.63 |
| 21.73 | 0.10 | 4.09 | 7437.77 | 26.67 |
| 21.99 | 0.05 | 4.04 | 4622.50 | 16.58 |
| 22.13 | 0.08 | 4.02 | 6083.80 | 21.82 |
| 22.44 | 0.10 | 3.96 | 8640.25 | 30.99 |
| 23.06 | 0.08 | 3.85 | 6226.62 | 22.33 |
| 23.16 | 0.10 | 3.84 | 12496.30 | 44.81 |
| 23.40 | 0.10 | 3.80 | 5462.45 | 19.59 |
| 23.70 | 0.10 | 3.75 | 3665.71 | 13.15 |
| 24.00 | 0.10 | 3.71 | 2267.41 | 8.13 |
| 24.32 | 0.12 | 3.66 | 7814.74 | 28.03 |
| 24.57 | 0.10 | 3.62 | 1465.62 | 5.26 |
| 24.96 | 0.12 | 3.57 | 2587.70 | 9.28 |
| 25.39 | 0.12 | 3.51 | 3025.85 | 10.85 |
| 25.84 | 0.10 | 3.45 | 1480.65 | 5.31 |
| 26.05 | 0.08 | 3.42 | 1700.32 | 6.10 |
| 26.26 | 0.12 | 3.39 | 1800.94 | 6.46 |
| 26.60 | 0.07 | 3.35 | 2004.63 | 7.19 |
| 26.76 | 0.08 | 3.33 | 1355.10 | 4.86 |
| 27.25 | 0.12 | 3.27 | 1464.30 | 5.25 |
| 27.50 | 0.07 | 3.24 | 511.83 | 1.84 |
| 27.96 | 0.12 | 3.19 | 4489.22 | 16.10 |
| 28.28 | 0.08 | 3.16 | 1186.88 | 4.26 |
| 28.70 | 0.10 | 3.11 | 2125.42 | 7.62 |
| 29.03 | 0.07 | 3.08 | 504.19 | 1.81 |
| 29.38 | 0.12 | 3.04 | 1581.09 | 5.67 |
| 29.72 | 0.10 | 3.01 | 557.12 | 2.00 |
| 29.99 | 0.10 | 2.98 | 1411.53 | 5.06 |
| 30.39 | 0.08 | 2.94 | 944.36 | 3.39 |
| 30.47 | 0.05 | 2.93 | 981.64 | 3.52 |
| 30.79 | 0.07 | 2.90 | 313.03 | 1.12 |
| 31.61 | 0.10 | 2.83 | 739.83 | 2.65 |
| 32.33 | 0.13 | 2.77 | 1148.43 | 4.12 |
| 32.73 | 0.07 | 2.74 | 1069.84 | 3.84 |
| 33.16 | 0.10 | 2.70 | 621.32 | 2.23 |
| 33.48 | 0.10 | 2.68 | 154.04 | 0.55 |
| 33.76 | 0.10 | 2.66 | 1075.23 | 3.86 |
| 33.95 | 0.08 | 2.64 | 767.94 | 2.75 |
| 34.51 | 0.08 | 2.60 | 1531.70 | 5.49 |
| 34.89 | 0.15 | 2.57 | 1363.47 | 4.89 |
| 35.16 | 0.12 | 2.55 | 819.23 | 2.94 |
| 35.84 | 0.08 | 2.51 | 731.22 | 2.62 |
| 36.10 | 0.13 | 2.49 | 1193.65 | 4.28 |
| 36.57 | 0.08 | 2.46 | 918.65 | 3.29 |
| 36.89 | 0.10 | 2.44 | 816.34 | 2.93 |
| 37.50 | 0.10 | 2.40 | 361.35 | 1.30 |
| 37.72 | 0.27 | 2.39 | 168.85 | 0.61 |
| 37.92 | 0.08 | 2.37 | 501.78 | 1.80 |
| 38.52 | 0.08 | 2.34 | 533.70 | 1.91 |
| 38.97 | 0.13 | 2.31 | 314.77 | 1.13 |
| 39.26 | 0.10 | 2.29 | 276.62 | 0.99 |
| 39.85 | 0.08 | 2.26 | 951.68 | 3.41 |

$^1$H NMR Data $^1$H NMR (400 MHz, DMSO-d$_6$) δ ppm 0.84 (d, J=6.39 Hz, 2H) 1.09-1.20 (m, 4H) 1.24-1.45 (m, 1H) 1.60-1.88 (m, 3H) 1.90-2.16 (m, 2H) 2.19-2.41 (m, 2H) 2.59-2.85 (m, 1H)

2.87-3.00 (m, 2H) 3.06-3.12 (m, 1H) 3.16 (br d, J=13.85 Hz, 1H) 3.38-3.61 (m, 5H) 3.72 (br d, J=14.49 Hz, 4H) 3.82-4.06 (m, 6H) 5.35 (br dd, J=15.34, 9.16 Hz, 2H) 5.93-6.09 (m, 2H) 6.72 (d, J=8.10 Hz, 2H) 6.83-6.95 (m, 2H) 6.99 (dd, J=7.99, 1.60 Hz, 2H) 7.11-7.28 (m, 6H) 7.69 (d, J=8.52 Hz, 1H).

TABLE 3

X-ray Single Structure Data

| | |
|---|---|
| Crystal System | Orthorhombic |
| Space Group | P2$_1$2$_1$2$_1$ (19) |
| Unit Cell | a = 13.044 Å |
| | b = 13.553 Å |
| | c = 24.929 Å |
| | α = β = γ = 90° |
| Volume | 4407.2 Å$^3$ |

Example 3: AMG 176 Diethylamine Salt Form B (Diethylamine Salt Anhydrous)

AMG 176 diethylamine salt form A (diethylamine toluene solvate) was dried under vacuum at 50° C. Solids were identified as crystalline by XRPD.

TABLE 4

XRPD Data Table

| Pos. [°2Th.] | FWHM [°2Th.] | d-spacing [Å] | Height [cts] | Rel. Int. [%] |
|---|---|---|---|---|
| 7.66 | 0.07 | 11.54 | 2662.38 | 17.12 |
| 7.85 | 0.07 | 11.26 | 2265.41 | 14.57 |
| 9.54 | 0.08 | 9.27 | 1792.32 | 11.53 |
| 10.32 | 0.07 | 8.57 | 8715.25 | 56.06 |
| 10.47 | 0.05 | 8.45 | 2260.56 | 14.54 |
| 12.36 | 0.10 | 7.16 | 10154.55 | 65.32 |
| 13.15 | 0.08 | 6.73 | 7988.63 | 51.38 |
| 13.49 | 0.08 | 6.57 | 5579.22 | 35.89 |
| 13.71 | 0.08 | 6.46 | 1247.91 | 8.03 |
| 14.38 | 0.07 | 6.16 | 646.56 | 4.16 |
| 15.16 | 0.10 | 5.84 | 15546.98 | 100.00 |
| 15.37 | 0.08 | 5.76 | 9386.10 | 60.37 |
| 15.82 | 0.08 | 5.60 | 2000.14 | 12.87 |
| 16.81 | 0.07 | 5.27 | 3122.59 | 20.08 |
| 17.04 | 0.10 | 5.21 | 9429.38 | 60.65 |
| 17.23 | 0.07 | 5.15 | 4475.29 | 28.79 |
| 17.67 | 0.08 | 5.02 | 5182.87 | 33.34 |
| 18.40 | 0.12 | 4.82 | 3646.69 | 23.46 |
| 19.35 | 0.10 | 4.59 | 1183.88 | 7.61 |
| 20.13 | 0.08 | 4.41 | 937.22 | 6.03 |
| 20.52 | 0.10 | 4.33 | 3580.28 | 23.03 |
| 20.87 | 0.10 | 4.26 | 5535.42 | 35.60 |
| 21.31 | 0.10 | 4.17 | 794.37 | 5.11 |
| 21.68 | 0.08 | 4.10 | 3002.76 | 19.31 |
| 21.99 | 0.10 | 4.04 | 2085.05 | 13.41 |
| 22.21 | 0.07 | 4.00 | 1088.17 | 7.00 |
| 22.50 | 0.08 | 3.95 | 1198.68 | 7.71 |
| 23.63 | 0.17 | 3.76 | 2044.01 | 13.15 |
| 24.08 | 0.10 | 3.70 | 1567.15 | 10.08 |
| 24.72 | 0.15 | 3.60 | 1776.51 | 11.43 |
| 25.31 | 0.08 | 3.52 | 3328.49 | 21.41 |
| 25.52 | 0.07 | 3.49 | 1696.03 | 10.91 |
| 26.17 | 0.20 | 3.41 | 649.67 | 4.18 |
| 27.13 | 0.08 | 3.29 | 605.95 | 3.90 |
| 27.61 | 0.08 | 3.23 | 729.08 | 4.69 |
| 28.02 | 0.13 | 3.18 | 403.34 | 2.59 |
| 28.95 | 0.08 | 3.08 | 983.43 | 6.33 |
| 29.33 | 0.10 | 3.05 | 387.92 | 2.50 |
| 31.52 | 0.10 | 2.84 | 438.85 | 2.82 |
| 31.74 | 0.13 | 2.82 | 369.92 | 2.38 |
| 32.39 | 0.20 | 2.76 | 199.43 | 1.28 |
| 33.17 | 0.13 | 2.70 | 116.82 | 0.75 |
| 33.83 | 0.27 | 2.65 | 317.12 | 2.04 |
| 35.13 | 0.17 | 2.55 | 229.15 | 1.47 |
| 36.05 | 0.12 | 2.49 | 275.81 | 1.77 |
| 36.38 | 0.17 | 2.47 | 163.09 | 1.05 |
| 36.94 | 0.17 | 2.43 | 176.58 | 1.14 |
| 37.57 | 0.20 | 2.39 | 83.55 | 0.54 |
| 38.19 | 0.20 | 2.36 | 98.20 | 0.63 |
| 39.57 | 0.10 | 2.28 | 137.86 | 0.89 |

$^1$H NMR Data
$^1$H NMR (400 MHz, CHLOROFORM-d) δ ppm 1.04 (d, J=6.82 Hz, 3H) 1.21-1.32 (m, 5H) 1.40 (d, J=7.03 Hz, 3H) 1.48-1.69 (m, 2H) 1.72-1.90 (m, 3H) 1.90-2.09 (m, 3H) 2.09-2.26 (m, 3H) 2.27-2.51 (m, 4H) 2.61-2.86 (m, 3H) 2.86-3.05 (m, 5H) 3.16-3.33 (m, 4H) 3.59-3.76 (m, 2H) 3.92-4.11 (m, 3H) 5.57 (br dd, J=15.45, 8.42 Hz, 2H) 5.90 (ddd, J=15.24, 7.67, 4.58 Hz, 2H) 6.74-6.94 (m, 2H) 6.94-7.12 (m, 2H) 7.12-7.24 (m, 2H) 7.44-7.64 (m, 4H) 7.72 (d, J=8.52 Hz, 1H).

TABLE 5

X-ray Single Structure Data

| | |
|---|---|
| Crystal System | Orthorhombic |
| Space Group | P2$_1$2$_1$2$_1$ (19) |
| Unit Cell | a = 12.811 Å |
| | b = 13.469 Å |
| | c = 22.552 Å |
| | α = β = γ = 90° |
| Volume | 3891.3 Å$^3$ |

Example 4: AMG 176 Diethanolamine Salt Toluene Solvate

AMG 176 was suspended in toluene. Diethanolamine (1.0 eq) was charged to the solution and the mixture was stirred for 3 days at room temperature. Solids were identified as crystalline by XRPD.

TABLE 6

XRPD Data Table

| Pos. [°2Th.] | FWHM [°2Th.] | d-spacing [Å] | Height [cts] | Rel. Int. [%] |
|---|---|---|---|---|
| 7.10 | 0.07 | 12.45 | 2828.97 | 26.59 |
| 7.41 | 0.05 | 11.93 | 1182.22 | 11.11 |
| 7.58 | 0.05 | 11.67 | 727.04 | 6.83 |
| 9.35 | 0.07 | 9.46 | 5027.24 | 47.25 |
| 9.77 | 0.05 | 9.06 | 2443.11 | 22.96 |
| 10.00 | 0.07 | 8.84 | 9458.59 | 88.90 |
| 11.75 | 0.07 | 7.53 | 4066.73 | 38.22 |
| 12.51 | 0.08 | 7.08 | 10412.00 | 97.86 |
| 13.05 | 0.08 | 6.78 | 1843.59 | 17.33 |
| 13.42 | 0.07 | 6.60 | 1569.93 | 14.75 |
| 14.21 | 0.08 | 6.23 | 1830.55 | 17.20 |
| 14.68 | 0.08 | 6.03 | 4868.38 | 45.75 |
| 15.11 | 0.08 | 5.86 | 5515.74 | 51.84 |
| 15.67 | 0.08 | 5.65 | 5614.34 | 52.77 |
| 16.33 | 0.08 | 5.43 | 5200.75 | 48.88 |
| 16.56 | 0.08 | 5.35 | 6705.90 | 63.02 |
| 16.88 | 0.05 | 5.25 | 2069.50 | 19.45 |
| 17.06 | 0.08 | 5.20 | 10640.14 | 100.00 |
| 18.18 | 0.07 | 4.88 | 3120.58 | 29.33 |

TABLE 6-continued

XRPD Data Table

| Pos. [°2Th.] | FWHM [°2Th.] | d-spacing [Å] | Height [cts] | Rel. Int. [%] |
|---|---|---|---|---|
| 18.39 | 0.08 | 4.83 | 8544.24 | 80.30 |
| 18.76 | 0.07 | 4.73 | 465.62 | 4.38 |
| 18.99 | 0.08 | 4.67 | 1212.52 | 11.40 |
| 19.36 | 0.08 | 4.59 | 1476.40 | 13.88 |
| 19.62 | 0.07 | 4.53 | 801.57 | 7.53 |
| 19.95 | 0.08 | 4.45 | 2190.88 | 20.59 |
| 20.16 | 0.10 | 4.40 | 3774.62 | 35.48 |
| 20.50 | 0.07 | 4.33 | 1539.59 | 14.47 |
| 20.69 | 0.08 | 4.29 | 3036.92 | 28.54 |
| 21.24 | 0.08 | 4.18 | 1657.95 | 15.58 |
| 21.42 | 0.05 | 4.15 | 1930.07 | 18.14 |
| 21.54 | 0.10 | 4.12 | 2978.95 | 28.00 |
| 21.63 | 0.08 | 4.12 | 2479.35 | 23.30 |
| 21.97 | 0.10 | 4.04 | 1943.57 | 18.27 |
| 22.15 | 0.10 | 4.01 | 2875.50 | 27.03 |
| 22.47 | 0.14 | 3.95 | 3397.14 | 31.93 |
| 22.89 | 0.12 | 3.88 | 2721.77 | 25.58 |
| 23.16 | 0.12 | 3.84 | 5538.73 | 52.06 |
| 23.40 | 0.14 | 3.80 | 2442.73 | 22.96 |
| 23.62 | 0.10 | 3.76 | 1684.01 | 15.83 |
| 23.83 | 0.10 | 3.73 | 1221.56 | 11.48 |
| 24.12 | 0.10 | 3.69 | 1055.36 | 9.92 |
| 24.33 | 0.14 | 3.66 | 3284.65 | 30.87 |
| 24.79 | 0.12 | 3.39 | 1884.52 | 17.71 |
| 25.17 | 0.14 | 3.54 | 1098.15 | 10.32 |
| 25.37 | 0.08 | 3.51 | 681.69 | 6.41 |
| 25.68 | 0.12 | 3.47 | 310.72 | 2.92 |
| 26.02 | 0.16 | 3.42 | 643.00 | 6.04 |
| 26.21 | 0.10 | 3.40 | 767.91 | 7.22 |
| 26.62 | 0.06 | 3.35 | 637.40 | 5.99 |
| 26.78 | 0.10 | 3.33 | 635.29 | 5.97 |
| 27.27 | 0.08 | 3.27 | 542.39 | 5.10 |
| 27.88 | 0.14 | 3.20 | 2484.53 | 23.35 |
| 28.11 | 0.08 | 3.17 | 1059.64 | 9.96 |
| 28.32 | 0.12 | 3.15 | 623.88 | 5.86 |
| 28.75 | 0.12 | 3.10 | 349.21 | 3.28 |
| 29.22 | 0.14 | 3.05 | 1105.91 | 10.39 |
| 29.62 | 0.08 | 3.01 | 415.32 | 3.90 |
| 29.92 | 0.14 | 2.98 | 553.36 | 5.20 |
| 30.33 | 0.06 | 2.94 | 398.32 | 3.74 |
| 31.58 | 0.20 | 2.83 | 274.93 | 2.58 |
| 32.37 | 0.06 | 2.76 | 476.89 | 4.48 |
| 32.47 | 0.06 | 2.76 | 480.47 | 4.52 |
| 32.75 | 0.08 | 2.73 | 433.65 | 4.08 |
| 33.08 | 0.08 | 2.71 | 294.98 | 2.77 |
| 33.67 | 0.16 | 2.66 | 238.12 | 2.24 |
| 33.97 | 0.12 | 2.64 | 204.64 | 1.92 |
| 34.50 | 0.12 | 2.60 | 821.63 | 7.72 |
| 34.86 | 0.08 | 2.57 | 709.22 | 6.67 |
| 35.44 | 0.16 | 2.53 | 223.02 | 2.10 |
| 35.81 | 0.10 | 2.51 | 368.00 | 3.46 |
| 36.12 | 0.24 | 2.48 | 329.40 | 3.10 |
| 36.64 | 0.16 | 2.45 | 368.45 | 3.46 |
| 36.86 | 0.12 | 2.44 | 306.62 | 2.88 |
| 37.85 | 0.12 | 2.38 | 168.13 | 1.58 |
| 38.32 | 0.24 | 2.35 | 165.87 | 1.56 |
| 39.27 | 0.24 | 2.29 | 97.06 | 0.91 |
| 39.66 | 0.16 | 2.27 | 198.78 | 1.87 |

$^1$H NMR Data $^1$H NMR (400 MHz, DMSO-d$_6$) b ppm 0.84 (d, J=6.39 Hz, 1H) 1.12 (d, J=7.25 Hz, 1H) 1.20-1.43 (m, 1H) 1.61-1.89 (m, 2H) 1.89-2.09 (m, 2H) 2.20-2.41 (m, 2H) 2.64-2.84 (m, 1H) 2.85-3.09 (m, 3H) 3.09-3.20 (m, 1H) 3.38-3.62 (m, 4H) 3.62-3.81 (m, 1H) 3.81-4.07 (m, 2H) 4.96 (br s, 2H) 5.35 (br dd, J=15.34, 9.16 Hz, 1H) 5.91-6.07 (m, 1H) 6.71 (d, J=8.10 Hz, 1H) 6.79-6.95 (m, 1H) 6.99 (dd, J=7.99, 1.60 Hz, 1H) 7.08-7.21 (m, 2H) 7.21-7.35 (m, 2H) 7.69 (d, J=8.52 Hz, 1H).

TABLE 7

X-ray Single Structure Data

| Crystal System | Orthorhombic |
|---|---|
| Space Group | P2$_1$2$_1$2$_1$ (19) |
| Unit Cell | a = 13.184 Å |
|  | b = 13.561 Å |
|  | c = 24.864 Å |
|  | α = β = γ = 90° |
| Volume | 4445.4 Å$^3$ |

Example 5: AMG 176 Diethanolamine Salt Anhydrous Form

AMG 176 diethanolamine toluene solvate was dried under vacuum at 50° C. Solids were identified as crystalline by XRPD.

TABLE 8

XRPD Data Table

| Pos. [°2Th.] | FWHM [°2Th.] | d-spacing [Å] | Height [cts] | Rel. Int. [%] |
|---|---|---|---|---|
| 6.58 | 0.05 | 13.44 | 776.36 | 5.21 |
| 7.77 | 0.07 | 11.37 | 5999.87 | 40.25 |
| 7.95 | 0.07 | 11.13 | 6983.90 | 46.85 |
| 9.51 | 0.07 | 9.30 | 780.96 | 5.24 |
| 10.23 | 0.08 | 8.65 | 8147.48 | 54.65 |
| 10.38 | 0.08 | 8.52 | 9831.24 | 65.94 |
| 12.27 | 0.10 | 7.21 | 5489.69 | 36.82 |
| 12.54 | 0.12 | 7.06 | 7958.70 | 53.38 |
| 13.19 | 0.08 | 6.71 | 7755.61 | 52.02 |
| 13.48 | 0.12 | 6.57 | 4285.18 | 28.74 |
| 13.76 | 0.10 | 6.44 | 6337.27 | 42.51 |
| 14.32 | 0.10 | 6.19 | 6624.17 | 44.43 |
| 14.88 | 0.07 | 5.96 | 4101.98 | 27.51 |
| 15.14 | 0.12 | 5.85 | 10110.99 | 67.82 |
| 15.50 | 0.13 | 5.72 | 9489.34 | 63.65 |
| 15.82 | 0.10 | 5.60 | 9456.40 | 63.43 |
| 15.95 | 0.05 | 5.56 | 4988.90 | 33.46 |
| 16.70 | 0.10 | 5.31 | 5083.31 | 34.10 |
| 17.11 | 0.13 | 5.18 | 10224.65 | 68.58 |
| 17.32 | 0.10 | 5.12 | 11086.27 | 74.36 |
| 17.55 | 0.10 | 5.05 | 4935.92 | 33.11 |
| 18.11 | 0.12 | 4.90 | 4759.36 | 31.92 |
| 18.26 | 0.07 | 4.86 | 3691.65 | 24.76 |
| 18.82 | 0.15 | 4.71 | 2618.41 | 17.56 |
| 19.40 | 0.18 | 4.58 | 3991.15 | 26.77 |
| 19.84 | 0.07 | 4.48 | 885.79 | 5.94 |
| 20.12 | 0.12 | 4.41 | 4860.93 | 32.61 |
| 20.37 | 0.10 | 4.36 | 2647.85 | 17.76 |
| 21.15 | 0.13 | 4.20 | 14908.33 | 100.00 |
| 21.57 | 0.13 | 4.12 | 3130.68 | 21.00 |
| 22.09 | 0.15 | 4.02 | 5931.79 | 39.79 |
| 22.37 | 0.12 | 3.97 | 3864.37 | 25.92 |
| 22.82 | 0.15 | 3.90 | 2303.31 | 15.45 |
| 23.12 | 0.10 | 3.85 | 819.39 | 5.50 |
| 23.56 | 0.12 | 3.78 | 2192.63 | 14.71 |
| 23.95 | 0.13 | 3.72 | 5840.25 | 39.17 |
| 24.33 | 0.12 | 3.66 | 2543.38 | 17.06 |
| 24.68 | 0.12 | 3.61 | 3821.75 | 25.64 |
| 25.01 | 0.12 | 3.56 | 4662.08 | 31.27 |
| 25.37 | 0.13 | 3.51 | 2236.35 | 15.00 |
| 25.73 | 0.12 | 3.46 | 1640.04 | 11.00 |
| 26.01 | 0.15 | 3.43 | 2457.72 | 16.49 |
| 26.24 | 0.12 | 3.40 | 2039.26 | 13.68 |
| 26.92 | 0.17 | 3.31 | 1030.25 | 6.91 |
| 27.36 | 0.12 | 3.26 | 1133.85 | 7.61 |
| 27.87 | 0.08 | 3.20 | 1647.52 | 11.05 |
| 28.80 | 0.15 | 3.10 | 1766.17 | 11.85 |
| 29.21 | 0.13 | 3.06 | 1059.91 | 7.11 |
| 29.65 | 0.23 | 3.01 | 1596.44 | 10.71 |
| 30.25 | 0.17 | 2.95 | 428.51 | 2.87 |
| 30.78 | 0.13 | 2.91 | 501.49 | 3.36 |

TABLE 8-continued

XRPD Data Table

| Pos. [°2Th.] | FWHM [°2Th.] | d-spacing [Å] | Height [cts] | Rel. Int. [%] |
|---|---|---|---|---|
| 31.37 | 0.47 | 2.85 | 595.28 | 3.99 |
| 32.00 | 0.15 | 2.80 | 685.09 | 4.60 |
| 32.77 | 0.17 | 2.73 | 416.77 | 2.80 |
| 33.04 | 0.10 | 2.71 | 247.84 | 1.66 |
| 33.91 | 0.20 | 2.64 | 534.74 | 3.59 |
| 34.59 | 0.15 | 2.59 | 930.49 | 6.24 |
| 35.16 | 0.17 | 2.55 | 810.15 | 5.43 |
| 35.97 | 0.27 | 2.50 | 888.13 | 5.96 |
| 36.27 | 0.13 | 2.48 | 595.29 | 3.99 |
| 36.66 | 0.20 | 2.45 | 789.62 | 5.30 |
| 37.46 | 0.30 | 2.40 | 788.74 | 5.29 |
| 38.51 | 0.20 | 2.34 | 415.65 | 2.79 |
| 39.12 | 0.30 | 2.30 | 450.38 | 3.02 |

$^1$H NMR Data $^1$H NMR (400 MHz, DMSO-$d_6$) δ ppm 0.85 (d, J=6.62 Hz, 4H) 1.14 (d, J=7.27 Hz, 4H) 1.27-1.46 (m, 1H) 1.58-1.79 (m, 4H) 1.79-2.04 (m, 8H) 2.21-2.45 (m, 3H) 2.64-2.91 (m, 3H) 2.91-3.04 (m, 5H) 3.09 (s, 3H) 3.17 (br d, J=14.10 Hz, 1H) 3.42-3.59 (m, 3H) 3.64 (br t, J=4.92 Hz, 4H) 3.73 (br d, J=14.75 Hz, 1H) 3.83-4.08 (m, 4H) 5.00-5.22 (m, 2H) 5.36 (dd, J=15.39, 9.19 Hz, 1H) 5.90-6.09 (m, 1H) 6.74 (d, J=7.91 Hz, 1H) 6.87-6.95 (m, 1H) 7.00 (dd, J=8.12, 1.71 Hz, 1H) 7.16 (d, J=2.35 Hz, 1H) 7.27 (dd, J=8.44, 2.46 Hz, 1H) 7.69 (d, J=8.55 Hz, 1H).

TABLE 9

X-ray Single Structure Data

| Crystal System | Monoclinic |
|---|---|
| Space Group | P2$_1$ (4) |
| Unit Cell | a = 13.417 Å |
| | b = 12.873 Å |
| | c = 22.211 Å |
| | α = γ = 90°, β = 91.79 |
| Volume | 3834.4 Å$^3$ |

Example 6: AMG 176 1,4-Dioxane Solvate

AMG 176 was slurried in 1,4-dioxane/water (70:30) for 14 days at 2-8° C. Solids were identified as crystalline by XRPD.

TABLE 10

XRPD Data Table

| Pos. [°2Th.] | FWHM [°2Th.] | d-spacing [Å] | Height [cts] | Rel. Int. [%] |
|---|---|---|---|---|
| 7.26 | 0.07 | 12.18 | 347.51 | 1.91 |
| 8.05 | 0.07 | 10.98 | 5289.43 | 29.02 |
| 10.07 | 0.07 | 8.78 | 2774.63 | 15.22 |
| 10.27 | 0.07 | 8.61 | 624.77 | 3.43 |
| 10.85 | 0.07 | 8.16 | 1738.49 | 9.54 |
| 12.43 | 0.08 | 7.12 | 18228.42 | 100.00 |
| 12.75 | 0.08 | 6.94 | 17443.45 | 95.69 |
| 13.97 | 0.08 | 6.34 | 5264.28 | 28.88 |
| 14.55 | 0.05 | 6.09 | 593.41 | 3.26 |
| 14.68 | 0.07 | 6.03 | 769.46 | 4.22 |
| 14.97 | 0.08 | 5.92 | 594.13 | 3.26 |
| 15.76 | 0.10 | 5.62 | 16496.49 | 90.50 |
| 16.15 | 0.07 | 5.49 | 10860.35 | 59.58 |
| 16.66 | 0.08 | 5.32 | 3095.97 | 16.98 |
| 17.38 | 0.08 | 5.10 | 2004.31 | 11.00 |
| 17.73 | 0.10 | 5.00 | 18174.37 | 99.70 |
| 17.96 | 0.08 | 4.94 | 11651.25 | 63.92 |
| 18.96 | 0.10 | 4.68 | 5385.90 | 29.55 |
| 19.39 | 0.10 | 4.58 | 14041.00 | 77.03 |
| 20.22 | 0.10 | 4.39 | 13381.92 | 73.41 |
| 20.34 | 0.08 | 4.37 | 10247.31 | 56.22 |
| 20.93 | 0.12 | 4.24 | 5619.77 | 30.83 |
| 21.51 | 0.10 | 4.13 | 6740.57 | 36.98 |
| 21.86 | 0.10 | 4.07 | 954.66 | 5.24 |
| 22.27 | 0.12 | 3.99 | 11145.24 | 61.14 |
| 22.82 | 0.10 | 3.90 | 8759.72 | 48.06 |
| 23.18 | 0.08 | 3.84 | 1659.55 | 9.10 |
| 23.45 | 0.10 | 3.79 | 5071.23 | 27.82 |
| 23.98 | 0.10 | 3.71 | 2295.15 | 12.59 |
| 24.18 | 0.07 | 3.68 | 1542.69 | 8.46 |
| 25.00 | 0.13 | 3.56 | 1832.86 | 10.05 |
| 25.42 | 0.08 | 3.50 | 1450.65 | 7.96 |
| 25.66 | 0.12 | 3.47 | 4029.30 | 22.10 |
| 26.08 | 0.10 | 3.42 | 1312.28 | 7.20 |
| 26.70 | 0.13 | 3.34 | 4191.03 | 22.99 |
| 27.10 | 0.13 | 3.29 | 1997.56 | 10.96 |
| 28.16 | 0.10 | 3.17 | 949.33 | 5.21 |
| 28.47 | 0.12 | 3.13 | 1174.21 | 6.44 |
| 29.09 | 0.10 | 3.07 | 467.17 | 2.56 |
| 29.61 | 0.12 | 3.02 | 1609.35 | 8.83 |
| 29.98 | 0.15 | 2.98 | 845.14 | 4.64 |
| 30.49 | 0.10 | 2.93 | 629.68 | 3.45 |
| 31.24 | 0.20 | 2.86 | 946.66 | 5.19 |
| 31.47 | 0.08 | 2.84 | 627.32 | 3.44 |
| 31.82 | 0.08 | 2.81 | 966.80 | 5.30 |
| 32.67 | 0.10 | 2.74 | 409.66 | 2.25 |
| 32.95 | 0.13 | 2.72 | 682.11 | 3.74 |
| 33.46 | 0.12 | 2.68 | 733.13 | 4.02 |
| 33.97 | 0.08 | 2.64 | 1693.06 | 9.29 |
| 35.17 | 0.07 | 2.55 | 669.79 | 3.67 |
| 35.88 | 0.17 | 2.50 | 848.04 | 4.65 |
| 36.37 | 0.10 | 2.47 | 865.73 | 4.75 |
| 36.75 | 0.13 | 2.45 | 327.66 | 1.80 |
| 37.09 | 0.08 | 2.42 | 744.90 | 4.09 |
| 37.56 | 0.20 | 2.39 | 503.19 | 2.76 |
| 38.47 | 0.10 | 2.34 | 568.62 | 3.12 |
| 38.95 | 0.12 | 2.31 | 417.20 | 2.29 |
| 39.77 | 0.08 | 2.27 | 665.14 | 3.65 |

TABLE 11

X-ray Single Structure Data

| Crystal System | Tetragonal |
|---|---|
| Space Groups | P4$_1$ (76), P4$_3$ (78), P4$_1$22 (91), P4$_3$22 (95) |
| Unit Cell | a = 12.165 Å |
| | b = 12.165 Å |
| | c = 25.333 Å |
| | α = β = γ = 90°° |
| Volume | 3749.1 Å$^3$ |

Example 7: AMG 176 Imidazole Salt Form A (Imidazole Salt Acetone Solvate)

AMG 176 and imidazole (1 eq) were dissolved in acetone. The solution was cooled to sub-ambient temperature and allowed to crystallize. Solids were identified as crystalline by XRPD.

TABLE 12

XRPD Data Table

| Pos. [°2Th.] | FWHM [°2Th.] | d-spacing [Å] | Height [cts] | Rel. Int. [%] |
|---|---|---|---|---|
| 4.24 | 0.07 | 20.82 | 14724.72 | 90.12 |
| 6.41 | 0.10 | 13.78 | 5928.15 | 36.28 |
| 7.02 | 0.08 | 12.59 | 5300.91 | 32.44 |
| 8.05 | 0.07 | 10.99 | 16339.76 | 100.00 |
| 8.50 | 0.08 | 10.40 | 7052.61 | 43.16 |
| 8.67 | 0.07 | 10.20 | 12437.34 | 76.12 |
| 9.11 | 0.08 | 9.71 | 5838.66 | 35.73 |
| 9.77 | 0.10 | 9.05 | 141.81 | 0.87 |
| 10.31 | 0.08 | 8.58 | 1569.63 | 9.61 |
| 10.70 | 0.08 | 8.27 | 4736.56 | 28.99 |
| 11.16 | 0.10 | 7.93 | 616.56 | 3.77 |
| 11.73 | 0.08 | 7.54 | 2708.99 | 16.58 |
| 12.03 | 0.10 | 7.35 | 2007.03 | 12.28 |
| 12.92 | 0.17 | 6.85 | 14025.36 | 85.84 |
| 13.79 | 0.10 | 6.42 | 5758.64 | 35.24 |
| 14.11 | 0.12 | 6.28 | 5414.50 | 33.14 |
| 15.13 | 0.12 | 5.85 | 4521.07 | 27.67 |
| 15.53 | 0.20 | 5.70 | 4764.85 | 29.16 |
| 16.40 | 0.15 | 5.41 | 8707.54 | 53.29 |
| 16.70 | 0.08 | 5.31 | 5361.86 | 32.81 |
| 17.38 | 0.13 | 5.10 | 8454.29 | 51.74 |
| 18.28 | 0.15 | 4.85 | 2841.97 | 17.39 |
| 18.47 | 0.08 | 4.81 | 2068.10 | 12.66 |
| 18.84 | 0.28 | 4.71 | 7805.11 | 47.77 |
| 19.68 | 0.10 | 4.51 | 6052.26 | 37.04 |
| 19.94 | 0.15 | 4.45 | 8029.03 | 49.14 |
| 20.67 | 0.15 | 4.30 | 15582.81 | 95.37 |
| 20.96 | 0.12 | 4.24 | 5087.65 | 31.14 |
| 21.36 | 0.18 | 4.16 | 2803.76 | 17.16 |
| 21.95 | 0.13 | 4.05 | 2526.87 | 15.46 |
| 22.38 | 0.13 | 3.97 | 4072.04 | 24.92 |
| 22.71 | 0.12 | 3.92 | 2343.72 | 14.34 |
| 23.60 | 0.17 | 3.77 | 5650.60 | 34.58 |
| 24.18 | 0.13 | 3.68 | 1445.97 | 8.85 |
| 24.75 | 0.12 | 3.60 | 1911.35 | 11.70 |
| 24.96 | 0.10 | 3.57 | 1484.83 | 9.09 |
| 25.59 | 0.13 | 3.48 | 2983.47 | 18.26 |
| 25.84 | 0.12 | 3.45 | 1803.54 | 11.04 |
| 26.80 | 0.20 | 3.33 | 2674.54 | 16.37 |
| 27.28 | 0.13 | 3.27 | 893.78 | 5.47 |
| 27.57 | 0.10 | 3.24 | 1125.89 | 6.89 |
| 27.83 | 0.10 | 3.21 | 1061.32 | 6.50 |
| 28.57 | 0.17 | 3.12 | 727.83 | 4.45 |
| 29.69 | 0.27 | 3.01 | 70.77 | 0.43 |
| 30.57 | 0.40 | 2.92 | 234.06 | 1.43 |
| 31.47 | 0.27 | 2.84 | 316.38 | 1.94 |
| 32.84 | 0.17 | 2.73 | 686.32 | 4.20 |
| 33.30 | 0.13 | 2.69 | 560.68 | 3.43 |
| 33.81 | 0.23 | 2.65 | 847.03 | 5.18 |
| 34.63 | 0.17 | 2.59 | 435.11 | 2.66 |
| 35.32 | 0.20 | 2.54 | 123.44 | 0.76 |
| 36.51 | 0.27 | 2.46 | 232.21 | 1.42 |
| 38.94 | 0.30 | 2.31 | 262.64 | 1.61 |

TABLE 13

X-ray Single Structure Data

| | |
|---|---|
| Crystal System | Orthorhombic |
| Space Groups | P2$_1$2$_1$2$_1$ (18) |
| Unit Cell | a = 27.302 Å |
| | b = 31.768 Å |
| | c = 10.976 Å |
| | α = β = γ = 90° |
| Volume | 9554.7 Å$^3$ |

Example 8: AMG 176 Hemi Magnesium Salt Dihydrate

AMG 176 (827 mg) was dissolved in ethanol (16.54 mL) and warmed to 55° C. Magnesium methoxide (0.742 mmol) was charged into the mixture and the mixture was held at 55° C. for 3 h and then cooled to room temperature. Solids were identified as crystalline by XRPD.

TABLE 14

XRPD Data Table

| Pos. [°2Th.] | FWHM [°2Th.] | d-spacing [Å] | Height [cts] | Rel. Int. [%] |
|---|---|---|---|---|
| 3.80 | 0.20 | 23.24 | 438.87 | 3.06 |
| 5.81 | 0.05 | 15.21 | 1899.44 | 13.23 |
| 7.49 | 0.12 | 11.80 | 14352.31 | 100.00 |
| 10.33 | 0.10 | 8.56 | 339.74 | 2.37 |
| 12.26 | 0.13 | 7.22 | 156.06 | 1.09 |
| 13.67 | 0.13 | 6.48 | 136.50 | 0.95 |
| 15.14 | 0.10 | 5.85 | 119.55 | 0.83 |
| 16.70 | 0.40 | 5.31 | 73.55 | 0.51 |
| 19.66 | 0.10 | 4.52 | 157.48 | 1.10 |
| 20.73 | 0.20 | 4.29 | 54.07 | 0.38 |
| 23.54 | 0.13 | 3.78 | 144.13 | 1.00 |

$^1$H NMR Data $^1$H NMR (400 MHz, DMSO-d$_6$) δ ppm 0.86 (br s, 3H) 1.04-1.18 (m, 3H) 1.32-1.42 (m, 1H) 1.61-1.79 (m, 3H) 1.85 (br s, 3H) 1.99 (br d, J=12.32 Hz, 4H) 2.28 (br s, 1H) 2.31-2.41 (m, 1H) 2.65-2.84 (m, 2H) 2.93-3.08 (m, 1H) 3.10 (s, 3H) 3.14-3.29 (m, 1H) 3.54 (br d, J=13.89 Hz, 2H) 3.68-3.82 (m, 1H) 3.82-4.03 (m, 3H) 5.31-5.43 (m, 1H) 6.73 (d, J=8.02 Hz, 1H) 6.92-6.99 (m, 1H) 7.02 (br s, 1H) 7.16 (d, J=2.15 Hz, 1H) 7.26 (dd, J=8.41, 1.96 Hz, 1H) 7.70 (d, J=8.41 Hz, 1H).

Example 9: AMG 176 Methyl tert-Butyl Ether Solvate

AMG 176 was slurried at room temperature in methyl tert-butyl ether (MTBE) for 1 day. Solids were identified as crystalline by XRPD.

TABLE 15

XRPD Data Table

| Pos. [°2Th.] | FWHM [°2Th.] | d-spacing [Å] | Height [cts] | Rel. Int. [%] |
|---|---|---|---|---|
| 3.42 | 0.05 | 25.84 | 573.82 | 1.76 |
| 7.24 | 0.05 | 12.21 | 509.29 | 1.56 |
| 8.02 | 0.05 | 11.02 | 16932.38 | 51.96 |
| 9.99 | 0.05 | 8.85 | 2243.75 | 6.88 |
| 10.25 | 0.07 | 8.63 | 1591.99 | 4.88 |
| 10.82 | 0.07 | 8.18 | 4131.78 | 12.68 |
| 12.36 | 0.08 | 7.16 | 29804.38 | 91.45 |
| 12.62 | 0.07 | 7.01 | 25108.70 | 77.05 |
| 13.77 | 0.07 | 6.43 | 14019.46 | 43.02 |
| 14.53 | 0.07 | 6.10 | 1004.37 | 3.08 |
| 14.94 | 0.07 | 5.93 | 1040.46 | 3.19 |
| 15.58 | 0.08 | 5.69 | 32239.66 | 98.93 |
| 16.08 | 0.07 | 5.51 | 11796.91 | 36.20 |
| 16.25 | 0.07 | 5.45 | 5676.13 | 17.42 |
| 16.62 | 0.08 | 5.34 | 6026.54 | 18.49 |
| 17.20 | 0.07 | 5.15 | 4196.55 | 12.88 |
| 17.66 | 0.08 | 5.02 | 27524.99 | 84.46 |
| 17.85 | 0.07 | 4.97 | 16599.50 | 50.93 |
| 18.72 | 0.08 | 4.74 | 13724.82 | 42.11 |
| 19.29 | 0.08 | 4.60 | 17827.73 | 54.70 |
| 20.09 | 0.12 | 4.42 | 32589.61 | 100.00 |
| 20.88 | 0.10 | 4.25 | 9570.60 | 29.37 |
| 21.36 | 0.07 | 4.16 | 7263.83 | 22.29 |
| 21.98 | 0.10 | 4.04 | 19133.91 | 58.71 |
| 22.61 | 0.10 | 3.93 | 12737.87 | 39.09 |
| 22.94 | 0.07 | 3.88 | 1828.01 | 5.61 |
| 23.17 | 0.10 | 3.84 | 6861.90 | 21.06 |

TABLE 15-continued

XRPD Data Table

| Pos. [°2Th.] | FWHM [°2Th.] | d-spacing [Å] | Height [cts] | Rel. Int. [%] |
|---|---|---|---|---|
| 23.33 | 0.07 | 3.81 | 1815.94 | 5.57 |
| 23.77 | 0.10 | 3.74 | 3020.37 | 9.27 |
| 24.23 | 0.08 | 3.67 | 731.43 | 2.24 |
| 24.86 | 0.10 | 3.58 | 3832.99 | 11.76 |
| 25.31 | 0.13 | 3.52 | 6435.25 | 19.75 |
| 25.92 | 0.10 | 3.44 | 2632.53 | 8.08 |
| 26.35 | 0.08 | 3.38 | 3399.01 | 10.43 |
| 26.44 | 0.07 | 3.37 | 4923.02 | 15.11 |
| 26.60 | 0.10 | 3.35 | 1833.68 | 5.63 |
| 26.96 | 0.12 | 3.31 | 1848.45 | 5.67 |
| 27.75 | 0.08 | 3.22 | 1006.28 | 3.09 |
| 27.97 | 0.08 | 3.19 | 631.80 | 1.94 |
| 28.35 | 0.12 | 3.15 | 1233.93 | 3.79 |
| 28.70 | 0.07 | 3.11 | 250.16 | 0.77 |
| 28.92 | 0.07 | 3.09 | 225.72 | 0.69 |
| 29.30 | 0.10 | 3.05 | 1415.43 | 4.34 |
| 29.49 | 0.07 | 3.03 | 1001.45 | 3.07 |
| 29.83 | 0.12 | 3.00 | 572.27 | 1.76 |
| 30.40 | 0.07 | 2.94 | 931.17 | 2.86 |
| 31.00 | 0.05 | 2.88 | 1048.15 | 3.22 |
| 31.19 | 0.07 | 2.87 | 1900.56 | 5.83 |
| 31.45 | 0.10 | 2.84 | 2642.81 | 8.11 |
| 31.99 | 0.07 | 2.80 | 330.88 | 1.02 |
| 32.84 | 0.08 | 2.73 | 1029.94 | 3.16 |
| 33.02 | 0.07 | 2.71 | 1220.90 | 3.75 |
| 33.34 | 0.13 | 2.69 | 439.73 | 1.35 |
| 33.70 | 0.15 | 2.66 | 1584.66 | 4.86 |
| 34.19 | 0.13 | 2.62 | 38.38 | 0.12 |
| 34.67 | 0.10 | 2.59 | 267.88 | 0.82 |
| 34.98 | 0.08 | 2.57 | 858.59 | 2.63 |
| 35.46 | 0.08 | 2.53 | 1202.58 | 3.69 |
| 36.08 | 0.08 | 2.49 | 879.75 | 2.70 |
| 36.37 | 0.08 | 2.47 | 464.76 | 1.43 |
| 36.94 | 0.20 | 2.43 | 473.80 | 1.45 |
| 37.35 | 0.12 | 2.41 | 292.30 | 0.90 |
| 37.59 | 0.27 | 2.39 | 240.15 | 0.74 |
| 37.97 | 0.10 | 2.37 | 245.38 | 0.75 |
| 38.32 | 0.17 | 2.35 | 692.93 | 2.13 |
| 39.22 | 0.08 | 2.30 | 1207.79 | 3.71 |

TABLE 16

X-ray Single Structure Data

| | |
|---|---|
| Crystal System | Tetragonal |
| Space Groups | P4 (75), P422 (89) |
| Unit Cell | a = 12.188 Å |
| | b = 12.188 Å |
| | c = 25.699 Å |
| | α = β = γ = 90° |
| Volume | 3817.6 Å³ |

Example 10: AMG 176 2-Methyltetrahydrofuran Solvate

AMG 176 (673 mg) was slurried in 2-MeTHF (10 mL) for 1 day at room temperature. Solids were identified as crystalline by XRPD.

TABLE 17

XRPD Data Table

| Pos. [°2Th.] | FWHM [°2Th.] | d-spacing [Å] | Height [cts] | Rel. Int. [%] |
|---|---|---|---|---|
| 7.29 | 0.05 | 12.13 | 541.80 | 1.09 |
| 8.06 | 0.07 | 10.97 | 20485.18 | 41.23 |
| 10.01 | 0.07 | 8.84 | 7831.96 | 15.76 |
| 10.32 | 0.07 | 8.57 | 1915.23 | 3.85 |
| 10.88 | 0.07 | 8.13 | 7616.54 | 15.33 |
| 12.40 | 0.07 | 7.14 | 46734.32 | 94.05 |
| 12.61 | 0.08 | 7.02 | 37872.63 | 76.22 |
| 13.72 | 0.08 | 6.46 | 15322.46 | 30.84 |
| 14.60 | 0.10 | 6.07 | 2285.36 | 4.60 |
| 15.03 | 0.07 | 5.90 | 600.45 | 1.21 |
| 15.55 | 0.08 | 5.70 | 45862.03 | 92.30 |
| 16.17 | 0.08 | 5.48 | 19007.95 | 38.25 |
| 16.37 | 0.08 | 5.42 | 7030.13 | 14.15 |
| 16.73 | 0.08 | 5.30 | 10887.80 | 21.91 |
| 17.20 | 0.08 | 5.16 | 6087.58 | 12.25 |
| 17.76 | 0.08 | 5.00 | 34513.69 | 69.46 |
| 17.92 | 0.07 | 4.95 | 20589.20 | 41.44 |
| 18.67 | 0.10 | 4.75 | 15665.50 | 31.53 |
| 19.36 | 0.10 | 4.58 | 29626.10 | 59.62 |
| 20.09 | 0.10 | 4.42 | 49688.30 | 100.00 |
| 21.03 | 0.12 | 4.22 | 13160.68 | 26.49 |
| 21.41 | 0.10 | 4.15 | 11278.76 | 22.70 |
| 21.92 | 0.12 | 4.06 | 31338.15 | 63.07 |
| 22.29 | 0.08 | 3.99 | 2812.92 | 5.66 |
| 22.63 | 0.12 | 3.93 | 22336.56 | 44.95 |
| 23.12 | 0.15 | 3.85 | 15015.92 | 30.22 |
| 23.49 | 0.08 | 3.79 | 2405.81 | 4.84 |
| 23.81 | 0.10 | 3.74 | 3845.31 | 7.74 |
| 24.24 | 0.12 | 3.67 | 2539.77 | 5.11 |
| 24.95 | 0.12 | 3.57 | 5446.49 | 10.96 |
| 25.24 | 0.10 | 3.53 | 8333.76 | 16.77 |
| 25.45 | 0.10 | 3.50 | 4874.42 | 9.81 |
| 26.04 | 0.10 | 3.42 | 2465.07 | 4.96 |
| 26.30 | 0.08 | 3.39 | 5916.83 | 11.91 |
| 26.47 | 0.10 | 3.37 | 5365.92 | 10.80 |
| 26.78 | 0.10 | 3.33 | 2844.89 | 5.73 |
| 27.08 | 0.13 | 3.29 | 3731.86 | 7.51 |
| 27.65 | 0.10 | 3.23 | 1381.57 | 2.78 |
| 28.05 | 0.10 | 3.18 | 867.98 | 1.75 |
| 28.53 | 0.17 | 3.13 | 2166.15 | 4.36 |
| 29.30 | 0.12 | 3.05 | 2495.62 | 5.02 |
| 29.73 | 0.12 | 3.00 | 664.29 | 1.34 |
| 30.00 | 0.13 | 2.98 | 1948.94 | 3.92 |
| 30.39 | 0.10 | 2.94 | 473.97 | 0.95 |
| 30.63 | 0.12 | 2.92 | 874.31 | 1.76 |
| 31.27 | 0.16 | 2.86 | 3691.12 | 7.43 |
| 31.38 | 0.06 | 2.86 | 3569.35 | 7.18 |
| 31.82 | 0.12 | 2.81 | 436.43 | 0.88 |
| 32.31 | 0.14 | 2.77 | 903.70 | 1.82 |
| 32.91 | 0.12 | 2.72 | 1306.05 | 2.63 |
| 33.06 | 0.12 | 2.71 | 1350.35 | 2.72 |
| 33.55 | 0.10 | 2.67 | 827.45 | 1.67 |
| 33.88 | 0.20 | 2.64 | 3008.00 | 6.05 |
| 34.36 | 0.12 | 2.61 | 285.37 | 0.57 |
| 34.80 | 0.18 | 2.58 | 369.62 | 0.74 |
| 35.19 | 0.14 | 2.55 | 1052.71 | 2.12 |
| 35.44 | 0.12 | 2.53 | 1620.50 | 3.26 |
| 35.95 | 0.08 | 2.50 | 620.35 | 1.25 |
| 36.21 | 0.16 | 2.48 | 2086.22 | 4.20 |
| 36.45 | 0.10 | 2.46 | 1018.17 | 2.05 |
| 37.08 | 0.14 | 2.42 | 571.86 | 1.15 |
| 37.34 | 0.16 | 2.41 | 928.26 | 1.87 |
| 37.85 | 0.10 | 2.38 | 991.37 | 2.00 |
| 38.56 | 0.08 | 2.33 | 1781.85 | 3.59 |
| 38.67 | 0.14 | 2.33 | 1652.72 | 3.33 |
| 39.14 | 0.18 | 2.30 | 1858.43 | 3.74 |

TABLE 18

X-ray Single Structure Data

| | |
|---|---|
| Crystal System | Tetragonal |
| Space Groups | P4₁ (76), P4₃ (78), P4₁22 (91), P4₃22 (95) |
| Unit Cell | a = 12.101 Å |
| | b = 12.101 Å |

TABLE 18-continued

| X-ray Single Structure Data | |
|---|---|
| | c = 25.804 Å |
| | α = β = γ = 90° |
| Volume | 3778.7 Å³ |

Example 11: AMG 176 Potassium Salt Hydrate

AMG 176 (200 mg) was dissolved in THF (2 mL) and then 10 mg of KOH was added and agitated to form a solution. Heptane (18 mL) was charged to precipitate solids. Solids were identified as crystalline by XRPD.

TABLE 19

XRPD Data Table

| Pos. [°2Th.] | FWHM [°2Th.] | d-spacing [Å] | Height [cts] | Rel. Int. [%] |
|---|---|---|---|---|
| 5.86 | 0.20 | 15.08 | 1220.34 | 100.00 |
| 7.55 | 0.54 | 11.71 | 622.44 | 51.01 |
| 11.20 | 0.40 | 7.90 | 161.46 | 13.23 |
| 13.58 | 0.27 | 6.52 | 245.62 | 20.13 |
| 15.34 | 0.80 | 5.78 | 139.95 | 11.47 |
| 16.93 | 0.54 | 5.24 | 166.65 | 13.66 |
| 18.51 | 0.27 | 4.79 | 465.38 | 38.14 |
| 22.53 | 0.40 | 3.95 | 230.99 | 18.93 |
| 23.54 | 0.54 | 3.78 | 698.27 | 57.22 |

Example 12: AMG 176 Potassium Salt Isopropanol Solvate

AMG 176 (200 mg) was dissolved in THF (2 mL) and then 10 mg of KOH was added and agitated to form a solution. Heptane (18 mL) was charged to precipitate solids. Solids were isolated then slurried in 1:1 IPA:water. Solids were identified as crystalline by XRPD.

TABLE 20

XRPD Data Table

| Pos. [°2Th.] | FWHM [°2Th.] | d-spacing [Å] | Height [cts] | Rel. Int. [%] |
|---|---|---|---|---|
| 3.75 | 0.40 | 23.55 | 92.59 | 3.27 |
| 5.80 | 0.12 | 15.23 | 2834.97 | 100.00 |
| 11.00 | 0.13 | 8.04 | 327.67 | 11.56 |
| 11.97 | 0.33 | 7.40 | 167.13 | 5.90 |
| 13.60 | 0.13 | 6.51 | 282.51 | 9.97 |
| 14.65 | 0.27 | 6.05 | 216.07 | 7.62 |
| 17.38 | 0.27 | 5.10 | 171.35 | 6.04 |
| 18.65 | 0.20 | 4.76 | 665.56 | 23.48 |
| 19.42 | 0.20 | 4.57 | 162.98 | 5.75 |
| 20.41 | 0.33 | 4.35 | 176.51 | 6.23 |
| 22.46 | 0.13 | 3.96 | 598.53 | 21.11 |
| 23.54 | 0.08 | 3.78 | 1027.29 | 36.24 |
| 29.17 | 0.40 | 3.06 | 110.79 | 3.91 |

$^1$H NMR Data $^1$H NMR (400 MHz, DMSO-$d_6$) δ ppm 0.82-0.95 (m, 5H) 1.05 (d, J=6.06 Hz, 3H) 1.17-1.42 (m, 7H) 1.62-1.80 (m, 3H) 1.80-2.08 (m, 7H) 2.17-2.33 (m, 1H) 2.39 (br d, J=6.85 Hz, 1H) 2.65-2.83 (m, 2H) 2.94-3.07 (m, 1H) 3.10 (s, 3H) 3.14-3.30 (m, 1H) 3.51-3.58 (m, 2H) 3.69-3.82 (m, 2H) 3.99 (q, J=12.26 Hz, 3H) 4.33 (d, J=4.11 Hz, 1H) 5.42 (br dd, J=14.67, 9.39 Hz, 1H) 5.89 (br s, 1H) 6.76-6.83 (m, 1H) 6.86 (br s, 1H) 7.02 (d, J=8.02 Hz, 1H) 7.15-7.19 (m, 1H) 7.27 (dd, J=8.51, 2.05 Hz, 1H) 7.68 (d, J=8.41 Hz, 1H).

Example 13: AMG 176 Tetrahydrofuran Solvate

AMG 176 (200 mg) was dissolved in tetrahydrofuran (THF, 2 mL). Heptane (18 mL) was charged into the mixture to precipitate solids. Solids were identified as crystalline by XRPD.

TABLE 21

XRPD Data Table

| Pos. [°2Th.] | FWHM [°2Th.] | d-spacing [Å] | Height [cts] | Rel. Int. [%] |
|---|---|---|---|---|
| 7.27 | 0.05 | 12.16 | 279.88 | 0.71 |
| 8.07 | 0.05 | 10.95 | 15965.49 | 40.22 |
| 10.10 | 0.05 | 8.76 | 8566.90 | 21.58 |
| 10.30 | 0.07 | 8.59 | 2977.00 | 7.50 |
| 10.87 | 0.05 | 8.14 | 3292.62 | 8.30 |
| 12.46 | 0.08 | 7.11 | 39692.68 | 100.00 |
| 12.78 | 0.08 | 6.93 | 30869.19 | 77.77 |
| 14.00 | 0.08 | 6.32 | 15134.57 | 38.13 |
| 14.58 | 0.07 | 6.07 | 1839.41 | 4.63 |
| 14.73 | 0.05 | 6.02 | 1112.21 | 2.80 |
| 14.99 | 0.08 | 5.91 | 764.01 | 1.92 |
| 15.80 | 0.08 | 5.61 | 32683.50 | 82.34 |
| 16.19 | 0.07 | 5.48 | 21985.69 | 55.39 |
| 16.33 | 0.05 | 5.43 | 5802.19 | 14.62 |
| 16.69 | 0.08 | 5.31 | 7855.73 | 19.79 |
| 17.41 | 0.07 | 5.09 | 5627.32 | 14.18 |
| 17.77 | 0.08 | 4.99 | 35391.39 | 89.16 |
| 18.00 | 0.08 | 4.93 | 21813.62 | 54.96 |
| 19.00 | 0.10 | 4.67 | 13171.56 | 33.18 |
| 19.44 | 0.08 | 4.57 | 27846.51 | 70.16 |
| 20.26 | 0.07 | 4.38 | 22126.85 | 55.75 |
| 20.38 | 0.07 | 4.36 | 21229.83 | 53.49 |
| 20.98 | 0.08 | 4.23 | 12651.19 | 31.87 |
| 21.56 | 0.10 | 4.12 | 15401.88 | 38.80 |
| 21.85 | 0.10 | 4.07 | 3036.21 | 7.65 |
| 22.32 | 0.12 | 3.98 | 21389.94 | 53.89 |
| 22.87 | 0.10 | 3.89 | 19640.98 | 49.48 |
| 23.06 | 0.05 | 3.86 | 3183.89 | 8.02 |
| 23.24 | 0.05 | 3.83 | 2724.36 | 6.86 |
| 23.50 | 0.10 | 3.79 | 9315.71 | 23.47 |
| 24.03 | 0.07 | 3.70 | 4343.01 | 10.94 |
| 24.21 | 0.08 | 3.68 | 3901.75 | 9.83 |
| 25.06 | 0.10 | 3.55 | 4739.37 | 11.94 |
| 25.48 | 0.08 | 3.50 | 2584.43 | 6.51 |
| 25.71 | 0.12 | 3.46 | 8311.11 | 20.94 |
| 26.13 | 0.12 | 3.41 | 2958.73 | 7.45 |
| 26.44 | 0.10 | 3.37 | 1456.47 | 3.67 |
| 26.76 | 0.13 | 3.33 | 9224.93 | 23.24 |
| 27.16 | 0.10 | 3.28 | 3830.87 | 9.65 |
| 28.22 | 0.08 | 3.16 | 2216.86 | 5.59 |
| 28.53 | 0.12 | 3.13 | 2866.93 | 7.22 |
| 29.18 | 0.07 | 3.06 | 1256.00 | 3.16 |
| 29.69 | 0.12 | 3.01 | 3329.92 | 8.39 |
| 30.05 | 0.12 | 2.97 | 1666.48 | 4.20 |
| 30.55 | 0.10 | 2.93 | 1949.00 | 4.91 |
| 31.17 | 0.08 | 2.87 | 1745.19 | 4.40 |
| 31.30 | 0.07 | 2.86 | 2008.42 | 5.06 |
| 31.51 | 0.08 | 2.84 | 1667.59 | 4.20 |
| 31.90 | 0.07 | 2.81 | 2444.56 | 6.16 |
| 32.40 | 0.10 | 2.76 | 605.54 | 1.53 |
| 32.77 | 0.07 | 2.73 | 1245.48 | 3.14 |
| 32.98 | 0.12 | 2.72 | 1303.45 | 3.28 |
| 33.23 | 0.10 | 2.70 | 941.47 | 2.37 |
| 33.55 | 0.10 | 2.67 | 1823.18 | 4.59 |
| 34.06 | 0.12 | 2.63 | 3901.80 | 9.83 |
| 34.17 | 0.06 | 2.63 | 2059.49 | 5.19 |
| 34.41 | 0.12 | 2.60 | 572.30 | 1.44 |
| 34.72 | 0.12 | 2.58 | 487.68 | 1.23 |
| 35.24 | 0.10 | 2.54 | 1627.96 | 4.10 |
| 35.98 | 0.12 | 2.49 | 1862.52 | 4.69 |
| 36.08 | 0.06 | 2.49 | 1716.84 | 4.33 |
| 36.46 | 0.10 | 2.46 | 2778.38 | 7.00 |
| 36.82 | 0.12 | 2.44 | 1019.73 | 2.57 |

TABLE 21-continued

XRPD Data Table

| Pos. [°2Th.] | FWHM [°2Th.] | d-spacing [Å] | Height [cts] | Rel. Int. [%] |
|---|---|---|---|---|
| 37.19 | 0.10 | 2.42 | 1421.00 | 3.58 |
| 37.58 | 0.08 | 2.39 | 1053.85 | 2.66 |
| 37.70 | 0.06 | 2.38 | 1260.26 | 3.18 |
| 37.97 | 0.16 | 2.37 | 661.01 | 1.67 |
| 38.57 | 0.10 | 2.33 | 1925.28 | 4.85 |
| 39.01 | 0.10 | 2.31 | 993.29 | 2.50 |
| 39.47 | 0.12 | 2.28 | 684.05 | 1.72 |
| 39.74 | 0.06 | 2.27 | 938.96 | 2.37 |

$^1$H NMR Data $^1$H NMR (400 MHz, DMSO-$d_6$) b ppm 0.97 (d, J=6.85 Hz, 3H) 1.30-1.44 (m, 4H) 1.66-1.84 (m, 7H) 1.88 (br d, J=7.63 Hz, 4H) 1.99 (br d, J=14.67 Hz, 1H) 2.06-2.27 (m, 3H) 2.39-2.49 (m, 1H) 2.67-2.84 (m, 2H) 3.02-3.13 (m, 4H) 3.17-3.31 (m, 1H) 3.53-3.65 (m, 6H) 3.75 (br d, J=15.06 Hz, 1H) 3.99-4.12 (m, 3H) 5.51 (br dd, J=14.67, 8.80 Hz, 1H) 5.74 (br s, 1H) 6.78 (s, 1H) 6.91 (d, J=8.02 Hz, 1H) 7.05 (dd, J=8.12, 1.66 Hz, 1H) 7.19 (d, J=2.15 Hz, 1H) 7.29 (dd, J=8.51, 2.25 Hz, 1H) 7.67 (d, J=8.61 Hz, 1H) 11.92 (s, 1H).

TABLE 22

X-ray Single Structure Data

| | |
|---|---|
| Crystal System | Tetragonal |
| Space Groups | P4$_1$ (76), P4$_3$ (78), P4$_1$22 (91), P4$_3$22 (95) |
| Unit Cell | a = 12.139 Å |
| | b = 12.139 Å |
| | c = 25.278 Å |
| | α = β = γ = 90° |
| Volume | 3724.6 Å$^3$ |

Example 14: AMG 176 Sodium Salt Acetonitrile Solvate

AMG 176 was slurried in acetonitrile with 1 eq NaOH at room temperature for 12 days. Solids were identified as crystalline by XRPD.

TABLE 23

XRPD Data Table

| Pos. [°2Th.] | FWHM [°2Th.] | d-spacing [Å] | Height [cts] | Rel. Int. [%] |
|---|---|---|---|---|
| 3.41 | 0.13 | 25.87 | 19969.38 | 79.20 |
| 3.66 | 0.22 | 24.15 | 25214.09 | 100.00 |
| 4.61 | 0.17 | 19.16 | 2343.06 | 9.29 |
| 5.72 | 0.17 | 15.46 | 1098.49 | 4.36 |
| 6.06 | 0.13 | 14.59 | 2363.99 | 9.38 |
| 6.89 | 0.07 | 12.83 | 3275.05 | 12.99 |
| 7.40 | 0.13 | 11.95 | 2641.43 | 10.48 |
| 8.22 | 0.08 | 10.76 | 1919.68 | 7.61 |
| 8.92 | 0.20 | 9.92 | 1586.13 | 6.29 |
| 9.20 | 0.17 | 9.61 | 1548.74 | 6.14 |
| 9.94 | 0.20 | 8.90 | 377.59 | 1.50 |
| 10.38 | 0.17 | 8.52 | 289.94 | 1.15 |
| 10.85 | 0.20 | 8.15 | 135.05 | 0.54 |
| 11.49 | 0.13 | 7.70 | 1088.43 | 4.32 |
| 11.84 | 0.13 | 7.47 | 436.91 | 1.73 |
| 12.30 | 0.20 | 7.20 | 653.97 | 2.59 |
| 12.83 | 0.17 | 6.90 | 726.38 | 2.88 |
| 13.47 | 0.17 | 6.57 | 3110.90 | 12.34 |
| 13.88 | 0.17 | 6.38 | 1533.52 | 6.08 |
| 14.35 | 0.10 | 6.17 | 2561.87 | 10.16 |
| 14.65 | 0.17 | 6.05 | 2735.02 | 10.85 |
| 15.91 | 0.10 | 5.57 | 1968.91 | 7.81 |
| 16.37 | 0.10 | 5.42 | 3040.22 | 12.06 |
| 16.65 | 0.13 | 5.33 | 5853.67 | 23.22 |
| 17.13 | 0.17 | 5.18 | 3912.19 | 15.52 |
| 17.62 | 0.10 | 5.03 | 3130.44 | 12.42 |
| 17.85 | 0.08 | 4.97 | 4519.56 | 17.92 |
| 18.71 | 0.13 | 4.74 | 3753.11 | 14.88 |
| 19.09 | 0.13 | 4.65 | 3001.93 | 11.91 |
| 19.27 | 0.10 | 4.61 | 2926.47 | 11.61 |
| 20.20 | 0.27 | 4.40 | 2877.15 | 11.41 |
| 20.95 | 0.12 | 4.24 | 4113.18 | 16.31 |
| 21.35 | 0.13 | 4.16 | 4221.62 | 16.74 |
| 21.65 | 0.13 | 4.11 | 4224.60 | 16.75 |
| 22.42 | 0.13 | 3.97 | 3597.26 | 14.27 |
| 23.85 | 0.20 | 3.73 | 3201.83 | 12.70 |
| 24.21 | 0.17 | 3.68 | 3251.90 | 12.90 |
| 24.70 | 0.17 | 3.60 | 3327.62 | 13.20 |
| 25.31 | 0.27 | 3.52 | 2474.85 | 9.82 |
| 25.91 | 0.20 | 3.44 | 2192.98 | 8.70 |
| 26.53 | 0.54 | 3.36 | 1688.56 | 6.70 |
| 26.96 | 0.20 | 3.31 | 1697.82 | 6.73 |
| 28.36 | 0.33 | 3.15 | 948.21 | 3.76 |
| 31.43 | 0.80 | 2.85 | 69.79 | 0.28 |
| 33.01 | 0.27 | 2.71 | 209.89 | 0.83 |
| 34.15 | 0.40 | 2.63 | 136.44 | 0.54 |
| 35.93 | 0.40 | 2.50 | 83.47 | 0.33 |
| 37.45 | 0.80 | 2.40 | 104.90 | 0.42 |

The foregoing description is given for clearness of understanding only, and no unnecessary limitations should be understood therefrom, as modifications within the scope of the invention may be apparent to those having ordinary skill in the art.

Throughout this specification and the claims which follow, unless the context requires otherwise, the word "comprise" and variations such as "comprises" and "comprising" will be understood to imply the inclusion of a stated integer or step or group of integers or steps but not the exclusion of any other integer or step or group of integers or steps.

Throughout the specification, where compositions are described as including components or materials, it is contemplated that the compositions can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

The practice of a method disclosed herein, and individual steps thereof, can be performed manually and/or with the aid of or automation provided by electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method, unless described otherwise. In addition, some of the individual steps can be combined, omitted, or further subdivided into additional steps.

The use of the terms "a," "an," "the," and similar referents in the context of the disclosure herein (especially in the context of the claims) are to be construed to cover both the singular and the plural, unless otherwise indicated. Recitation of ranges of values herein merely are intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the disclosure herein and is not a limitation on the scope of the disclosure herein unless otherwise indicated. No language in the specification should be construed as indicating any non-claimed element as essential to the practice of the disclosure herein.

All patents, publications and references cited herein are hereby fully incorporated by reference. In case of conflict between the present disclosure and incorporated patents, publications and references, the present disclosure should control.

What is claimed is:

1. A crystalline form of AMG 176
   (i) as an ammonium salt, characterized by XRPD pattern peaks at 16.6, 17.6, and 18.4±0.2° 2θ using Cu Kα radiation;
   (ii) as a diethylamine salt characterized by an XRPD pattern substantially as shown in FIG. 5;
   (iii) as a diethylamine salt characterized by an XRPD pattern substantially as shown in FIG. 7;
   (iv) as a diethanolamine salt characterized by an XRPD pattern substantially as shown in FIG. 9;
   (v) as a diethanolamine salt characterized by an XRPD pattern substantially as shown in FIG. 11;
   (vi) as a 1,4-dioxane solvate characterized by XRPD pattern peaks at 12.4, 12.8, 15.8, and 17.7±0.2° 2θ using Cu Kα radiation;
   (vii) as an imidazole salt acetone solvate characterized by XRPD pattern peaks at 4.2, 8.1, and 20.7±0.2° 2θ using Cu Kα radiation;
   (viii) as a hemi magnesium salt dihydrate characterized by XRPD pattern peaks at 3.8, 5.8, and 7.5±0.2° 2θ using Cu Kα radiation;
   (ix) as a methyl tert-butyl ether solvate characterized by XRPD pattern peaks at 12.4, 15.6, and 20.1±0.2° 2θ using Cu Kα radiation;
   (x) as a 2-methyltetrahydrofuran solvate characterized by XRPD pattern peaks at 12.4, 15.6, and 20.1±0.2° 2θ using Cu Kα radiation;
   (xi) as a potassium salt hydrate characterized by XRPD pattern peaks at 5.9, 7.6, and 23.5±0.2° 2θ using Cu Kα radiation;
   (xii) as a potassium salt isopropanol solvate characterized by XRPD pattern peaks at 5.8, 18.7, 22.5, and 23.5±0.2° 2θ using Cu Kα radiation;
   (xiii) as a tetrahydrofuran solvate characterized by XRPD pattern peaks at 12.5, 15.8, and 17.8±0.2° 2θ using Cu Kα radiation; or
   (xiv) as a sodium salt acetonitrile solvate characterized by XRPD pattern peaks at 3.4, 3.7, and 16.7±0.2° 2θ using Cu Kα radiation.

2. The crystalline form of claim 1, wherein the form is the ammonium salt and is further characterized by XRPD pattern peaks at 19.2, 21.6, 22.4, and 23.8±0.2° 2θ using Cu Kα radiation, optionally further characterized by XRPD pattern peaks at 7.9, 10.1, 11.0, 12.7, 13.9, 20.2, 24.9, 27.7, and 29.8±0.2° 2θ using Cu Kα radiation.

3. The crystalline form of claim 1, wherein the form is the diethylamine salt characterized by an XRPD pattern substantially as shown in FIG. 5 has an endothermic transition at 148° C. to 154° C. as measured by differential scanning calorimetry.

4. The crystalline form of claim 1, wherein the form is the diethylamine salt characterized by an XRPD pattern substantially as shown in FIG. 7 has an endothermic transition at 140° C. to 260° C. as measured by differential scanning calorimetry.

5. The crystalline form of claim 1, wherein the form is the diethanolamine salt characterized by an XRPD pattern substantially as shown in FIG. 9, and has an endothermic transition at 134° C. to 230° C. as measured by differential scanning calorimetry.

6. The crystalline form of claim 1, wherein the form is the diethanolamine salt characterized by an XRPD pattern substantially as shown in FIG. 11, and has an endothermic transition at 126° C. to 240° C. as measured by differential scanning calorimetry.

7. The crystalline form of claim 1, wherein the form is the 1,4-dioxane solvate and is further characterized by XRPD pattern peaks at 18.0, 19.4, 20.2, and 22.3±0.2° 2θ using Cu Kα radiation.

8. The crystalline form of claim 1, wherein the form is the imidazole salt acetone solvate and is further characterized by XRPD pattern peaks at 8.7, 12.9, 16.4, and 17.4±0.2° 2θ using Cu Kα radiation.

9. The crystalline form of claim 1, wherein the form is the hemi magnesium salt dihydrate and is further characterized by XRPD pattern peaks at 10.3, 12.3, 13.7, 15.1, 16.7, 19.7, 20.7, and 23.5±0.2° 2θ using Cu Kα radiation.

10. The crystalline form of claim 1, wherein the form is the methyl tert-butyl ether solvate and is further characterized by XRPD pattern peaks at 3.0, 12.6, 17.7, 17.9, 19.3, and 22.0±0.2° 2θ using Cu Kα radiation.

11. The crystalline form of claim 1, wherein the form is the 2-methyltetrahydrofuran solvate and is further characterized by XRPD pattern peaks at 12.6, 17.8, 19.4, and 21.9±0.2° 2θ using Cu Kα radiation.

12. The crystalline form of claim 1, wherein the form is the potassium salt hydrate and is further characterized by XRPD pattern peaks at 11.2, 13.6, 15.3, 16.9, 18.5, and 22.5±0.2° 2θ using Cu Kα radiation.

13. The crystalline form of claim 1, wherein the form is the potassium salt isopropanol solvate and is further characterized by XRPD pattern peaks at 11.0, 12.0, 13.6, 14.7, 17.4, 19.4, 20.4, and 29.2±0.2° 2θ using Cu Kα radiation.

14. The crystalline form of claim 1, wherein the form is the tetrahydrofuran solvate and is further characterized by XRPD pattern peaks at 4.8, 16.2, 18.0, 19.4, 20.3, 20.4, and 22.3±0.2° 2θ using Cu Kα radiation.

15. The crystalline form of claim 1, wherein the form is the sodium salt acetonitrile solvate and is further characterized by XRPD pattern peaks at 17.1, 17.9, 21.0, 21.4, and 21.7±0.2° 2θ using Cu Kα radiation.

16. A method of treating a subject suffering from cancer, comprising administering to the subject a therapeutically effective amount of the crystalline form of claim 1.

17. The method of claim 16, wherein the cancer is multiple myeloma, non-Hodgkin's lymphoma, or acute myeloid leukemia.

\* \* \* \* \*